US010538798B2

(12) United States Patent
Matsuda et al.

(10) Patent No.: US 10,538,798 B2
(45) Date of Patent: Jan. 21, 2020

(54) METHOD FOR SECRETORY PRODUCTION OF PROTEIN

(71) Applicant: AJINOMOTO CO., INC., Tokyo (JP)

(72) Inventors: Yoshihiko Matsuda, Kanagawa (JP); Yumi Ito, Kanagawa (JP); Yukari Kashima, Kanagawa (JP); Naoko Yamada, Kanagawa (JP); Noriko Tsurui, Kanagawa (JP); Hiroshi Itaya, Kanagawa (JP)

(73) Assignee: AJINOMOTO CO., INC., Tokyo (JP)

( * ) Notice: Subject to any disclaimer, the term of this patent is extended or adjusted under 35 U.S.C. 154(b) by 26 days.

(21) Appl. No.: 15/790,495

(22) Filed: Oct. 23, 2017

(65) Prior Publication Data

US 2018/0037918 A1 Feb. 8, 2018

Related U.S. Application Data

(63) Continuation of application No. PCT/JP2016/062675, filed on Apr. 21, 2016.

(30) Foreign Application Priority Data

Apr. 24, 2015 (JP) .................................. 2015-089046

(51) Int. Cl.
*C12P 21/00* (2006.01)
*C07K 14/34* (2006.01)
*C12N 9/12* (2006.01)

(52) U.S. Cl.
CPC .............. *C12P 21/00* (2013.01); *C07K 14/34* (2013.01); *C12N 9/12* (2013.01); *C12Y 207/13003* (2013.01); *C07K 2319/02* (2013.01)

(58) Field of Classification Search
None
See application file for complete search history.

(56) References Cited

U.S. PATENT DOCUMENTS

| | | | |
|---|---|---|---|
| 4,965,197 A | 10/1990 | Liebl et al. | |
| 6,027,920 A | 2/2000 | Joliff et al. | |
| 9,187,554 B2 | 11/2015 | Matsuda et al. | |
| 9,376,701 B2 | 6/2016 | Tsurui et al. | |
| 9,404,138 B2 | 8/2016 | Matsuda et al. | |
| 2003/0082746 A1 | 5/2003 | Kikuchi et al. | |
| 2004/0126847 A1 | 7/2004 | Kikuchi et al. | |
| 2007/0184525 A1 | 8/2007 | Date et al. | |
| 2010/0297729 A1 | 11/2010 | Kikuchi et al. | |
| 2014/0220637 A1 | 8/2014 | Tsurui et al. | |
| 2014/0234901 A1 | 8/2014 | Matsuda et al. | |

FOREIGN PATENT DOCUMENTS

| | | | |
|---|---|---|---|
| JP | 6-502548 A | 3/1994 | |
| JP | 11-169182 A | 6/1999 | |
| JP | 4320769 B2 | 6/2009 | |
| JP | 4362651 B2 | 8/2009 | |
| JP | 4730302 B2 | 4/2011 | |
| WO | WO2004/035792 A1 | 4/2004 | |
| WO | WO2005/103278 A1 | 11/2005 | |
| WO | WO2006/069610 A2 | 7/2006 | |
| WO | WO2013/062029 A1 | 5/2013 | |
| WO | WO2013/065772 A1 | 5/2013 | |
| WO | WO2013/065869 A1 | 5/2013 | |
| WO | WO2013/118544 A1 | 8/2013 | |

OTHER PUBLICATIONS

Wu et al., "*Corynebacterium humireducens* sp. nov., an alkaliphilic, humic acid-reducing bacterium isolated from a microbial fuel cell", Int. J. Sys. Evol. Microbiol. 61:882-887, 2011 (Year: 2011).*
UniProt Database Accession No. A0A0B5DAP9, Apr. 1, 2015, 1 page (Year: 2015).*
International Search Report for PCT Patent App. No. PCT/JP2016/062675 (dated Jul. 26, 2016) with English translation of the ISR.
Billman-Jacobe, H., et al., "Expression and Secretion of Heterologous Proteases by Corynebacterium glutamicum," Appl. Environmen. Microbiol. 1995;61(4):1610-1613.
Bott, M., et al., "Two-component signal transduction in Corynebacterium glutamicum and other corynebacteria: on the way towards stimuli and targets," Appl. Microbiol. Biotechnol. 2012;94:1131-1150.
Chaddock, A. M., et al., "A new type of signal peptide: central role of a twin-arginine motif in transfer signals for the Δph-dependent thylakoidal protein translocase," The EMBO Journal 1995;14(12):2715-2722.
Christensen, T., et al., "High Level Expression of Recombinant Genes in Aspergillus Oryzae," Biotechnol. 1988;6:1419-1422.
Cregg, J. M., et al., "Recent Advances in the Expression of Foreign Genes in Pichia pastoris," Biotechnol. 1993;11:905-910.
Dunn-Coleman, N. S., et al., "Commercial Levels of Chymosin Production by Aspergillus," Biotechnol. 1991;9:976-981.
Hynds, P. J., et al., "The Sec-independent Twin-arginine Translocation System Can Transport Both Tightly Folded and Malfolded Proteins across the Thylakoid Membrane," J. Biol. Chem. 1998;273(52):34868-34874.
International Preliminary Report on Patentability for PCT Patent App. No. PCT/JP2016/062675 (dated Nov. 2, 2017).
Kocan, M., et al., "Two-Component Systems of Corynebacterium glutamicum: Deletion Analysis and Involvement of the PhoS-PhoR System in the Phosphate Starvation Response," J. Bacteriol. 2006;188(2):724-732.

(Continued)

*Primary Examiner* — David Steadman
(74) *Attorney, Agent, or Firm* — Cermak Nakajima & McGowan LLP; Shelly Guest Cermak

(57) ABSTRACT

A novel technique for improving secretory production of a heterologous protein by coryneform bacteria is described, as well as a method for secretory production of a heterologous protein. A coryneform bacterium is described that has been modified to have a specific mutation so as to harbor a phoS gene, and when cultured, is able to to produce a heterologous protein by secretory production.

13 Claims, 9 Drawing Sheets

Specification includes a Sequence Listing.

(56) References Cited

OTHER PUBLICATIONS

Liebl, W., et al., "Expression, Secretion, and Processing of Staphylococcal Nuclease by Corynebacterium glutamicum," J. Bacteriol. 1992;174(6):1854-1861.

Panhorst, M., et al., "The pstSCAB operon for phosphate uptake is regulated by the global regulator GlxR in Corynebacterium glutamicum," J. Biotechnol. 2011;154:149-155.

Salim, K., et al., "Heterologous Expression of the *Mycobacterium tuberculosis* Gene Encoding Antigen 85A in Corynebacterium glutamicum," Appl. Environmen. Microbiol. 1997;63(11):4392-4400.

Simonen, M., et al., "Protein Secretion in *Bacillus* Species," Microbiol. Rev. 1993;57(1):109-137.

Extended European Search Report for European Patent App. No. 16783245.0 (dated Sep. 13, 2018).

\* cited by examiner

```
                    phospho-accepting His
                              ↓                           (302)
                                                            ↓
YDK0107      266 QMRRFVGDASHELRTPLTSVKGPTELYSSGATDDANCVMSKIGGEAQRMSVLVEDLLSLTRAEGQ 330
YDK010       266 QMRPFVGDASHELPTPLTSVKGPTELYSSGATDDANWMSKIGGEAQRMSVLVEDLLSLTRAEGQ 330
ATCC13869    266 QMRRFVGDASHELRTPLTSVKGFTELYSSGATDDANWMSKIGGEAQRMSVLVEDLLSLTRAEGQ 330
ATCC13032    266 QMRRFVGDASHELRTPLTSVKGFTELYSSGATDDANWMSKIGGEAQRMSVLVEDLLSLTRAEGQ 330
ATCC14067    266 QMRRFVGDASHELRTPLTSVKGFTELYSSGATDDANWMSKIGGEAQRMSVLVEDLLSLTRAEGQ 330
C. callunae  285 QMRRFVGDASHELPTPLTSVKGFTELYSSGATQDALWLSKIGGEAQRMSVLVEDLLSLTRAEGQ 349
C. crenatum  239 QMRRFVGDASHELRTPLTSVKGFTELYSSGATDDANWMSKIGGEAQRMSVLVEDLLSLTRAEGQ 303
C. efficiens 250 QMPRFVGDASHELRTPLTSVKGYSELYHSGATRDALWLSKISGEAQRMSVLVEDLLSLTRAEGQ 314
                 **********************..***.****.**.**.***.****************
                 _____/
                                         HisKA domain
```

FIGURE 2

METHOD FOR SECRETORY PRODUCTION OF PROTEIN

This application is a Continuation of, and claims priority under 35 U.S.C. § 120 to International Application PCT/JP2016/062675, filed Apr. 21, 2016, and claims priority therethrough under 35 U.S.C. § 119 to Japanese Patent Application No. 2015-089046, filed Apr. 24, 2015, the entirety of which is incorporated by reference herein. Also, the Sequence Listing filed electronically herewith is hereby incorporated by reference (File name: 2017-10-23T_US-568_Seq_List; File size: 76 KB; Date recorded: Oct. 23, 2017).

BACKGROUND OF THE INVENTION

Field of the Invention

The present invention relates to a method for secretory production of a heterologous protein.

Description of the Related Art

Methods for secretory production of heterologous proteins by microorganisms have been reported in, for example, a *Bacillus* bacterium (Microbiol. Rev., 57, 109-137 (1993)), methanol-assimilating yeast, *Pichia pastoris* (Biotechnol., 11, 905-910 (1993)), filamentous fungi of the genus *Aspergillus* (Biotechnol., 6, 1419-1422 (1988); Biotechnol., 9, 976-981 (1991)), and so forth.

Secretory production of heterologous proteins in coryneform bacteria has also been attempted, and methods reported include secretion of a nuclease and a lipase by *Corynebacterium glutamicum* (henceforth also abbreviated as *C. glutamicum*) (U.S. Pat. No. 4,965,197, J. Bacteriol., 174, 1854-1861 (1992)), secretion of a protease such as subtilisin (Appl. Environ. Microbiol., 61, 1610-1613 (1995)), secretion of a protein using signal peptides of cell surface layer proteins PS1 and PS2 (also referred to as CspB) of coryneform bacteria (Japanese Patent Laid-open (Kohyo) No. 6-502548), secretion of a fibronectin-binding protein using the signal peptide of PS2 (CspB) (Appl. Environ. Microbiol., 61, 1610-1613 (1995)), secretion of protransglutaminase using signal peptides of PS2 (CspB) and SlpA (also referred to as CspA) (Japanese Patent No. 4320769), secretion of a protein using a variant type secretion system (Japanese Patent Laid-open (Kokai) No. 11-169182), secretion of a protransglutaminase by a variant strain (Japanese Patent No. 4362651), and so forth. In addition, techniques for improving secretory production amounts of heterologous proteins by coryneform bacteria are known and include reducing the activity of a cell surface layer protein (WO2013/065869 and WO2013/065772), reducing the activity of a penicillin-binding protein (WO2013/065869), enhancing the expression of a gene encoding a metallopeptidase (WO2013/065772), introducing a mutation into a ribosomal protein S1 gene (WO2013/118544), expressing a heterologous protein with an amino acid sequence comprising Gln-Glu-Thr inserted between a signal peptide and the heterologous protein (WO2013/062029), and so forth.

The "Sec system" is a general protein secretion pathway and is widely present in both prokaryotes and eukaryotes; however, an entirely different protein secretion pathway has recently been found in thylakoid membranes of chloroplasts of plant cells (EMBO J., 14, 2715-2722(1995)). This novel secretory pathway has been named the "Tat system" (Twin-Arginine Translocation system) due to the arginine-arginine sequence that is commonly present in the signal sequence of a secreted protein secreted (EMBO J., 14, 2715-2722 (1995)). Proteins secreted by the Sec system are in a precursor state before forming a higher-order structure, while proteins secreted by the Tat system through the cell membrane have already formed a higher-order structure in the cell (J. Biol. Chem., 25; 273(52), 34868-74(1998)). Secretory production of proteins utilizing a Tat-dependent signal peptide has been reported in coryneform bacteria (WO2013/118544; Japanese Patent No. 4730302).

A "two-component regulatory system" is a system in which bacteria respond to various environmental changes both inside and outside of the cell. The two-component regulatory system has two components: a sensor kinase that is responsible for sensing an environmental change stimulus, and a response regulator that is responsible for receiving a signal from the sensor kinase and regulating the expression of downstream genes. When the sensor kinase senses a stimulus, a specific histidine residue in the kinase is autophosphorylated, a signal is transduced via transfer of the phosphate group to a specific aspartic acid residue in the response regulator, and thereby the phosphorylated response regulator is activated as a transcription factor to regulate the expression of the downstream genes.

The two-component regulatory system of *C. glutamicum* is described in Appl. Microbiol. Biotechnol., 94, 1131-1150 (2012), etc. For *C. glutamicum*, at least 13 types of systems are known to be two-component regulatory systems. One of these is the PhoRS system, which includes a sensor kinase PhoS protein and a response regulator PhoR protein. Analysis of a PhoRS-deficient strain revealed that the PhoRS system is a regulatory system that senses phosphate depletion in the environment and performs signal transduction (J. Bacteriol., 188, 724-732(2006)).

The PhoS protein is a membrane protein having two transmembrane domains. The PhoS protein includes a sensor domain that senses a stimulus, a linker domain called a HAMP domain, a HisKA domain having a histidine residue that is autophosphorylated, and a HATPase domain that is able to bind ATP catalyze autophosphorylation of the histidine residue. The PhoR protein is an intracellular protein that includes a receiver domain on the N-terminal side that receives a signal, and an effector domain on the C-terminal side that regulates the expression of the downstream genes (Appl. Microbiol. Biotechnol., 94, 1131-1150(2012)).

However, the relationship between the PhoRS system and the secretory production of heterologous proteins has not been previously described. Also, the effect of a mutation of the PhoS protein is unknown, nor has such a mutation been reported to be effective for secretory production of heterologous proteins in coryneform bacteria. Furthermore, that the effect of specific mutations of the PhoS protein and their relationship to secretory production of heterologous proteins has not been previously reported.

BRIEF SUMMARY OF THE INVENTION

It is one aspect of the present invention to develop a novel technique for improving secretory production of a heterologous protein by a coryneform bacterium, and thereby to provide a method for secretory production of a heterologous protein using a coryneform bacterium. The ability of a coryneform bacterium to produce a heterologous protein by secretory production can be improved by modifying the coryneform bacterium so as to harbor a phoS gene having a specific mutation.

It is an aspect of the present invention to provide a method for producing a heterologous protein comprising culturing a coryneform bacterium having a genetic construct that allows for secretory expression of a heterologous protein; and collecting the heterologous protein produced by secretory production, wherein the coryneform bacterium has been modified so as to harbor a phoS gene encoding a PhoS protein with a mutation, wherein the mutation results in improved secretory production of the heterologous protein as compared to a bacterium without the mutation, wherein the genetic construct comprises, in the direction from 5' to 3', a promoter sequence that is able to function in the coryneform bacterium, a nucleic acid sequence encoding a signal peptide that functions in the coryneform bacterium, and a nucleic acid sequence encoding the heterologous protein, and wherein the heterologous protein is expressed as a fusion protein with the signal peptide.

It is a further aspect of the present invention to provide the method as described above, wherein the mutation is replacing an amino acid residue other than a histidine residue that is autophosphorylated with another amino acid residue in a wild-type PhoS protein.

It is a further aspect of the present invention to provide the method as described above, wherein the mutation is replacing an autophosphorylated amino acid residue that is not a histidine residue in a HisKA domain of a wild-type PhoS protein with another amino acid residue.

It is a further aspect of the present invention to provide the method as described above, wherein the mutation is replacing the amino acid residue at position 302 in SEQ ID NO: 4 with an amino acid residue other than an aromatic amino acid residue and a histidine residue.

It is a further aspect of the present invention to provide a method for producing a heterologous protein comprising culturing a coryneform bacterium having a genetic construct that allows for secretory expression of a heterologous protein; and collecting the heterologous protein produced by secretory production, wherein the coryneform bacterium has been modified so as to harbor a phoS gene encoding a PhoS protein with a mutation, wherein the mutation is replacing an amino acid residue at position 302 in SEQ ID NO: 4 with an amino acid residue other than an aromatic amino acid and a histidine residue in a wild-type PhoS protein, wherein the genetic construct comprises, in the direction from 5' to 3', a promoter sequence that is able to function in the coryneform bacterium, a nucleic acid sequence encoding a signal peptide that is able to function in the coryneform bacterium, and a nucleic acid sequence encoding the heterologous protein, and wherein the heterologous protein is expressed as a fusion protein with the signal peptide.

It is a further aspect of the present invention to provide the method as described above, wherein the amino acid residue other than an aromatic amino acid residue and a histidine residue is selected from the group consisting of lysine, alanine, valine, serine, cysteine, methionine, aspartic acid, and asparagine.

It is a further aspect of the present invention to provide the method as described above, wherein the wild-type PhoS protein is selected from the group consisting of (a) a protein comprising the amino acid sequence of SEQ ID NO: 4, 54, 55, 56, 57, or 58; (b) a protein comprising the amino acid sequence of SEQ ID NO: 4, 54, 55, 56, 57, or 58, but which includes substitution, deletion, insertion, or addition of 1 to 10 amino acid residues; and (c) a protein comprising an amino acid sequence having an identity of 90% or higher to the amino acid sequence of SEQ ID NO: 4, 54, 55, 56, 57, or 58.

It is a further aspect of the present invention to provide the method as described above, wherein the signal peptide is a Tat-dependent signal peptide.

It is a further aspect of the present invention to provide the method as described above, wherein the Tat-dependent signal peptide is selected from the group consisting of TorA, SufI, PhoD, LipA, and IMD.

It is a further aspect of the present invention to provide the method as described above, wherein the coryneform bacterium has been further modified so that the expression of one or more genes encoding a Tat secretion system is/are increased.

It is a further aspect of the present invention to provide the method as described above, wherein the genes encoding a Tat secretion system are tatA, tatB, tatC, and tatE.

It is a further aspect of the present invention to provide the method as described above, wherein the signal peptide is a Sec-dependent signal peptide.

It is a further aspect of the present invention to provide the method as described above, wherein the Sec-dependent signal peptide is selected from the group consisting of PS1, PS2, and SlpA.

It is a further aspect of the present invention to provide the method as described above, wherein the genetic construct further comprises a nucleic acid sequence encoding an amino acid sequence comprising Gln-Glu-Thr between the nucleic acid sequence encoding the signal peptide that is able to function in the coryneform bacterium and the nucleic acid sequence encoding the heterologous protein.

It is a further aspect of the present invention to provide the method as described above, wherein the genetic construct further comprises a nucleic acid sequence encoding an amino acid sequence capable of enzymatic digestion between the nucleic acid sequence encoding the amino acid sequence comprising Gln-Glu-Thr and the nucleic acid sequence encoding the heterologous protein.

It is a further aspect of the present invention to provide the method as described above, wherein the coryneform bacterium belongs to the genus *Corynebacterium*.

It is a further aspect of the present invention to provide the method as described above, wherein the coryneform bacterium is *Corynebacterium glutamicum*.

It is a further aspect of the present invention to provide the method as described above, wherein the coryneform bacterium is a modified *Corynebacterium glutamicum* AJ12036 (FERM BP-734) strain or a modified *Corynebacterium glutamicum* ATCC13869 strain.

It is a further aspect of the present invention to provide the method as described above, wherein the coryneform bacterium has reduced activity of a cell surface layer protein.

It is a further aspect of the present invention to provide a coryneform bacterium, which has been modified so as to harbor a phoS gene encoding a PhoS protein with a mutation, wherein the mutation is one that results in replacing an amino acid residue at position 302 in SEQ ID NO: 4 with an amino acid residue other than an aromatic amino acid residue and a histidine residue.

It is a further aspect of the present invention to provide the coryneform bacterium as described above, wherein the amino acid residue other than an aromatic amino acid residue and a histidine residue is selected from the group consisting of lysine, alanine, valine, serine, cysteine, methionine, aspartic acid, and asparagine.

It is a further aspect of the present invention to provide the coryneform bacterium as described above, wherein the wild-type PhoS protein is selected from the group consisting of (a) a protein comprising the amino acid sequence of SEQ ID NO: 4, 54, 55, 56, 57, or 58; (b) a protein comprising the amino acid sequence of SEQ ID NO: 4, 54, 55, 56, 57, or 58, but which includes substitution, deletion, insertion, or addition of 1 to 10 amino acid residues; and (c) a protein comprising an amino acid sequence having an identity of 90% or higher to the amino acid sequence of SEQ ID NO: 4, 54, 55, 56, 57, or 58.

It is a further aspect of the present invention to provide the coryneform bacterium as described above, wherein the coryneform bacterium belongs to the genus *Corynebacterium*.

It is a further aspect of the present invention to provide the coryneform bacterium as described above, wherein the coryneform bacterium is *Corynebacterium glutamicum*.

It is a further aspect of the present invention to provide the coryneform bacterium as described above, wherein the coryneform bacterium is a modified *Corynebacterium glutamicum* AJ12036 (FERM BP-734) or a modified *Corynebacterium glutamicum* ATCC13869 strain.

It is a further aspect of the present invention to provide the coryneform bacterium as described above, wherein the coryneform bacterium has reduced activity of a cell surface layer protein.

BRIEF DESCRIPTION OF THE DRAWINGS

FIG. 2 is a diagram showing an alignment of the amino acid sequences of HisKA domains of PhoS homologues of *Corynebacterium* bacteria, as follows: *C. glutamicum* YDK0107 (SEQ ID No: 59), *C. glutamicum* YDK010 (SEQ ID No. 60), *C. glutamicum* ATCC 13869 (SEQ ID No. 61), *C. glutamicum* ATCC 13032 (SEQ ID No. 62), *C. glutamicum* ATCC 14067 (SEQ ID No. 63), *C. callunae* (SEQ ID No. 64), *C. crenatum* (SEQ ID No. 65), and *C. efficiens* (SEQ ID No. 66).

DETAILED DESCRIPTION OF THE INVENTION

Figure 1:
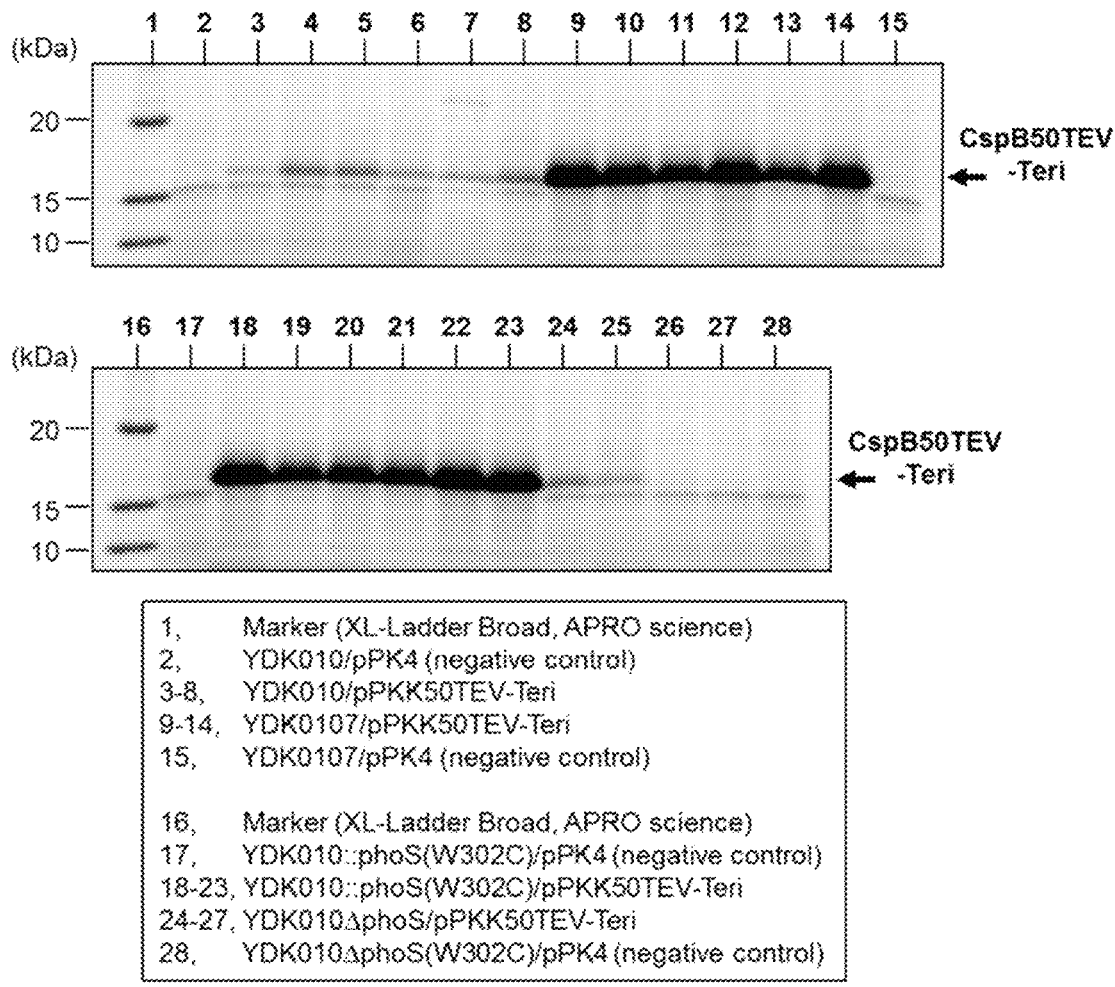
FIG. 1 is a photograph showing the results of SDS-PAGE observed upon expressing CspB50TEV-Teri (Teriparatide fused with CspB signal sequence and mature CspB N-terminal sequence) in the *C. glutamicum* YDK010 strain, and PhoS(W302C)-mutant and PhoS-deletion strains thereof.

<1> Method for Producing a Heterologous Protein

The present invention provides a method for producing a heterologous protein, the method including the steps of culturing a coryneform bacterium having a genetic construct that allows for secretory expression of the heterologous protein, and collecting the heterologous protein produced by the secretory production, wherein the coryneform bacterium has been modified so as to harbor a phoS gene encoding a PhoS protein with a mutation (henceforth also referred to as "method of the present invention" or "method for producing a heterologous protein of the present invention").

<1-1> Coryneform Bacterium

The coryneform bacterium that can be used in the method as described herein has a genetic construct that is engineered for secretory expression of a heterologous protein and has been modified so as to harbor a mutant phoS gene. This coryneform bacterium can also be referred to as "bacterium of the present invention" or "coryneform bacterium of the present invention". Furthermore, the genetic construct for secretory expression of a heterologous protein harbored by the bacterium can also be referred to as "genetic construct used for the present invention".

<1-1-1> Coryneform Bacterium Having Ability of Secretory Production of Heterologous Protein The coryneform bacterium has the genetic construct that allows for secretory expression of a heterologous protein (genetic construct used for the method of the present invention), and therefore has an ability of secretory production of the heterologous protein.

The expression that a protein is "secreted" can mean that the protein is transported out of a bacterial cell (extracellularly transported). Positions outside of a bacterial cell (outside of a cell) can include the medium and the cell surface layer. That is, the expression that a protein is "secreted" is not limited to when all of the molecules of the protein eventually are present in the medium as completely free forms, and also can include when all of the molecules of the protein are present in the cell surface layer, and also when just some of the molecules of the protein are present in the medium and the remaining molecules of the protein are present in the cell surface layer.

That is, the term "ability to produce a heterologous protein by secretory production" can refer to an ability of the bacterium as described herein to secrete the heterologous protein into a medium or a cell surface layer, and accumulate it there to such an extent that the heterologous protein can be collected from the medium or the cell surface layer, when the bacterium is cultured in the medium. The accumulation amount may be, for example, in terms of the accumulation amount in the medium, 10 μg/L or more, 1 mg/L or more, 100 mg/L or more, or 1 g/L or more. Also, the accumulation amount may be, for example, in terms of the accumulation amount in the cell surface layer, such an amount that if the heterologous protein in the cell surface layer is collected and suspended in a liquid of the same volume as the medium, the concentration of the heterologous protein in the suspension can be 10 μg/L or more, 1 mg/L or more, 100 mg/L or more. In addition, the term "protein" to be produced by secretory production can referto a peptide, such as oligopeptides and polypeptides.

The term "heterologous protein" can refer to an exogenous protein relative to the coryneform bacterium that expresses and secretes that protein. The heterologous protein may be, for example, a protein that is native to a microorganism, a plant, an animal, a virus, or can even be an artificially designed protein. The heterologous protein may be a monomeric protein or a multimeric protein. The term "multimeric protein" can refer to a protein that may exist as a multimer having two or more subunits. In the multimer, the subunits may be linked by covalent bonds such as disulfide bonds, linked by non-covalent bonds such as hydrogen bonds and hydrophobic interaction, or linked by a combination thereof. The multimer can include one or more intermolecular disulfide bonds. The multimer may be a homo-multimer having a single kind of subunit, or may be a hetero-multimer having two or more kinds of subunits. When the multimeric protein is a hetero-multimer, at least one subunit is heterologous. That is, all the subunits may be heterologous, or only some of the subunits may be heterologous. Although the heterologous protein may be a secretory protein in nature, or may be a non-secretory protein in nature, it is preferably a secretory protein in nature. Furthermore, the heterologous protein may be a Tat-dependent secretory protein in nature, or may be a Sec-dependent secretory protein in nature. Specific examples of the "heterologous protein" will be described herein.

The heterologous protein to be produced may be a single kind of protein, or two or more kinds of proteins. Moreover, when the heterologous protein is a hetero-multimer, only one kind of subunit may be produced, or two or more kinds of subunits may be produced. That is, the term "secretory production of a heterologous protein" can include secretory production of all the subunits of the objective heterologous protein, as well as secretory production of only some of the subunits of the objective heterologous protein.

Coryneform bacteria are aerobic gram-positive bacilli. Examples of the coryneform bacteria include *Corynebacterium* bacteria, *Brevibacterium* bacteria, *Microbacterium* bacteria, and so forth. Advantages of the coryneform bacteria include that they inherently secrete an extremely small amount of proteins out of cells compared with fungi, yeasts, Bacillus bacteria, etc., which are conventionally used for secretory production of proteins. Therefore the purification process of a heterologous protein produced by secretory production in a coryneform bacteria is expected to be very simple or even unnecessary, since they can grow well in a simple medium containing a saccharide, ammonia, mineral salts, etc. Therefore, coryneform bacteria are considered to be excellent in view of cost of medium, culture method, and culture productivity, and so forth.

Specific examples of coryneform bacteria include the following species:
*Corynebacterium acetoacidophilum*
*Corynebacterium acetoglutamicum*
*Corynebacterium alkanolyticum*
*Corynebacterium callunae*
*Corynebacterium crenatum*
*Corynebacterium glutamicum*
*Corynebacterium lilium*
*Corynebacterium melassecola*
*Corynebacterium thermoaminogenes* (*Corynebacterium efficiens*)
*Corynebacterium herculis*
*Brevibacterium divaricatum* (*Corynebacterium glutamicum*)
*Brevibacterium flavum* (*Corynebacterium glutamicum*)
*Brevibacterium immariophilum*
*Brevibacterium lactofermentum* (*Corynebacterium glutamicum*)
*Brevibacterium roseum*
*Brevibacterium saccharolyticum*
*Brevibacterium thiogenitalis*
*Corynebacterium ammoniagenes* (*Corynebacterium stationis*)
*Brevibacterium album*
*Brevibacterium cerinum*
*Microbacterium ammoniaphilum*

Specific examples of coryneform bacteria include the following strains:
*Corynebacterium acetoacidophilum* ATCC 13870
*Corynebacterium acetoglutamicum* ATCC 15806
*Corynebacterium alkanolyticum* ATCC 21511
*Corynebacterium callunae* ATCC 15991
*Corynebacterium crenatum* AS1.542
*Corynebacterium glutamicum* ATCC 13020, ATCC 13032, ATCC 13060, ATCC 13869, FERM BP-734
*Corynebacterium lilium* ATCC 15990
*Corynebacterium melassecola* ATCC 17965
*Corynebacterium thermoaminogenes* (*Corynebacterium efficiens*) AJ12340 (FERM BP-1539)
*Corynebacterium herculis* ATCC 13868
*Brevibacterium divaricatum* (*Corynebacterium glutamicum*) ATCC 14020
*Brevibacterium flavum* (*Corynebacterium glutamicum*) ATCC 13826, ATCC 14067, AJ12418 (FERM BP-2205)
*Brevibacterium immariophilum* ATCC 14068
*Brevibacterium lactofermentum* (*Corynebacterium glutamicum*) ATCC 13869
*Brevibacterium roseum* ATCC 13825
*Brevibacterium saccharolyticum* ATCC 14066
*Brevibacterium thiogenitalis* ATCC 19240
*Corynebacterium ammoniagenes* (*Corynebacterium stationis*) ATCC 6871, ATCC 6872
*Brevibacterium album* ATCC 15111
*Brevibacterium cerinum* ATCC 15112
*Microbacterium ammoniaphilum* ATCC 15354

The *Corynebacterium* bacteria can include bacteria that had previously been classified into the genus *Brevibacterium*, but are now united into the genus *Corynebacterium* (Int. J. Syst. Bacteriol., 41, 255 (1991)). Moreover, *Corynebacterium stationis* includes bacteria that had previously been classified as *Corynebacterium ammoniagenes*, but are now re-classified into *Corynebacterium stationis* on the basis of nucleotide sequence analysis of 16S rRNA etc. (Int. J. Syst. Evol. Microbiol., 60, 874-879 (2010)).

These strains are available from, for example, the American Type Culture Collection (Address: P.O. Box 1549, Manassas, Va. 20108, United States of America). That is, registration numbers are assigned to the respective strains, and the strains can be ordered by using these registration numbers (refer to atcc.org) The registration numbers of the strains are listed in the catalogue of the American Type Culture Collection. These strains can also be obtained from, for example, the depositories at which the strains were deposited.

In particular, the *Corynebacterium glutamicum* (*C. glutamicum*) AJ12036 strain (FERM BP-734), which was isolated as a streptomycin (Sm) resistant mutant strain from a wild-type strain *C. glutamicum* ATCC 13869, is predicted to have a mutation in a gene responsible for a function involved in secretion of proteins. This strain is able to produce and secrete proteins in extremely high amounts, for example, about 2 to 3 times in terms of the amount accumulated under optimum culture conditions, as compared with a parent strain or a wild-type strain, and therefore is considered optimal as a host bacterium. The AJ12036 strain was originally deposited at the Fermentation Research Institute, Agency of Industrial Science and Technology (currently, independent administrative agency, National Institute of Technology and Evaluation, International Patent Organism Depositary, #120, 2-5-8 Kazusakamatari, Kisarazu-shi, Chiba-ken, 292-0818, Japan) on Mar. 26, 1984 as an international deposit, and assigned an accession number of FERM BP-734.

*Corynebacterium thermoaminogenes* AJ12340 (FERM BP-1539) was originally deposited at the Fermentation Research Institute, Agency of Industrial Science and Technology (currently, independent administrative agency, National Institute of Technology and Evaluation, International Patent Organism Depositary, #120, 2-5-8 Kazusakamatari, Kisarazu-shi, Chiba-ken, 292-0818, Japan) on Mar. 13, 1987 as an international deposit, and assigned an accession number of FERM BP-1539. *Brevibacterium flavum* AJ12418 (FERM BP-2205) was originally deposited at the Fermentation Research Institute, Agency of Industrial Science and Technology (currently, independent administrative agency, National Institute of Technology and Evaluation, International Patent Organism Depositary, #120, 2-5-8 Kazusakamatari, Kisarazu-shi, Chiba-ken, 292-0818, Japan) on Dec. 24, 1988 as an international deposit, and assigned an accession number of FERM BP-2205.

Moreover, host strains having an enhanced ability to produce and secrete a protein may be selected from parent strains of coryneform bacterium after mutagenesis or genetic recombination. For example, after a parent strain is treated with ultraviolet irradiation or a chemical mutation agent such as N-methyl-N'-nitrosoguanidine, a strain having an enhanced ability to produce a protein by secretory production can be selected.

Furthermore, if a host strain obtained by modifying a parent or wild-type strain so that it does not produce a cell surface layer protein is selected, purification of the heterologous protein secreted in the medium or on the cell surface layer is simplified, and therefore it is particularly preferred. Such modification can be carried out by introducing a mutation into the coding region of the cell surface layer protein or an expression control region thereof, on the chromosome by mutagenesis or genetic recombination. Examples of coryneform bacterium modified so that it does not produce a cell surface layer protein include the *C. glutamicum* YDK010 strain (WO2004/029254), which is a cell surface layer protein PS2 deficient strain of the *C. glutamicum* AJ12036 strain (FERM BP-734).

A coryneform bacterium having an ability of secretory production of a heterologous protein can be obtained by introducing the genetic construct as described herein into such a coryneform bacterium as described above so that the bacterium harbors the genetic construct. The genetic construct used for the method as described herein and methods for introduction of the same will be described later.

<1-1-2> Introduction of Mutant phoS Gene

The bacterium as described herein can be modified so as to harbor a mutant phoS gene. The expression "to harbor a mutant phoS gene" can also be referred to as "to have a mutant phoS gene" or "to have a mutation in a phoS gene". In addition, the expression "to harbor a mutant phoS gene" can also be referred to as "to have a mutant PhoS protein" or "to have a mutation in a PhoS protein". The bacterium can be obtained by modifying a coryneform bacterium having an ability of secretory production of a heterologous protein so that it harbors a mutant phoS gene. The bacterium can also be obtained by modifying a coryneform bacterium so as to harbor a mutant phoS gene, and then imparting an ability of secretory production of a heterologous protein thereto. Modifications for constructing the bacterium can be performed in any arbitrary order. The strain chosen for constructing the bacterium as described herein and before being modified so as to harbor a mutant phoS gene may or may not be able to produce a heterologous protein, on the assumption that the strain has the genetic construct for secretory expression of the heterologous protein. That is, the chosen bacterium may also be, for example, a bacterium that has acquired an ability of secretory production of a heterologous protein due to being modified so as to harbor a mutant phoS gene. Specifically, for example, the bacterium may also be a bacterium obtained from a strain that is not able to produce a heterologous protein by secretory production even when it has the genetic construct for secretory expression of the heterologous protein but before it is modified so as to harbor a mutant phoS gene, which came to be able to produce the heterologous protein by secretory production due to being modified so as to harbor a mutant phoS gene.

Hereinafter, the phoS gene and the PhoS protein will be described. The phoS gene is a gene encoding a PhoS protein, which is a sensor kinase of the PhoRS system. The PhoRS system is one of two-component regulatory systems, and induces a response against phosphate depletion. The PhoRS system has a sensor kinase PhoS encoded by a phoS gene and a response regulator PhoR encoded by a phoR gene.

A PhoS protein having the "specific mutation" can also be referred to as "mutant PhoS protein", and a gene encoding it can also be referred to as "mutant phoS gene". The mutant phoS gene is, in other words, a phoS gene having the "specific mutation". Furthermore, in the present invention, a PhoS protein not having the "specific mutation" can also be referred to as "wild-type PhoS protein", and a gene encoding it can also be referred to as "wild-type phoS gene". The wild-type phoS gene is, in other words, a phoS gene not having the "specific mutation". The term "wild-type" can be used to distinguish a "wild-type" gene/protein from a "mutant" gene/protein, and "wild-type" is not limited to gene/proteins obtained as natural substances, so long as the gene/proteins do not have the "specific mutation". The "specific mutation" will be described later.

Examples of the wild-type phoS gene can include, for example, phoS genes native to coryneform bacteria. Specific examples of the phoS genes native to coryneform bacteria can include, for example, the phoS genes of *C. glutamicum* YDK010, *C. glutamicum* ATCC 13032, *C. glutamicum* ATCC 14067, *C. callunae*, *C. crenatum*, and *C. efficiens*. The nucleotide sequence of the phoS gene of *C. glutamicum* YDK010 is shown as SEQ ID NO: 3. The amino acid sequences of the wild-type PhoS proteins encoded by these phoS genes are shown as SEQ ID NOS: 4, 54, 55, 56, 57, and 58, respectively. That is, the wild-type phoS gene may be, for example, a gene having the nucleotide sequence shown as SEQ ID NO: 3. Also, the wild-type PhoS protein may be, for example, a protein having the amino acid sequence shown as SEQ ID NO: 4, 54, 55, 56, 57, or 58. The expression "a gene or protein has a nucleotide or amino acid sequence" can include when the gene or protein includes only these sequences, but also can includes when the gene or protein includes these sequences within other sequences.

The wild-type phoS gene may be a variant of any of the wild-type phoS genes exemplified above, so long as it does not have the "specific mutation" and the original function thereof is maintained. Similarly, the wild-type PhoS protein may be a variant of any of the proteins encoded by the wild-type phoS genes exemplified above, so long as it does not have the "specific mutation" and the original function thereof is maintained. Such a variant can also be referred to as "conservative variant". The term "wild-type phoS gene" can include not only the wild-type phoS genes exemplified above, but also can include conservative variants thereof that do not have the "specific mutation". Similarly, the term "wild-type PhoS protein" can include not only the proteins encoded by the wild-type phoS genes exemplified above, but also can include conservative variants thereof that do not have the "specific mutation". Examples of the conservative variants can include, for example, homologues and artificially modified versions of the wild-type phoS genes and wild-type PhoS proteins exemplified above.

The expression "the original function is maintained" can mean that a variant of a gene or protein has a function (such as activity or property) corresponding to the function (such as activity or property) of the original gene or protein. That is, the expression "the original function is maintained" in reference to the wild-type phoS gene may mean that a variant of the gene encodes a protein that maintains its original function. Furthermore, the expression "the original function is maintained" in reference to the wild-type PhoS protein may mean that a variant of the protein functions as a sensor kinase of the PhoRS system. The term "functions as a sensor kinase of the PhoRS system" may specifically refer to a function of inducing a response against phosphate depletion in the environment in combination with a response regulator PhoR protein. The term "functions as a sensor kinase of the PhoRS system" may more specifically refer to a function of sensing phosphate depletion in the environment to be autophosphorylated, and activating the PhoR protein via transfer of phosphate group.

Whether or not a variant of the PhoS protein functions as a sensor kinase of the PhoRS system can be confirmed by, for example, introducing a gene encoding the variant into a phoS-gene-deletion strain of a coryneform bacterium, and confirming whether or not responsiveness against phosphate depletion is complemented. Complementation of responsiveness against phosphate depletion can be detected, for example, as improvement of growth under phosphate depletion conditions, or as induction of the expression of genes of which the expression is known to be induced under phosphate depletion conditions (J. Bacteriol., 188, 724-732 (2006)). As the phoS-gene-deletion strain of a coryneform bacterium, for example, a phoS-gene-deletion strain of *C. glutamicum* YDK010 or a phoS-gene-deletion strain of *C. glutamicum* ATCC13032 can be used.

Hereinafter, examples of the conservative variants will be explained.

Homologues of the wild-type phoS genes can be easily obtained from public databases by, for example, BLAST search or FASTA search using any of the nucleotide sequences of the wild-type phoS genes exemplified above as a query sequence. Furthermore, homologues of the wild-type phoS genes can be obtained by, for example, PCR using a chromosome of coryneform bacteria as the template, and oligonucleotides prepared on the basis of any of the nucleotide sequences of these known wild-type phoS genes as primers.

The wild-type PhoS protein may have any of the amino acid sequences of the wild-type PhoS proteins exemplified above (SEQ ID NO: 4, 54, 55, 56, 57, or 58), but which can include substitution, deletion, insertion, or addition of one or several amino acid residues at one or several positions, so long as it does not have the "specific mutation" and the original function thereof is maintained. Although the number meant by the term "one or several" mentioned above may differ depending on the positions of amino acid residues in the three-dimensional structure of the protein or the types of amino acid residues, specifically, it can be 1 to 20, 1 to 10, 1 to 5, or 1 to 3.

The aforementioned substitution, deletion, insertion, or addition of one or several amino acid residues can be a conservative mutation that maintains the normal function of the protein. Typical examples of the conservative mutation are conservative substitutions. The conservative substitution is a mutation wherein substitution takes place mutually among Phe, Trp, and Tyr, if the substitution site is an aromatic amino acid; among Leu, Ile, and Val, if it is a hydrophobic amino acid; between Gln and Asn, if it is a polar amino acid; among Lys, Arg, and His, if it is a basic amino acid; between Asp and Glu, if it is an acidic amino acid; and between Ser and Thr, if it is an amino acid having a hydroxyl group. Examples of substitutions considered as conservative substitutions include, specifically, substitution of Ser or Thr for Ala, substitution of Gln, His, or Lys for Arg, substitution of Glu, Gln, Lys, His, or Asp for Asn, substitution of Asn, Glu, or Gln for Asp, substitution of Ser or Ala for Cys, substitution of Asn, Glu, Lys, His, Asp, or Arg for Gln, substitution of Gly, Asn, Gln, Lys, or Asp for Glu, substitution of Pro for Gly, substitution of Asn, Lys, Gln, Arg, or Tyr for His, substitution of Leu, Met, Val, or Phe for Ile, substitution of Ile, Met, Val, or Phe for Leu, substitution of Asn, Glu, Gln, His, or Arg for Lys, substitution of Ile, Leu, Val, or Phe for Met, substitution of Trp, Tyr, Met, Ile, or Leu for Phe, substitution of Thr or Ala for Ser, substitution of Ser or Ala for Thr, substitution of Phe or Tyr for Trp, substitution of His, Phe, or Trp for Tyr, and substitution of Met, Ile, or Leu for Val. Furthermore, such substitution, deletion, insertion, or addition of amino acid residues as mentioned above includes a naturally occurring mutation due to an individual difference, or a difference of species of the bacterium from which the gene is derived (mutant or variant).

The wild-type PhoS protein may also have an amino acid sequence having a homology of, for example, 80% or more, 90% or more, 95% or more, 97% or more, 99% or more, to the total amino acid sequence of any of the amino acid sequences of the wild-type PhoS proteins exemplified above (SEQ ID NO: 4, 54, 55, 56, 57, or 58), so long as it does not have the "specific mutation" and the original function thereof is maintained. In this description, "homology" can mean "identity".

It is preferred that a histidine residue that is autophosphorylated is conserved. That is, a conservative mutation can occur at an amino acid residue other than the histidine residue that is autophosphorylated. The term "histidine residue that is autophosphorylated" can refer to a histidine residue at position 276 of the wild-type PhoS protein. Furthermore, it is preferred that, for example, the wild-type PhoS protein has a conservative sequence of the wild-type PhoS proteins exemplified above. That is, it is preferred that a conservative mutation occurs at, for example, an amino acid residue not conserved in the wild-type PhoS proteins exemplified above.

The wild-type phoS gene may also be DNA that is able to hybridize under stringent conditions with a complementary sequence of any of the nucleotide sequences of the wild-type phoS genes exemplified above (e.g. SEQ ID NO: 3), or with a probe that can be prepared from the complementary sequence, so long as it does not have the "specific mutation" and the original function thereof is maintained. The term "stringent conditions" can refer to conditions under which a so-called specific hybrid is formed, and a non-specific hybrid is not formed. Examples of the stringent conditions can include those under which highly homologous DNAs hybridize to each other, for example, DNAs not less than 80% homologous, not less than 90% homologous, not less than 95% homologous, not less than 97% homologous, not less than 99% homologous, hybridize to each other, and DNAs less homologous than the above do not hybridize to each other, or can be conditions of washing of typical Southern hybridization, i.e., conditions of washing once, or 2 or 3 times, at a salt concentration and temperature corresponding to 1×SSC, 0.1% SDS at 60° C.; 0.1×SSC, 0.1% SDS at 60° C.; or 0.1×SSC, 0.1% SDS at 68° C.

The probe may be, for example, a part of a sequence that is complementary to the gene as described above. Such a probe can be prepared by PCR using oligonucleotides prepared on the basis of the nucleotide sequences of known genes as primers and a DNA fragment containing any of these nucleotide sequences as a template. As the probe, for example, a DNA fragment having a length of about 300 bp can be used. In such a case, the washing conditions of the hybridization may be, for example, 50° C., 2×SSC and 0.1% SDS.

Furthermore, the wild-type phoS gene may have a nucleotide sequence corresponding to any of the nucleotide sequences of the wild-type phoS genes exemplified above or conservative variants thereof in which arbitrary codon(s) is/are replaced with respective equivalent codon(s). For example, the wild-type phoS gene may be a gene modified so that it has optimal codons according to codon frequencies in the chosen host.

The percentage of the sequence identity between two sequences can be determined by, for example, using a mathematical algorithm. Non-limiting examples of such a mathematical algorithm include the algorithm of Myers and Miller (1988) CABIOS 4:11-17, the local homology algorithm of Smith et al (1981) Adv. Appl. Math. 2:482, the homology alignment algorithm of Needleman and Wunsch (1970) J. Mol. Biol. 48:443-453, the method for searching homology of Pearson and Lipman (1988) Proc. Natl. Acad. Sci. 85:2444-2448, and an modified version of the algorithm of Karlin and Altschul (1990) Proc. Natl. Acad. Sci. USA 87:2264, such as that described in Karlin and Altschul (1993) Proc. Natl. Acad. Sci. USA 90:5873-5877.

By using a program based on such a mathematical algorithm, sequence comparison (i.e. alignment) for determining the sequence identity can be performed. The program can be appropriately executed by a computer. Examples of such a program can include, but are not limited to, CLUSTAL of PC/Gene program (available from Intelligenetics, Mountain View, Calif.), ALIGN program (Version 2.0), and GAP, BESTFIT, BLAST, FASTA, and TFASTA of Wisconsin Genetics Software Package, Version 8 (available from Genetics Computer Group (GCG), 575 Science Drive, Madison, Wis., USA). Alignment using these programs can be performed by using, for example, initial parameters. The CLUSTAL program is well described in Higgins et al. (1988) Gene 73:237-244 (1988), Higgins et al. (1989) CABIOS 5:151-153, Corpet et al. (1988) Nucleic Acids Res. 16:10881-90, Huang et al. (1992) CABIOS 8:155-65, and Pearson et al. (1994) Meth. Mol. Biol. 24:307-331.

In order to obtain a nucleotide sequence homologous to a target nucleotide sequence, in particular, for example, BLAST nucleotide search can be performed by using BLASTN program with score of 100 and word length of 12. In order to obtain an amino acid sequence homologous to a target protein, in particular, for example, a BLAST protein search can be performed by using the BLASTX program with score of 50 and word length of 3. See ncbi.nlm.nih.gov for BLAST nucleotide search and BLAST protein search. In addition, Gapped BLAST (BLAST 2.0) can be used in order to obtain an alignment including gap(s) for the purpose of comparison. In addition, PSI-BLAST can be used in order to perform repetitive search for detecting distant relationships between sequences. See Altschul et al. (1997) Nucleic Acids Res. 25:3389 for Gapped BLAST and PSI-BLAST. When using BLAST, Gapped BLAST, or PSI-BLAST, initial parameters of each program (e.g. BLASTN for nucleotide sequences, and BLASTX for amino acid sequences) can be used. Alignment can also be manually performed.

The sequence identity between two sequences can be calculated as the ratio of residues matching in the two sequences when aligning the two sequences so as to fit maximally with each other.

The above descriptions concerning variants of the genes and proteins can also be applied mutatis mutandis to arbitrary proteins such as PhoR protein, cell surface layer protein, Tat secretion system, and heterologous proteins to be produced by secretory production as described herein, and genes encoding them.

The mutant PhoS protein has the "specific mutation" in the amino acid sequence of such a wild-type PhoS protein as described above.

That is, in other words, the mutant PhoS protein may be identical to any of the wild-type PhoS proteins exemplified above or conservative variants thereof except that the mutant PhoS protein has the "specific mutation". Specifically, the mutant PhoS protein may be, for example, a protein having the amino acid sequence shown in SEQ ID NO: 4, 54, 55, 56, 57, or 58 except that the mutant PhoS protein has the "specific mutation". Specifically, the mutant PhoS protein may also be, for example, a protein having the amino acid sequence shown in SEQ ID NO: 4, 54, 55, 56, 57, or 58 but which can include substitution, deletion, insertion, or addition of one or several amino acid residues, except that the mutant PhoS protein has the "specific mutation". Specifically, the mutant PhoS protein may also be, for example, a protein having a homology of 80% or more, 90% or more, 95% or more, 97% or more, or 99% or more, to the amino acid sequence shown in SEQ ID NO: 4, 54, 55, 56, 57, or 58 except that the mutant PhoS protein has the "specific mutation".

Furthermore, in other words, the mutant PhoS protein may be a variant of any of the wild-type PhoS proteins exemplified above having the "specific mutation", and further including a conservative mutation at a site other than that of the "specific mutation". Specifically, the mutant PhoS protein may be, for example, a protein having the amino acid sequence shown in SEQ ID NO: 4, 54, 55, 56, 57, or 58 but having the "specific mutation", and further can include substitution, deletion, insertion, or addition of one or several amino acid residues at a site other than that of the "specific mutation".

The mutant phoS gene is not particularly limited so long as it encodes a mutant PhoS protein as described above.

Hereinafter, the "specific mutation" of the mutant PhoS protein will be explained.

The "specific mutation" is not particularly limited, so long as it results in a change in the amino acid sequence of a wild-type PhoS protein described above, and that it is effective for secretory production a heterologous protein.

The "specific mutation" can be one that results in improved secretory production of a heterologous protein. The expression "improved secretory production of a heterologous protein" can mean that a coryneform bacterium modified to have a mutant phoS gene, for example, a modified strain, is able to produce the heterologous protein by secretory production in an amount larger than that obtainable with a non-modified strain. The "non-modified strain" can refer to a control strain not having the "specific mutation" in the phoS gene, that is, a control strain not having any mutant phoS gene, and it may be, for example, a wild-type strain or a parent strain. Although the degree of increase meant by the expression "to produce a heterologous protein by secretory production in an amount larger than that obtainable with a non-modified strain" is not particularly limited so long as the secretory production amount of the heterologous protein is increased as compared with that obtainable with a non-modified strain, this expression may mean that the heterologous protein is produced by secretory production in an amount of, for example, 1.1 times or more, 1.2 times or more, 1.3 times or more, 2 times or more, or 5 times or more, of that obtainable with a non-modified strain, in terms of the accumulation amount in the medium and/or on the cell surface layer. In addition, the expression "to produce a heterologous protein by secretory production in an amount larger than that obtainable with a non-modified strain" may also mean that whereas the heterologous protein cannot be detected when a non-concentrated culture supernatant of a non-modified strain is applied to SDS-PAGE and stained with CBB, the heterologous protein can be detected when a non-concentrated culture supernatant of a modified strain is applied to SDS-PAGE and stained with CBB. Incidentally, the expression "to improve the secretory production amount of a heterologous protein" does not necessarily mean that the secretory production amount of every heterologous protein is improved, and it is sufficient that the secretory production amount of a heterologous protein chosen as the target of secretory production is improved. The expression "to improve the secretory production amount of a heterologous protein" may specifically mean, for example, that the secretory production amount of a heterologous protein described in the Example section, such as CspB50TEV-Teri, CspB6Xa-LFABP, CspB6TEV-ExCP, protransglutaminase fused with E. coli TorA signal sequence, protein glutaminase comprising a pro-structure moiety and fused with E. coli TorA signal sequence, or isomaltodextranase having a signal sequence, is improved.

Whether a certain mutation is a mutation that improves the secretory production amount of a heterologous protein can be confirmed by, for example, preparing a coryneform bacterial strain modified to have a gene encoding the PhoS protein having the certain mutation, quantifying the amount of the heterologous protein produced by secretory production when the strain is cultured in a medium, and comparing it with the amount of the heterologous protein produced by secretory production when a non-modified strain is cultured in the medium.

Preferred examples of a change of the amino acid sequence include substitution of an amino acid residue. That is, the "specific mutation" can be a mutation of replacing an amino acid residue with another amino acid residue. The amino acid residue substituted by the "specific mutation" may be one residue, or may be a combination of two or more residues. The amino acid residue substituted by the "specific mutation" may be an amino acid residue other than an autophosphorylated histidine residue. The amino acid residue substituted by the "specific mutation" may be an amino acid residue in the HisKA domain, other than an autophosphorylated histidine residue. The term "histidine residue that is autophosphorylated" or "autophosphorylated histidine residue" can refer to a histidine residue at position 276 of the wild-type PhoS protein. The term "HisKA domain" can refer to a region of amino acid residues at positions 266-330 of the wild-type PhoS protein. The amino acid residue substituted by the "specific mutation" may be the amino acid residue at position 302 of the wild-type PhoS protein, which can be a tryptophan residue (W302).

In the aforementioned mutation, examples of the amino acid residue after substitution include K(Lys), R(Arg), H(His), A(Ala), V(Val), L(Leu), I(Ile), G(Gly), S(Ser), T(Thr), P(Pro), F(Phe), W(Trp), Y(Tyr), C(Cys), M(Met), D(Asp), E(Glu), N(Asn), and Q(Gln), provided that the amino acid residue after substitution is other than the original one. As the amino acid residue after substitution, for example, one resulting in improvement in the secretory production amount of a heterologous protein can be chosen.

When substitution occurs at W302, examples of the amino acid residue after substitution include amino acid residues other than aromatic amino acid and histidine residues. Specific examples of the "amino acid residues other than aromatic amino acid and histidine residues" include K(Lys), R(Arg), A(Ala), V(Val), L(Leu), I(Ile), G(Gly), S(Ser), T(Thr), P(Pro), C(Cys), M(Met), D(Asp), E(Glu), N(Asn), and Q(Gln). More specific examples of the "amino acid residues other than aromatic amino acid and histidine residues" include K(Lys), A(Ala), V(Val), S(Ser), C(Cys), M(Met), D(Asp), and N(Asn).

Incidentally, the term "specific mutation" in reference to the phoS gene can refer to a mutation on the nucleotide sequence thereof that results in such a "specific mutation" as described above in the encoded PhoS protein.

The "amino acid residue at position X of the wild-type PhoS protein" can refer to an amino acid residue corresponding to the amino acid residue at position X in SEQ ID NO: 4. For example, "W302" can refer to an amino acid residue corresponding to the tryptophan residue at position 302 in SEQ ID NO: 4. The aforementioned positions of amino acid residues indicate relative positions, and the absolute positions thereof may shift due to deletion, insertion, addition, or the like of an amino acid residue or residues. For example, if one amino acid residue is deleted or inserted at a position on the N-terminal side of position X in the amino acid sequence shown as SEQ ID NO: 4, the amino acid residue originally at position X is relocated at position X−1 or X+1 counted from the N-terminus, however, it is still regarded as the "amino acid residue at position X of the wild-type PhoS protein". Specifically, for example, "W302" can refer to the tryptophan residue at positions 302, 302, 302, 321, 275, and 286, respectively, in the amino acid sequences of wild-type PhoS proteins shown in SEQ ID NOS: 4, 54, 55, 56, 57, and 58. Furthermore, the "histidine residue at position 276 of the wild-type PhoS protein (histidine residue that is autophosphorylated)" can refer to the histidine residue at positions 276, 276, 276, 295, 249, and 260, respectively, in the amino acid sequences of wild-type PhoS proteins shown in SEQ ID NOS: 4, 54, 55, 56, 57, and 58. Furthermore, the "region consisting of amino acid residues at positions 266-330 of the wild-type PhoS protein (HisKA domain)" can refer to the region consisting of amino acid residues at positions 266-330, 266-330, 266-330, 285-349, 239-303, and 250-314, respectively, in the amino acid sequences of wild-type PhoS proteins shown in SEQ ID NOS: 4, 54, 55, 56, 57, and 58.

Incidentally, while "W302" referred to herein is typically a tryptophan residue, it may also be other than a tryptophan residue. That is, when the wild-type PhoS protein has an amino acid sequence other than the amino acid sequences shown in SEQ ID NOS: 4, 54, 55, 56, 57, and 58, "W302" can be other than a tryptophan residue. Hence, for example, the "mutation replacing W302 with a cysteine residue" can include not only a mutation, when "W302" is a tryptophan residue, for replacing this tryptophan residue with a cysteine residue, but also includes a mutation, when "W302" is K(Lys), R(Arg), H(His), A(Ala), V(Val), L(Leu), I(Ile), G(Gly), S(Ser), T(Thr), P(Pro), F(Phe), Y(Tyr), M(Met), D(Asp), E(Glu), N(Asn), or Q(Gln), for replacing this residue with a cysteine residue. The same can be applied mutatis mutandis to the other mutations.

Which amino acid residue is the "amino acid residue corresponding to the amino acid residue at position X in SEQ ID NO: 4" in the amino acid sequence of an arbitrary PhoS protein can be determined by alignment between the amino acid sequence of the arbitrary PhoS protein and the amino acid sequence of SEQ ID NO: 4. The alignment can be performed by, for example, using known gene analysis software. Specific examples of such software include DNA-SIS produced by Hitachi Solutions, GENETYX produced by Genetyx, and so forth (Elizabeth C. Tyler et al., Computers and Biomedical Research, 24 (1) 72-96, 1991; Barton G J et al., Journal of Molecular Biology, 198 (2), 327-37, 1987).

The mutant phoS gene can be obtained by, for example, modifying a wild-type phoS gene so that the encoded PhoS protein has the aforementioned "specific mutation". The wild-type phoS gene to be modified can be obtained by, for example, cloning from an organism having the wild-type phoS gene, or chemical synthesis. Furthermore, the mutant phoS gene can also be obtained without using a wild-type phoS gene. For example, the mutant phoS gene may be directly obtained by chemical synthesis. The obtained mutant phoS gene may be further modified before use.

Genes can be modified by known methods. For example, an objective mutation can be introduced into a target site of DNA by the site-specific mutagenesis method. Examples of the site-specific mutagenesis method include a method of using PCR (Higuchi, R., 61, in PCR Technology, Erlich, H. A. Eds., Stockton Press (1989); Carter P., Meth. In Enzymol., 154, 382 (1987)), and a method of using a phage (Kramer, W. and Frits, H. J., Meth. in Enzymol., 154, 350 (1987); Kunkel, T. A. et al., Meth. in Enzymol., 154, 367 (1987)).

Hereinafter, methods for modifying a coryneform bacterium so as to have a mutant phoS gene are described.

A coryneform bacterium can be modified so as to have a mutant phoS gene by introducing the mutant phoS gene into the coryneform bacterium. A coryneform bacterium can be modified so as to have a mutant phoS gene also by introducing a mutation into the phoS gene onto the chromosome of the coryneform bacterium. A mutation can be introduced into a gene on a chromosome by natural mutation, mutagenesis treatment, or genetic engineering means.

Methods for introducing a mutant phoS gene into a coryneform bacterium are not particularly limited. It is sufficient that the mutant phoS gene is harbored by the bacterium so that it can be expressed under control of a promoter that functions in a coryneform bacterium. The promoter may be a promoter derived from or native to the host, or a heterogenous promoter. The promoter may be the native promoter for the phoS gene, or a promoter for another gene. In the bacterium, the mutant phoS gene may be present on a vector that autonomously replicates outside of the chromosome, such as plasmid, or may be incorporated into the chromosome. The bacterium may have only one copy of the mutant phoS gene, or two or more copies of the mutant phoS gene. The bacterium may have only one kind of mutant phoS gene, or two or more kinds of mutant phoS genes. The mutant phoS gene can be introduced, for example, in the same manner as that for introduction of a gene in methods for increasing the expression of a gene described below, or for introduction of the genetic construct described below.

The bacterium may or may not have the wild-type phoS gene. It is preferred that the bacterium does not have the wild-type phoS gene.

A coryneform bacterium not having the wild-type phoS gene can be obtained by disrupting the wild-type phoS gene on the chromosome. The wild-type phoS gene can be disrupted by known methods. Specifically, the wild-type phoS gene can be disrupted by, for example, deleting a part or the whole of the promoter region and/or the coding region of the wild-type phoS gene.

Furthermore, by replacing the wild-type phoS gene on the chromosome with a mutant phoS gene, a coryneform bacterium modified so that it does not have the wild-type phoS gene and has the mutant phoS gene can be obtained. Examples of methods for performing such gene substitution include, for example, a method of using a linear DNA such as a method called "Red driven integration" (Datsenko, K. A, and Wanner, B. L., Proc. Natl. Acad. Sci. USA, 97:6640-6645 (2000)), a method of utilizing the Red driven integration in combination with an excision system derived from λ phage (Cho, E. H., Gumport, R. I., Gardner, J. F., J. Bacteriol., 184:5200-5203 (2002)) (refer to WO2005/010175), a method of using a plasmid including a temperature sensitive replication origin, a method of using a plasmid capable of conjugative transfer, a method of utilizing a suicide vector not including a replication origin that functions in a host (U.S. Pat. No. 6,303,383, Japanese Patent Laid-open (Kokai) No. 05-007491), and so forth.

The PhoS protein functions, that is, induces a response against phosphate depletion in the environment, in combination with a response regulator PhoR protein. Hence, the bacterium has a phoR gene so that the mutant PhoS protein is able to function normally. The phoR gene is a gene encoding a PhoR protein, which is a response regulator of the PhoRS system. The expression "to have a phoR gene" can also be referred to as "to have a PhoR protein". Typically, it is sufficient that the PhoR protein inherently possessed by the bacterium functions in combination with the mutant PhoS protein. Alternatively, the bacterium may be introduced with an appropriate phoR gene, in addition to or instead of the phoR gene inherently possessed by the bacterium. The phoR gene to be introduced is not particularly limited, as long as it encodes a PhoR protein that functions in combination with the mutant PhoS protein.

Examples of the phoR gene include, for example, phoR genes of coryneform bacteria. Specific examples of the phoR genes of coryneform bacteria can include, for example, the phoR genes of *C. glutamicum* YDK010, *C. glutamicum* ATCC 13032, *C. glutamicum* ATCC 14067, *C. callunae*, *C. crenatum*, and *C. efficiens*. The nucleotide sequence of the phoR gene of *C. glutamicum* ATCC 13032 and the amino acid sequence of the PhoR protein of the same are shown as SEQ ID NO: 96 and 97, respectively.

The phoR gene may be a variant of any of the phoR genes exemplified above, so long as the original function thereof is maintained. Similarly, the PhoR protein may be a variant of any of the PhoR proteins exemplified above, so long as the original function thereof is maintained. That is, the term "phoR gene" can include not only the phoR genes exemplified above, but also can include conservative variants thereof. Similarly, the term "PhoR protein" can include not only the PhoR proteins exemplified above, but also can include conservative variants thereof. The above descriptions concerning conservative variants of the phoS gene and PhoS protein can be applied mutatis mutandis to variants of the phoR gene and PhoR protein. For example, the phoR gene may be a gene encoding a protein having the aforementioned amino acid sequence, but which can include substitution, deletion, insertion, or addition of one or several amino acid residues at one or several positions, so long as the gene encodes a protein of which the original function is maintained. Incidentally, the expression "the original function is maintained" used for the PhoR protein may mean that a variant of the protein has a function as a response regulator of the PhoRS system. The term "function as a response regulator of the PhoRS system" may specifically refer to a function of inducing a response against phosphate depletion in the environment in combination with a sensor kinase PhoS protein. The term "function as a response regulator of the PhoRS system" may more specifically refer to a function of being activated via transfer of phosphate group from the PhoS protein that sensed phosphate depletion in the environment to be autophosphorylated, and regulating the expression of genes that respond to phosphate depletion in the environment.

Whether or not a variant of the PhoR protein has a function as a response regulator of the PhoRS system can be confirmed by, for example, introducing a gene encoding the variant into a phoR-gene-deletion strain of a coryneform bacterium, and confirming whether or not responsiveness against phosphate depletion is complemented. Complementation of responsiveness against phosphate depletion can be detected, for example, as improvement of growth under phosphate depletion conditions, or as induction of the expression of genes of which the expression is known to be induced under phosphate depletion conditions (J. Bacteriol., 188, 724-732(2006)). As the phoR-gene-deletion strain of a coryneform bacterium, for example, a phoR-gene-deletion strain of *C. glutamicum* YDK010 or a phoR-gene-deletion strain of *C. glutamicum* ATCC13032 can be used.

<1-1-3> Reduction in Activity of Cell Surface Layer Protein

The bacterium may be a bacterium in which the activity(s) of cell surface layer protein(s) is/are reduced. Hereinafter, the cell surface layer proteins and genes encoding them will be described.

The cell surface layer protein is a protein that makes up the surface layer (S layer) of bacteria or archaea. Examples of cell surface layer proteins of coryneform bacteria include PS1 and PS2 (CspB) of *C. glutamicum* (Japanese Patent Laid-open (Kohyo) No. 6-502548), and SlpA (CspA) of *C. stationis* (Japanese Patent Laid-open (Kokai) No. 10-108675). It is preferable to reduce the activity of the PS2 protein.

The nucleotide sequence of the cspB gene of *C. glutamicum* ATCC 13869 and the amino acid sequence of the PS2 protein (CspB protein) encoded by the gene are shown in SEQ ID NOS: 67 and 68, respectively.

Furthermore, for example, the amino acid sequences of CspB homologues have been reported for 28 strains of *C. glutamicum* (J. Biotechnol., 112, 177-193 (2004)). These 28 strains of *C. glutamicum* and the GenBank accession numbers of the cspB gene homologues in NCBI database are as follows: (the GenBank accession numbers are shown in the parentheses).

*C. glutamicum* ATCC 13058 (AY524990)
*C. glutamicum* ATCC 13744 (AY524991)
*C. glutamicum* ATCC 13745 (AY524992)
*C. glutamicum* ATCC 14017 (AY524993)
*C. glutamicum* ATCC 14020 (AY525009)
*C. glutamicum* ATCC 14067 (AY524994)
*C. glutamicum* ATCC 14068 (AY525010)
*C. glutamicum* ATCC 14747 (AY525011)
*C. glutamicum* ATCC 14751 (AY524995)
*C. glutamicum* ATCC 14752 (AY524996)
*C. glutamicum* ATCC 14915 (AY524997)
*C. glutamicum* ATCC 15243 (AY524998)
*C. glutamicum* ATCC 15354 (AY524999)
*C. glutamicum* ATCC 17965 (AY525000)
*C. glutamicum* ATCC 17966 (AY525001)
*C. glutamicum* ATCC 19223 (AY525002)
*C. glutamicum* ATCC 19240 (AY525012)
*C. glutamicum* ATCC 21341 (AY525003)
*C. glutamicum* ATCC 21645 (AY525004)
*C. glutamicum* ATCC 31808 (AY525013)
*C. glutamicum* ATCC 31830 (AY525007)
*C. glutamicum* ATCC 31832 (AY525008)
*C. glutamicum* LP-6 (AY525014)
*C. glutamicum* DSM20137 (AY525015)
*C. glutamicum* DSM20598 (AY525016)
*C. glutamicum* DSM46307 (AY525017)
*C. glutamicum* 22220 (AY525005)
*C. glutamicum* 22243 (AY525006)

Since the nucleotide sequence of a gene encoding a cell surface layer protein may differ depending on species or strain to which the coryneform bacterium belongs, the gene encoding a cell surface layer protein may be a variant of any of the genes encoding the cell surface layer proteins exemplified above, so long as the original function thereof is maintained. Similarly, the cell surface layer protein may be a variant of any of the cell surface layer proteins exemplified above, so long as the original function thereof is maintained. That is, the term "cspB gene" can include not only the cspB genes exemplified above, but also can include conservative variants thereof. Similarly, the term "CspB protein" can include not only the CspB proteins exemplified above, but also can include conservative variants thereof. The above descriptions concerning conservative variants of the phoS gene and PhoS protein can be applied mutatis mutandis to variants of the cell surface layer protein and the gene encoding it. For example, the gene encoding the cell surface layer protein may be a gene encoding a protein having the aforementioned amino acid sequence, but which can include substitution, deletion, insertion, or addition of one or several amino acid residues at one or several positions, so long as the gene encodes a protein of which the original function is maintained. Incidentally, the expression "original function is maintained" in reference to the cell surface layer protein may mean that if the activity of the protein is reduced in a coryneform bacterium, the secretory production amount of a heterologous protein is increased compared with that obtainable with a non-modified strain.

The phrase "if the activity of the protein is reduced in a coryneform bacterium, the secretory production amount of a heterologous protein is increased compared with that obtainable with a non-modified strain" can refer to a property that imparts an ability to produce a heterologous protein by secretory production in an amount larger than that obtainable with a non-modified strain to a coryneform bacterium when the activity thereof is reduced in the coryneform bacterium. The "non-modified strain" can refer to a control strain of which the activity(s) of cell surface layer protein(s) is/are not reduced, and it may be, for example, a wild-type strain or a parent strain. Although the degree of increase meant by the expression "to produce a heterologous protein by secretory production in an amount larger than that obtainable with a non-modified strain" is not particularly limited so long as the secretory production amount of the heterologous protein is increased as compared with that obtainable with a non-modified strain, it may mean that the heterologous protein is produced by secretory production in an amount of, for example, 1.1 times or more, 1.2 times or more, 1.3 times or more, 2 times or more, of that obtainable with a non-modified strain, in terms of the accumulation amount in the medium and/or on the cell surface layer. In addition, the expression "to produce a heterologous protein by secretory production in an amount larger than that obtainable with a non-modified strain" may also mean that whereas the heterologous protein cannot be detected when a non-concentrated culture supernatant of a non-modified strain is applied to SDS-PAGE and stained with CBB, the heterologous protein can be detected when a non-concentrated culture supernatant of a modified strain is applied to SDS-PAGE and stained with CBB.

Whether a protein has a property that if the activity of the protein is reduced in a coryneform bacterium, the secretory production amount of a heterologous protein is increased compared with that obtainable with a non-modified strain can be confirmed by preparing a coryneform bacterial strain that is modified so that the activity of the protein is reduced, quantifying the secretory production amount of the heterologous protein when the modified strain is cultured in a medium, and comparing the quantified amount with the secretory production amount of the heterologous protein when the strain before being modified (un-modified strain) is cultured in the medium.

The expression "activity of a cell surface layer protein is reduced" can include when a coryneform bacterium has been modified so that the activity of a cell surface layer protein is reduced, and when the activity of a cell surface layer protein is inherently reduced in a coryneform bacterium. The phrase "activity of a cell surface layer protein is inherently reduced in a coryneform bacterium" can include when a coryneform bacterium is inherently deficient in a cell surface layer protein. That is, examples of a coryneform bacterium in which the activity of a cell surface layer protein is reduced include a coryneform bacterium that is inherently deficient in a cell surface layer protein. Examples of "a coryneform bacterium is inherently deficient in a cell surface layer protein" can include when a coryneform bacterium is inherently deficient in the gene encoding a cell surface layer protein. The expression "a coryneform bacterium is inherently deficient in a cell surface layer protein" may mean that a coryneform bacterium is inherently deficient in one or more of the cell surface layer protein(s) found in other strain(s) of the species to which the coryneform bacterium belongs. For example, the phrase "C. glutamicum is inherently deficient in a cell surface layer protein" may mean that a C. glutamicum strain is inherently deficient in one or more cell surface layer protein(s) found in other C. glutamicum strain(s), for example, deficient in PS1 and/or PS2 (CspB). Examples of the coryneform bacterium that is inherently deficient in a cell surface layer protein include C. glutamicum ATCC 13032, which is inherently deficient in the cspB gene.

Hereinafter, methods for reducing the activity of a protein such as cell surface layer proteins will be explained. The methods for reducing the activity of a protein described below can be utilized for disruption of the wild-type phoS gene.

The expression "the activity of a protein is reduced" can mean that the activity of the protein per cell is reduced as compared with that of a non-modified strain. The term "non-modified strain" can refer to a control strain that has not been modified so that the activity of an objective protein is reduced. Examples of the non-modified strain can include a wild-type strain and parent strain. The phrase "the activity of a protein is reduced" can also include when the activity of the protein has completely disappeared. Specifically, the expression "the activity of a protein is reduced" can mean that the number of molecules of the protein per cell is reduced, and/or the function of each molecule of the protein is reduced as compared with those of a non-modified strain. That is, the term "activity" in the expression "the activity of a protein is reduced" is not limited to the catalytic activity of the protein, but may also mean the transcription amount of a gene, that is, the amount of mRNA, encoding the protein or the translation amount of the protein, that is, the amount of the protein. The phrase "the number of molecules of the protein per cell is reduced" can also include when the protein does not exist at all. The phrase "the function of each molecule of the protein is reduced" can also include when the function of each protein molecule has completely disappeared. The degree of the reduction in the activity of a protein is not particularly limited, so long as the activity is reduced as compared with that of a non-modified strain. The activity of a protein may be reduced to, for example, 50% or less, 20% or less, 10% or less, 5% or less, or 0% of that of a non-modified strain.

The modification for reducing the activity of a protein can be attained by, for example, reducing the expression of a gene encoding the protein. The phrase "the expression of a gene is reduced" can mean that the expression of the gene per cell is reduced as compared with that of a non-modified strain such as a wild-type strain or a parent strain. The phrase "the expression of a gene is reduced" may specifically mean that the transcription amount of the gene (i.e. the amount of mRNA) is reduced, and/or the translation amount of the gene (i.e. the amount of the protein expressed from the gene) is reduced. The phrase "the expression of a gene is reduced" can also include when the gene is not expressed at all. The phrase "the expression of a gene is reduced" can also be referred to as "the expression of a gene is attenuated". The expression of a gene may be reduced to, for example, 50% or less, 20% or less, 10% or less, 5% or less, or 0% of that of a non-modified strain.

The reduction in gene expression may be due to, for example, a reduction in the transcription efficiency, a reduction in the translation efficiency, or a combination of these. The expression of a gene can be reduced by modifying an expression control sequence of the gene such as promoter, Shine-Dalgarno (SD) sequence (also referred to as ribosome-binding site (RBS)), and spacer region between RBS and the start codon of the gene. When an expression control sequence is modified, one or more nucleotides, two or more nucleotides, or three or more nucleotides, of the expression control sequence can be modified. Furthermore, the entire or just a portion of an expression control sequence may be deleted. The expression of a gene can also be reduced by, example, manipulating a factor responsible for expression control. Examples of the factor responsible for expression control can include low molecules responsible for transcription or translation control (inducers, inhibitors, etc.), proteins responsible for transcription or translation control (transcription factors etc.), nucleic acids responsible for transcription or translation control (siRNA etc.), and so forth. Furthermore, the expression of a gene can also be reduced by, for example, introducing a mutation that reduces the expression of the gene into the coding region of the gene. For example, the expression of a gene can be reduced by replacing a codon in the coding region of the gene with a synonymous codon used less frequently in a host. Furthermore, for example, the gene expression may be reduced due to disruption of a gene as described herein.

The modification for reducing the activity of a protein can also be attained by, for example, disrupting a gene encoding the protein. The expression "a gene is disrupted" can mean that a gene is modified so that a protein that functions normally is not produced. The phrase "a protein that functions normally is not produced" can include when the protein is not produced at all from the gene, and also when the protein produced from the gene has reduced or no function (such as activity or property) per molecule.

Disruption of a gene can be attained by, for example, deleting the entire or only a portion of the gene's coding region on the chromosome. Furthermore, the entire gene including sequences upstream and downstream from the gene on the chromosome may be deleted. The region to be deleted may be any region, such as an N-terminus region, an internal region, or a C-terminus region, so long as the activity of the protein is reduced. Deletion of a longer region will usually more surely inactivate the gene. Furthermore, it is preferred that reading frames of the sequences upstream and downstream from the region to be deleted are not the same.

Disruption of a gene can also be attained by, for example, introducing a mutation for an amino acid substitution (missense mutation), a stop codon (nonsense mutation), a frame shift mutation which adds or deletes one or two nucleotide residues, or the like into the coding region of the gene on a chromosome (Journal of Biological Chemistry, 272:8611-8617 (1997); Proceedings of the National Academy of Sciences, USA, 95 5511-5515 (1998); Journal of Biological Chemistry, 26 116, 20833-20839 (1991)).

Disruption of a gene can also be attained by, for example, inserting another sequence into a coding region of the gene on a chromosome. Site of the insertion may be in any region of the gene, and insertion of a longer region can usually more surely inactivate the gene. It is preferred that reading frames of the sequences upstream and downstream from the insertion site are not the same. The other sequence is not particularly limited so long as the chosen sequence reduces or eliminates the activity of the encoded protein, and examples thereof include, for example, a marker gene such as antibiotic resistance genes, and a gene useful for production of an objective substance.

Such modification of a gene on a chromosome as described above can be attained by, for example, preparing a deficient-type gene modified so that it is unable to produce a protein that functions normally, and transforming a host with a recombinant DNA containing the deficient-type gene to induce homologous recombination between the deficient-type gene and the wild-type gene on a chromosome and thereby substitute the deficient-type gene for the wild-type gene on the chromosome. In this procedure, if a marker gene selected according to the characteristics of the host such as auxotrophy is included in the recombinant DNA, the operation is easier. Examples of the deficient-type gene include a gene with deletion of all or a part of the gene, gene including a missense mutation, gene including insertion of a transposon or marker gene, gene including a nonsense mutation, and gene including a frame shift mutation. The structure of the recombinant DNA chosen for homologous recombination is not particularly limited as long as it induces homologous recombination in a desired manner. For example, a host can be transformed with a linear DNA containing the deficient-type gene and also containing upstream and downstream sequences of the wild-type gene on the chromosome at the respective ends, so that homologous recombination occurs at each of the upstream and downstream sides of the wild-type gene, to thereby replace the wild-type gene with the deficient-type gene in one step. The protein encoded by the deficient-type gene has a conformation different from that of the wild-type protein, even if it is produced, and thus the function thereof is reduced or eliminated. Such gene disruption based on gene substitution utilizing homologous recombination has already been reported, and there are also known methods of using a linear DNA such as a method called "Red driven integration" (Datsenko, K. A, and Wanner, B. L., Proc. Natl. Acad. Sci. USA, 97:6640-6645 (2000)), and a method utilizing the Red driven integration in combination with an excision system derived from λ phage (Cho, E. H., Gumport, R. I., Gardner, J. F., J. Bacteriol., 184:5200-5203 (2002)) (refer to WO2005/010175), a method of using a plasmid having a temperature sensitive replication origin, a method of using a plasmid capable of conjugative transfer, a method of utilizing a suicide vector not having a replication origin that functions in a host (U.S. Pat. No. 6,303,383, Japanese Patent Laid-open (Kokai) No. 05-007491), and so forth.

The modification for reducing activity of a protein can also be attained by, for example, a mutagenesis treatment. Examples of the mutagenesis treatment include irradiation of X-ray or ultraviolet and treatment with a mutation agent such as N-methyl-N'-nitro-N-nitrosoguanidine (MNNG), ethyl methanesulfonate (EMS), and methyl methanesulfonate (MMS).

A reduction in the activity of a protein can be confirmed by measuring the activity of the protein.

A reduction in the activity of a protein can also be confirmed by confirming a reduction in the expression of a gene encoding the protein. A reduction in the expression of a gene can be confirmed by confirming a reduction in the transcription amount of the gene or a reduction in the amount of the protein expressed from the gene.

A reduction in the transcription amount of a gene can be confirmed by comparing the amount of mRNA transcribed from the gene with that of a non-modified strain. Examples of the method for evaluating the amount of mRNA include Northern hybridization, RT-PCR, and so forth (Molecular Cloning, Cold Spring Harbor Laboratory Press, Cold Spring Harbor (USA), 2001). The amount of mRNA can be reduced to, for example, 50% or less, 20% or less, 10% or less, 5% or less, or 0% of that of a non-modified strain.

A reduction in the amount of a protein can be confirmed by performing SDS-PAGE and confirming the intensity of the separated protein band. A reduction in the amount of a protein can be confirmed by Western blotting using antibodies (Molecular Cloning, Cold Spring Harbor Laboratory Press, Cold Spring Harbor (USA) 2001). The amount of the protein is reduced to, for example, 50% or less, 20% or less, 10% or less, 5% or less, or 0% of that of a non-modified strain.

Disruption of a gene can be confirmed by determining the nucleotide sequence of a part or the whole of the gene, restriction enzyme map, full length, or the like of the gene depending on the means used for the disruption.

<1-1-4> Protein Secretion System

The bacterium as described herein has a protein secretion system. The protein secretion system is not particularly limited, so long as it can secrete an objective heterologous protein. Examples of the protein secretion system can include the Sec system (Sec secretion system) and Tat system (Tat secretion system). The bacterium may have been modified so that the protein secretion system is enhanced. For example, the bacterium may have been modified so that the expression of one or more genes encoding the Tat secretion system is/are increased. Such a modification can also be referred to as "enhancement of the Tat secretion system". Enhancement of the Tat secretion system is preferable particularly when producing a heterologous protein by secretory production using a Tat-dependent signal peptide. Methods for increasing the expression of genes encoding the Tat secretion system are described in Japanese Patent No. 4730302.

Examples of the genes encoding the Tat secretion system can include tatA, tatB, and tatC genes of *C. glutamicum*. The tatA, tatB, and tatC genes of *C. glutamicum* ATCC 13032 correspond to the complementary sequence of positions 1571065-1571382, the sequence of positions 1167110-1167580, and the complementary sequence of positions 1569929-1570873 in the genome sequence registered as GenBank accession NC_003450 (VERSION NC_003450.3 GI:58036263) in NCBI database, respectively. The TatA, TatB, and TatC proteins of *C. glutamicum* ATCC 13032 are registered as GenBank accession NP_600707 (version NP_600707.1 GI:19552705, locus_tag="NCgl1434"), GenBank accession NP_600350 (version NP_600350.1 GI:19552348, locus_tag="NCgl1077"), and GenBank accession NP_600706 (version NP_600706.1 GI:19552704, locus_tag="NCgl1433"), respectively. The nucleotide sequences of the tatA, tatB, and tatC genes of *C. glutamicum* ATCC 13032 and the amino acid sequences of the TatA, TatB, and TatC proteins of the same are shown as SEQ ID NOS: 69-74.

Examples of the genes encoding the Tat secretion system can also include tatA, tatB, tatC, and tatE genes of *E. coli*. The tatA, tatB, tatC, and tatE genes of *E. coli* K-12 MG1655 correspond to the sequence of positions 4019968-4020237, the sequence of positions 4020241-4020756, the sequence of positions 4020759-4021535, and the sequence of positions 658170-658373 in the genome sequence registered as GenBank accession NC_000913(VERSION NC_000913.2 GI:49175990) in NCBI database, respectively. The TatA, TatB, TatC, and TatE proteins of *E. coli* K-12 MG1655 have been registered as GenBank accession NP_418280 (version NP_418280.4 GI:90111653, locus_tag="b3836"), GenBank accession YP_026270 (version YP_026270.1 GI:49176428, locus_tag="b3838"), GenBank accession NP_418282 (version NP_418282.1 GI:16131687, locus_tag="b3839"), and GenBank accession NP_415160 (version NP_415160.1 GI:16128610, locus_tag="b0627"), respectively.

The gene encoding the Tat secretion system may be a variant of any of the genes encoding the Tat-secretion-system exemplified above, so long as the original function thereof is maintained. Similarly, the Tat-secretion-system may be a variant of any of the Tat-secretion-systems exemplified above, so long as the original function thereof is maintained. That is, the terms "tatA gene", "tatB gene", "tatC gene", and "tatE gene" can include not only the tatA, tatB, tatC, and tatE genes exemplified above, respectively, but also can include conservative variants thereof. Similarly, the terms "TatA protein", "TatB protein", "TatC protein", and "TatE protein" can include not only the TatA, TatB, TatC, and TatE proteins exemplified above, respectively, but also includes conservative variants thereof. The above descriptions concerning conservative variants of the phoS gene and PhoS protein can be applied mutatis mutandis to variants of the Tat-secretion-system and the gene encoding it. For example, the gene encoding the Tat-secretion-system may be a gene encoding a protein having any of the aforementioned amino acid sequences, but which can include substitution, deletion, insertion, or addition of one or several amino acid residues at one or several positions, so long as the gene encodes a protein of which the original function is maintained. Incidentally, the expression "original function is maintained" in reference to the Tat-secretion-system may mean that the system is able to secrete a protein fused with a Tat-dependent signal peptide at the N-terminus out of the cell.

Hereinafter, methods for increasing the expression of a gene such as genes encoding the Tat secretion system will be described.

The phrase "the expression of a gene is increased" can mean that the expression of the gene is increased as compared with that of a non-modified strain. The term "non-modified strain" can refer to a control strain that has not been modified so that the expression of an objective gene is increased. Examples of the non-modified strain can include a wild-type strain and parent strain. The phrase "the expression of a gene is increased" may specifically mean that the transcription amount of the gene (i.e. the amount of mRNA) is increased, and/or the translation amount of the gene (i.e. the amount of the protein expressed from the gene) is increased. The phrase "the expression of a gene is increased" may also be referred to as "the expression of a gene is enhanced". The degree of the increase in the expression of a gene is not limited, so long as the expression of the gene is increased as compared with that of a non-modified strain. The expression of a gene may be increased 1.5 times or more, 2 times or more, or 3 times or more, of that of a non-modified strain. Furthermore, the state that "the expression of a gene is increased" can include not only when the expression amount of an objective gene is increased in a strain that inherently expresses the objective gene, but also when the gene is introduced into a strain that does not inherently express the objective gene, and expressed therein. That is, the phrase "the expression of a gene is increased" may also mean, for example, that an objective gene is introduced into a strain that does not possess the gene, and is expressed therein.

The expression of a gene can be increased by, for example, increasing the copy number of the gene.

The copy number of a gene can be increased by introducing the gene into the chromosome of a host. A gene can be introduced into a chromosome by, for example, using homologous recombination (Miller, J. H., Experiments in Molecular Genetics, 1972, Cold Spring Harbor Laboratory). Examples of the gene transfer method utilizing homologous recombination include, for example, a method using a linear DNA such as Red-driven integration (Datsenko, K. A., and Wanner, B. L., Proc. Natl. Acad. Sci. USA, 97:6640-6645 (2000)), a method of using a plasmid containing a temperature sensitive replication origin, a method of using a plasmid capable of conjugative transfer, a method of using a suicide vector not having a replication origin that functions in a host, or a transduction method using a phage. The structure of the recombinant DNA to be used for homologous recombination is not particularly limited as long as it causes homologous recombination in a desired manner. For example, a host can be transformed with a linear DNA containing an objective gene and also containing upstream and downstream sequences of the homologous recombination target region on the chromosome at the respective ends, so that homologous recombination occurs at each of upstream and downstream sides of the target region, to thereby replace the target region with the arbitrary sequence. The recombinant DNA chosen for homologous recombination may contain a marker gene for selection of transformants. Only one copy of, or two or more copies of a gene may be introduced. For example, by performing homologous recombination using a sequence which is present in multiple copies on a chromosome as a target, multiple copies of a gene can be introduced into the chromosome. Examples of such a sequence which is present in multiple copies on a chromosome include repetitive DNAs, and inverted repeats located at the both ends of a transposon. Alternatively, homologous recombination may be performed by using an appropriate sequence on a chromosome such as a gene unnecessary for the production of an objective substance as a target. Furthermore, a gene can also be randomly introduced into a chromosome by using a transposon or Mini-Mu (Japanese Patent Laid-open (Kokai) No. 2-109985, U.S. Pat. No. 5,882,888, EP 805867 B1). As the transposon, an artificial transposon may also be used (Japanese Patent Laid-open (Kokai) No. 9-70291).

Introduction of a target gene into a chromosome can be confirmed by Southern hybridization using a probe having a sequence complementary to the whole gene or a part thereof, PCR using primers prepared on the basis of the sequence of the gene, or the like.

Furthermore, the copy number of a gene can also be increased by introducing a vector containing the gene into a host. For example, the copy number of a target gene can be increased by ligating a DNA fragment containing the target gene with a vector that functions in a host to construct an expression vector of the gene, and transforming the host with the expression vector. The DNA fragment containing the target gene can be obtained by, for example, PCR using the genomic DNA of a microorganism having the target gene as the template. As the vector, a vector autonomously replicable in the cell of the host can be used. The vector can be a multi-copy vector. Furthermore, the vector can have a marker such as an antibiotic resistance gene for selection of transformant. Furthermore, the vector may have a promoter and/or terminator for expressing the introduced gene. The vector may be, for example, a vector derived from a bacterial plasmid, a vector derived from a yeast plasmid, a vector derived from a bacteriophage, cosmid, phagemid, or the like. Specific examples of vector autonomously replicable in coryneform bacteria include pHM1519 (Agric. Biol. Chem., 48, 2901-2903 (1984)); pAM330 (Agric. Biol. Chem., 48, 2901-2903 (1984)); plasmids obtained by improving these and having a drug resistance gene; plasmid pCRY30 described in Japanese Patent Laid-open (Kokai) No. 3-210184; plasmids pCRY21, pCRY2KE, pCRY2KX, pCRY31, pCRY3KE, and pCRY3KX described in Japanese Patent Laid-open (Kokai) No. 2-72876 and U.S. Pat. No. 5,185,262; plasmids pCRY2 and pCRY3 described in Japanese Patent Laid-open (Kokai) No. 1-191686; pAJ655, pAJ611, and pAJ1844 described in Japanese Patent Laid-open (Kokai) No. 58-192900; pCG1 described in Japanese Patent Laid-open (Kokai) No. 57-134500; pCG2 described in Japanese Patent Laid-open (Kokai) No. 58-35197; pCG4 and pCG11 described in Japanese Patent Laid-open (Kokai) No. 57-183799; pVK7 described in Japanese Patent Laid-open (Kokai) No. 10-215883; and pVC7 described in Japanese Patent Laid-open (Kokai) No. 9-070291.

When a gene is introduced, it is sufficient that the gene is able to be by the bacterium. Specifically, it is sufficient that the gene is introduced so that it is expressed under control by a promoter sequence that functions in the bacterium. The promoter may be a promoter native to the host, or may be a heterogenous promoter. The promoter may be the native promoter of the gene to be introduced, or a promoter of another gene. As the promoter, such a promoter as mentioned later which functions in a coryneform bacterium can be used.

A terminator for terminating the gene transcription can be provided downstream of the gene. The terminator is not particularly limited so long as it functions in the bacterium. The terminator may be native to the host, or may be a heterogenous terminator. The terminator may be the native terminator of the gene to be introduced, or may be a terminator of another gene.

Vectors, promoters, and terminators available in various microorganisms are disclosed in detail in "Fundamental Microbiology Vol. 8, Genetic Engineering, KYORITSU SHUPPAN CO., LTD, 1987", and those can be used.

Furthermore, when two or more of genes are introduced, it is sufficient that the genes are each able to be expressed by the bacterium. For example, all the genes may be on a single expression vector or a chromosome. Furthermore, the genes may be on two or more expression vectors, or on a single or two or more expression vectors and a chromosome. An operon made up of two or more genes may also be introduced.

The gene to be introduced is not particularly limited so long as it codes for a protein that functions in the chosen host. The gene to be introduced may be a gene native to the host, or may be a heterogenous gene. The gene to be introduced can be obtained by, for example, PCR using primers designed on the basis of the nucleotide sequence of the gene, and using the genomic DNA of an organism having the gene, a plasmid carrying the gene, or the like as the template. The gene to be introduced may also be totally synthesized, for example, on the basis of the nucleotide sequence of the gene (Gene, 60(1), 115-127 (1987)). The obtained gene can be used as it is, or after being modified as required.

Furthermore, the expression of a gene can be increased by improving the transcription efficiency of the gene. In addition, the expression of a gene can also be increased by improving the translation efficiency of the gene. The transcription efficiency of the gene and the translation efficiency of the gene can be improved by, for example, modifying an expression control sequence of the gene. The term "expression control sequence" collectively can refer to sites that affect the expression of a gene. Examples of the expression control sequence can include, for example, promoter, Shine-Dalgarno (SD) sequence (also referred to as ribosome binding site (RBS)), and spacer region between RBS and the start codon. Expression control sequences can be identified by using a promoter search vector or gene analysis software such as GENETYX. These expression control sequences can be modified by, for example, homologous recombination. Examples of methods for modification using homologous recombination include a method of using a temperature sensitive vector, or the Red driven integration method (WO2005/010175).

The transcription efficiency of a gene can be improved by, for example, replacing the promoter of the gene on a chromosome with a stronger promoter. The "stronger promoter" can mean a promoter that induces improved transcription of a gene as compared with an inherent wild-type promoter of the gene. Examples of strong promoters that function in coryneform bacteria can include the artificially modified P54-6 promoter (Appl. Microbiol. Biotechnol., 53, 674-679 (2000)), pta, aceA, aceB, adh, and amyE promoters inducible in coryneform bacteria with acetic acid, ethanol, pyruvic acid, or the like, cspB, SOD, and tuf (EF-Tu) promoters, which are strong promoters capable of providing a large expression amount in coryneform bacteria (Journal of Biotechnology, 104 (2003) 311-323; Appl. Environ. Microbiol., 2005 December; 71 (12):8587-96), as well as lac promoter, tac promoter, and trc promoter. Furthermore, as the stronger promoter, a highly-active type of an existing promoter may also be obtained by using various reporter genes. For example, by making the −35 and −10 regions in a promoter region closer to the consensus sequence, the activity of the promoter can be enhanced (WO00/18935). Methods for evaluating the strength of promoters and examples of strong promoters are described in the paper of Goldstein et al. (Prokaryotic Promoters in Biotechnology, Biotechnol. Annu. Rev., 1, 105-128 (1995)), and so forth.

The translation efficiency of a gene can be improved by, for example, replacing the Shine-Dalgarno (SD) sequence (also referred to as ribosome binding site (RBS)) for the gene on a chromosome with a stronger SD sequence. The "stronger SD sequence" can mean a SD sequence that provides an improved translation of mRNA compared with an inherent wild-type SD sequence of the gene. Examples of stronger SD sequences include, for example, RBS of the gene 10 derived from phage T7 (Olins P. O. et al, Gene, 1988, 73, 227-235). Furthermore, it is known that substitution, insertion, or deletion of several nucleotides in a spacer region between RBS and the start codon, especially in a sequence immediately upstream of the start codon (5'-UTR), can significantly affect the stability and translation efficiency of mRNA, and hence, the translation efficiency of a gene can also be improved by modifying them.

The translation efficiency of a gene can also be improved by, for example, modifying codons. For example, the translation efficiency of a gene can be improved by replacing a rare codon present in the gene with a synonymous codon that is more frequently used. That is, the gene to be introduced may be modified, for example, so as to contain optimal codons according to the frequencies of codons observed in the chosen host. Codons can be replaced by, for example, the site-specific mutation method for introducing an objective mutation into an objective site of DNA. Examples of the site-specific mutation method include the method utilizing PCR (Higuchi, R., 61, in PCR Technology, Erlich, H.A. Eds., Stockton Press (1989); Carter, P., Meth. in Enzymol., 154, 382 (1987)), and the method utilizing phage (Kramer, W. and Frits, H. J., Meth. in Enzymol., 154, 350 (1987); Kunkel, T. A. et al., Meth. in Enzymol., 154, 367 (1987)). Alternatively, a gene fragment in which objective codons are replaced may be totally synthesized. Frequencies of codons in various organisms are disclosed in the "Codon Usage Database" kazusa.or.jp; Nakamura, Y. et al, Nucl. Acids Res., 28, 292 (2000)).

Furthermore, the expression of a gene can also be increased by amplifying a regulator that increases the expression of the gene, or deleting or attenuating a regulator that reduces the expression of the gene.

Such methods for increasing the gene expression as mentioned above may be used independently or in an arbitrary combination.

The method for the transformation is not particularly limited, and conventionally known methods can be used. There can be used, for example, a method of treating recipient cells with calcium chloride so as to increase the permeability thereof for DNA, which has been reported for the *Escherichia coli* K-12 strain (Mandel, M. and Higa, A., J. Mol. Biol., 1970, 53, 159-162), and a method of preparing competent cells from cells which are in the growth phase, followed by transformation with DNA, which has been reported for *Bacillus subtilis* (Duncan, C. H., Wilson, G. A. and Young, F. E., Gene, 1977, 1:153-167). Alternatively, there can also be used a method of making DNA-recipient cells into protoplasts or spheroplasts, which can easily take up recombinant DNA, followed by introducing a recombinant DNA into the DNA-recipient cells, which is known to be applicable to *Bacillus subtilis*, actinomycetes, and yeasts (Chang, S. and Choen, S. N., 1979, Mol. Gen. Genet., 168:111-115; Bibb, M. J., Ward, J. M. and Hopwood, O. A., 1978, Nature, 274:398-400; Hinnen, A., Hicks, J. B. and Fink, G. R., 1978, Proc. Natl. Acad. Sci. USA, 75:1929-1933). Transformation of coryneform bacteria can be carried out by, specifically, for example, the protoplast method (Gene, 39, 281-286(1985)), the electroporation method (Bio/Technology, 7, 1067-1070(1989)), the electric pulse method (Japanese Patent Laid-open (Kokai) No. 2-207791), or the like.

An increase in the expression of a gene can be confirmed by, for example, confirming an increase in the activity of the protein expressed from the gene. An increase in the activity of a protein can be confirmed by measuring the activity of the protein. For example, an increase in the activity of the Tat secretion system can be confirmed by confirming an increase in the secretory production amount of a protein fused with a Tat-dependent signal peptide at the N-terminus. In such a case, it is preferred that the secretory production amount of the protein fused with a Tat-dependent signal peptide at the N-terminus is increased 1.5 times or more, 2 times or more, or 3 times or more, of that of a non-modified strain.

An increase in the expression of a gene can also be confirmed by, for example, confirming an increase in the transcription amount of the gene, or by confirming an increase in the amount of a protein expressed from the gene.

An increase of the transcription amount of a gene can be confirmed by comparing the amount of mRNA transcribed from the gene with that of a non-modified strain such as a wild-type strain or parent strain. Examples of the method for evaluating the amount of mRNA include Northern hybridization, RT-PCR, and so forth (Sambrook, J., et al., Molecular Cloning A Laboratory Manual/Third Edition, Cold Spring Harbor Laboratory Press, Cold Spring Harbor (USA), 2001). It is preferred that the amount of mRNA is increased, for example, 1.5 times or more, 2 times or more, or 3 times or more, of that of a non-modified strain.

An increase in the amount of a protein can be confirmed by performing SDS-PAGE and confirming the intensity of the separated protein band. An increase in the amount of a protein can be confirmed by Western blotting using antibodies (Molecular Cloning, Cold Spring Harbor Laboratory Press, Cold Spring Harbor (USA), 2001). It is preferred that the amount of the protein is increased, for example, 1.5 times or more, 2 times or more, or 3 times or more, of that of a non-modified strain.

<1-1-5> Genetic Construct for Secretory Expression of Heterologous Protein

It is known that a secretory protein is generally translated as a preprotein (also referred to as prepeptide) or a preproprotein (also referred to as prepropeptide), and then becomes a mature protein through processing. Specifically, a secretory protein is generally translated as a preprotein or preproprotein, then a signal peptide as the pre-moiety is cleaved with a protease (generally called signal peptidase), and the secretory protein is thereby converted into a mature protein or proprotein. As for the proprotein, the pro-moiety thereof is further cleaved by a protease, and the proprotein thereby becomes a mature protein. Therefore, a signal peptide is used for the secretory production of a heterologous protein in the method as described herein. A preprotein and a preproprotein of a secretory protein may be collectively referred to as "secretory protein precursor". The "signal peptide" (also referred to as "signal sequence") can refer to an amino acid sequence present at the N-terminus of a secretory protein precursor, and not usually present in the natural mature protein.

The genetic construct can include, in the direction from 5' to 3', a promoter sequence that is able to function in a coryneform bacterium, a nucleic acid sequence encoding a signal peptide that is able to function in a coryneform bacterium, and a nucleic acid sequence encoding a heterologous protein. The nucleic acid sequence encoding the signal peptide may be ligated downstream from the promoter sequence so that the signal peptide is expressed under the control of the promoter. The nucleic acid sequence encoding the heterologous protein may be ligated downstream from the nucleic acid sequence encoding the signal peptide so that the heterologous protein is expressed as a fusion protein with the signal peptide. This fusion protein can also be referred to as "fusion protein of the present invention". In the fusion protein, the signal peptide and the heterologous protein may be or may not be adjacent to each other. That is, the phrase "a heterologous protein is expressed as a fusion protein with a signal peptide" can include not only when a heterologous protein is expressed as a fusion protein with a signal peptide in which the signal peptide and the heterologous protein are adjacent to each other, but also can include when a heterologous protein is expressed as a fusion protein in which the signal peptide and the heterologous protein are fused with each other via another amino acid sequence. For example, as described later, the fusion protein can contain an insertion sequence, such as an amino acid sequence including Gln-Glu-Thr and an amino acid sequence used for enzymatic digestion, between the signal peptide and the heterologous protein. A nucleic acid sequence may also be read as "gene". For example, a nucleic acid sequence encoding a heterologous protein can also be referred to as "gene encoding a heterologous protein" or "heterologous protein gene". Examples of the nucleic acid sequence can include DNA. The genetic construct may also include a control sequence (operator, terminator, etc.) effective for expression of the fusion protein in a coryneform bacterium at such an appropriate position that it is able to function.

The promoter is not particularly limited so long as a promoter that functions in a coryneform bacterium is chosen. The promoter may be a promoter native to a coryneform bacterium, such as one derived from the host, or it may be a heterologous promoter. The promoter may be the native promoter of the heterologous protein, or a promoter of another gene. The "promoter that functions in a coryneform bacterium" can refer to a promoter that possesses promoter activity in a coryneform bacterium.

Specific examples of the heterologous promoter can include, for example, promoters native to E. coli such as tac promoter, lac promoter, trp promoter, and araBAD promoter. Among these, strong promoters such as tac promoter and inducible promoters such as araBAD promoter are preferred.

Examples of the promoter native to a coryneform bacterium can include, for example, promoters of the genes of the cell surface layer proteins PS1, PS2 (also referred to as CspB), and SlpA (also referred to as CspA), and promoters of various amino acid biosynthesis system genes. Specific examples of the promoters of various amino acid biosynthesis system genes can include, for example, promoters of the glutamate dehydrogenase gene of the glutamic acid biosynthesis system, the glutamine synthetase gene of the glutamine synthesis system, the aspartokinase gene of the lysine biosynthesis system, the homoserine dehydrogenase gene of the threonine biosynthesis system, the acetohydroxy acid synthetase gene of the isoleucine and valine biosynthesis system, 2-isopropylmalate synthetase gene of the leucine biosynthesis system, the glutamate kinase gene of the proline and arginine biosynthesis system, the phosphoribosyl-ATP pyrophosphorylase gene of the histidine biosynthesis system, the deoxyarabinoheptulonate phosphate (DAHP) synthetase gene of the aromatic amino acid biosynthesis systems such as those for tryptophan, tyrosine, and phenylalanine, the phosphoribosyl pyrophosphate (PRPP) amidotransferase gene of the nucleic acid biosynthesis systems such as those for inosinic acid and guanylic acid, the inosinic acid dehydrogenase gene, and the guanylic acid synthetase gene.

Examples of the promoter that functions in a coryneform bacterium can include such strong promoters as described above. As the promoter, a high activity inherent promoter may be obtained by using various reporter genes, and used. For example, by making the −35 and −10 regions in a promoter region closer to a consensus sequence, activity of the promoter can be enhanced (International Patent Publication WO00/18935). Examples of the method for evaluating strength of a promoter and strong promoters are described in the paper of Goldstein et al. (Prokaryotic promoters in biotechnology, Biotechnol. Annu. Rev., 1, 105-128 (1995)) and so forth. Furthermore, it is known that substitution, insertion, or deletion of several nucleotides in a spacer region between the ribosome-binding site (RBS) and the start codon, especially in a sequence immediately upstream of the start codon (5'-UTR), significantly affects stability and translation efficiency of mRNA, and these sequences can also be modified.

The signal peptide is not particularly limited so long as it is able to function in a coryneform bacterium. The signal peptide may be a signal peptide derived from a coryneform bacterium, such as one derived from the host, or it may be a heterologous signal peptide. The signal peptide may be the native signal peptide of the heterologous protein, or a signal peptide of another gene. The phrase "signal peptide that is able to function in a coryneform bacterium" can refer to a peptide that when it is ligated to the N-terminus of an objective protein, it allows the coryneform bacterium to secrete the protein. Whether a signal peptide is able to function in a coryneform bacterium can be confirmed by, for example, expressing an objective protein fused with the signal peptide, and confirming whether the protein is secreted.

Examples of the signal peptide include Tat-dependent signal peptides and Sec-dependent signal peptides.

The term "Tat-dependent signal peptide" can refer to a signal peptide recognized by the Tat system. The term "Tat-dependent signal peptide" may specifically refer to a signal peptide that, upon being linked at the N-terminus of an objective protein, results in secretion of the protein by the Tat secretion system.

Examples of the Tat-dependent signal peptide include the signal peptide of the TorA protein (trimethylamine-N-oxidoreductase) of *E. coli*, the signal peptide of SufI protein (suppressor of ftsI) of *E. coli*, the PhoD protein (phosphodiesterase) of *Bacillus subtilis*, the signal peptide of LipA protein (lipoic acid synthase) of *Bacillus subtilis*, and the signal peptide of IMD protein (isomaltodextranase) of *Arthrobacter globiformis*. The amino acid sequences of these signal peptides are as follows:

```
TorA signal peptide:
                                          (SEQ ID NO: 75)
MNNNDLFQASRRRFLAQLGGLTVAGMLGPSLLTPRRATA SufI signal peptide:
                                          (SEQ ID NO: 76)
MSLSRRQFIQASGIALCAGAVPLKASA PhoD signal peptide:
                                          (SEQ ID NO: 77)
MAYDSRFDEWVQKLKEESFQNNTFDRRKFIQGAGKIAGLSLGLTIAQS LipA signal peptide:
                                          (SEQ ID NO: 78)
MKFVKRRTTALVTTLMLSVTSLFALQPSAKAAEH IMD signal peptide:
                                          (SEQ ID NO: 79)
MMNLSRRTLLTTGSAATLAYALGMAGSAQA
```

The Tat-dependent signal peptide has a twin-arginine motif. Examples of the twin-arginine motif include S/T-R-R-X-F-L-K (SEQ ID NO: 80) and R-R-X-#-# (#: hydrophobic residue) (SEQ ID NO: 81).

The term "Sec-dependent signal peptide" can refer to a signal peptide recognized by the Sec system. The term "Sec-dependent signal peptide" may specifically refer to a signal peptide that, upon being linked at the N-terminus of an objective protein, results in secretion of the protein by the Sec secretion system.

Examples of the Sec-dependent signal peptide include a signal peptide of a cell surface layer protein of a coryneform bacterium. The cell surface layer protein of coryneform bacteria is as described above. Examples of the cell surface layer protein of coryneform bacteria include PS1 and PS2 (CspB) native to *C. glutamicum* (Japanese Patent Laid-open (Kohyo) No. 6-502548), and SlpA (CspA) native to *C. ammoniagenes* (*C. stationis*) (Japanese Patent Laid-open (Kokai) No. 10-108675). The amino acid sequence of the signal peptide of PS1 (PS1 signal peptide) of *C. glutamicum* is shown in SEQ ID NO: 82, the amino acid sequence of the signal peptide of PS2 (CspB) (PS2 signal peptide) of *C. glutamicum* is shown in SEQ ID NO: 83, and the amino acid sequence of the signal peptide of SlpA (CspA) (SlpA signal peptide) of *C. stationis* is shown in SEQ ID NO: 84. Moreover, U.S. Pat. No. 4,965,197 describes signal peptides for DNases native to coryneform bacteria, and such signal peptides can also be used in the method described herein.

The Tat-dependent signal peptide may be a variant of any of the Tat-dependent signal peptides exemplified above, so long as it contains a twin-arginine motif and the original function thereof is maintained. The Sec-dependent signal peptide may be a variant of any of the Sec-dependent signal peptides exemplified above, so long as the original function thereof is maintained. The above descriptions concerning conservative variants of the phoS gene and PhoS protein can be applied mutatis mutandis to variants of the signal peptide and the gene encoding it. For example, the signal peptide may be a peptide having any of the aforementioned amino acid sequences, but which can include substitution, deletion, insertion, or addition of one or several amino acid residues at one or several positions. The number meant by the term "one or several" in reference to a variant of the signal peptide can be specifically, 1 to 7, 1 to 5, 1 to 3, or 1 to 2. The terms "TorA signal peptide", "SufI signal peptide", "PhoD signal peptide", "LipA signal peptide", "IMD signal peptide", "PS1 signal peptide", "PS2 signal peptide", and "SlpA signal peptide" can include not only the peptides of SEQ ID NOS: 75, 76, 77, 78, 79, 82, 83, and 84, respectively, but also can include conservative variants thereof.

The expression "original function is maintained" in reference to the Tat-dependent signal peptide can mean that the peptide is recognized by the Tat system, and specifically, may mean that the peptide is able to induce, upon being linked at the N-terminus of an objective protein, secretion of the protein by the Tat secretion system. Whether a peptide will function as the Tat-dependent signal peptide can be confirmed by, for example, confirming an increase in the secretory production amount of a protein that is linked to the peptide at the N-terminus due to enhancement of the Tat secretion system, or confirming a reduction in the secretory production amount of a protein that is linked to the peptide at the N-terminus due to deletion of the Tat secretion system.

The expression "original function is maintained" in reference to the Sec-dependent signal peptide can mean that the peptide is recognized by the Sec system, and specifically, may mean that the peptide is able to induce, upon being linked at the N-terminus of an objective protein, secretion of the protein by the Sec secretion system. Whether a peptide will function as the Sec-dependent signal peptide can be confirmed by, for example, confirming an increase in the secretory production amount of a protein that is linked with the peptide at the N-terminus due to enhancement of the Sec secretion system, or confirming a reduction in the secretory production amount of a protein that is linked with the peptide at the N-terminus due to deletion of the Sec secretion system.

The signal sequence is generally cleaved by a signal peptidase, when the translation product is secreted out of the cell. As a gene encoding a signal peptide, although a naturally occurring gene may be used as it is, it may be modified so that it has the optimal codons according to codon frequencies in the chosen host.

In the genetic construct, a nucleic acid sequence encoding an amino acid sequence including Gln-Glu-Thr may be inserted between the nucleic acid sequence encoding the signal peptide and the nucleic acid sequence encoding the heterologous protein (WO2013/062029). The "amino acid sequence including Gln-Glu-Thr" can also be referred to as "insertion sequence". Examples of the insertion sequence can include amino acid sequences that include Gln-Glu-Thr described in WO2013/062029. The insertion sequence can be used in combination with the Sec-dependent signal peptide.

The insertion sequence can be a sequence having 3 or more amino acid residues from the N-terminus of the mature protein of the cell surface layer protein CspB of a coryneform bacterium (henceforth also referred to as "mature CspB" or "CspB mature protein"). The term "sequence having 3 or more amino acid residues from the N-terminus" can refer to an amino acid sequence starting from the amino acid residue at position 1 of the N-terminus to an amino acid residue at position 3 or a more remote position.

The cell surface layer protein CspB of coryneform bacteria is as described above. Specific examples of CspB can include, for example, CspB of *C. glutamicum* ATCC 13869, CspB of the 28 strains of *C. glutamicum* exemplified above, and variants thereof. In the amino acid sequence of the CspB protein of *C. glutamicum* ATCC 13869 shown in SEQ ID NO: 68, the amino acid residues at positions 1 to 30 correspond to the signal peptide, and the amino acid residues at positions 31 to 499 correspond to the CspB mature protein. The amino acid sequence of the CspB mature protein of *C. glutamicum* ATCC 13869 except for the 30 amino acid residues as the signal peptide moiety is shown in SEQ ID NO: 85. In the mature CspB of *C. glutamicum* ATCC 13869, the amino acid residues at positions 1 to 3 of the N-terminus correspond to Gln-Glu-Thr.

The insertion sequence can be an amino acid sequence starting from the amino acid residue at position 1 and ending at an amino acid residue at any of the positions 3 to 50 of the mature CspB. The insertion sequence can be an amino acid sequence starting from the amino acid residue at position 1 and ending at an amino acid residue at any of the positions 3 to 8, 17, and 50 of the mature CspB. The insertion sequence can also be an amino acid sequence starting from the amino acid residue at position 1 and ending at an amino acid residue at any of the positions 4, 6, 17 and 50.

The insertion sequence can be an amino acid sequence as follows:

(A)
Gln-Glu-Thr (B) (SEQ ID NO: 86)
Gln-Glu-Thr-Xaa1

(C) (SEQ ID NO: 87)
Gln-Glu-Thr-Xaa1-Xaa2

(D) (SEQ ID NO: 88)
Gln-Glu-Thr-Xaa1-Xaa2-Xaa3

(E) an amino acid sequence of Gln-Glu-Thr fused with the amino acid residues at positions 4 to 7 of a mature CspB, (F) an amino acid sequence of Gln-Glu-Thr fused with the amino acid residues at positions 4 to 8 of a mature CspB, (G) an amino acid sequence of Gln-Glu-Thr fused with the amino acid residues at positions 4 to 17 of a mature CspB, (H) an amino acid sequence of Gln-Glu-Thr fused with the amino acid residues at positions 4 to 50 of a mature CspB.

In the amino acid sequences (A) to (H) depicted above, Xaa1 is Asn, Gly, Thr, Pro, or Ala, Xaa2 is Pro, Thr, or Val, and Xaa3 is Thr or Tyr. As for the amino acid sequences (A) to (H) depicted above, "Gln-Glu-Thr fused with the amino acid residues at positions 4 to X of a mature CspB" can mean that the amino acid residues at positions 4 to X of the N-terminus of a mature CspB is fused to Thr of Gln-Glu-Thr. The first to third amino acid residues of the N-terminus of a mature CspB are usually Gln-Glu-Thr, and in such a case, "an amino acid sequence of Gln-Glu-Thr fused with the amino acid residues at positions 4 to X of a mature CspB" is synonymous with an amino acid sequence having the amino acid residues at position 1 to X of the mature CspB.

Furthermore, specifically, the insertion sequence can be Gln-Glu-Thr-Asn-Pro-Thr (SEQ ID NO: 89), Gln-Glu-Thr-Gly-Thr-Tyr (SEQ ID NO: 90), Gln-Glu-Thr-Thr-Val-Thr (SEQ ID NO: 91), Gln-Glu-Thr-Pro-Val-Thr (SEQ ID NO: 92), or Gln-Glu-Thr-Ala-Val-Thr (SEQ ID NO: 93).

The "amino acid residue at position X of the mature CspB" can refer to an amino acid residue corresponding to the amino acid residue at position X in SEQ ID NO: 85. Which amino acid residue is the "amino acid residue corresponding to the amino acid residue at position X in SEQ ID NO: 85" in the amino acid sequence of an arbitrary mature CspB can be determined by alignment between the amino acid sequence of the arbitrary mature CspB and the amino acid sequence of SEQ ID NO: 85.

Examples of the heterologous protein to be produced by secretory production according to the method as described herein can include, for example, physiologically active proteins, receptor proteins, or antigenic proteins to be used as vaccines, and enzymes.

Examples of the enzymes can include, for example, transglutaminase, protein glutaminase, isomaltodextranase, protease, endopeptidase, exopeptidase, aminopeptidase, carboxypeptidase, collagenase, chitinase, and so forth. Examples of transglutaminase can include, for example, secretory-type transglutaminases of Actinomycetes such as *Streptoverticillium mobaraense* IFO 13819 (WO01/23591), *Streptoverticillium cinnamoneum* IFO 12852, *Streptoverticillium griseocarneum* IFO 12776, and *Streptomyces lydicus* (WO96/06931), and of filamentous fungi such as Oomycetes (WO96/22366). Examples of protein glutaminase include, for example, protein glutaminase of *Chryseobacterium proteolyticum* (WO2005/103278). Examples of isomaltodextranase include, for example, isomaltodextranase of *Arthrobacter globiformis* (WO2005/103278).

Examples of the physiologically active proteins can include, for example, growth factors, hormones, cytokines, and antibody-related molecules.

Specific examples of the growth factors can include, for example, epidermal growth factor (EGF), insulin-like growth factor-1 (IGF-1), transforming growth factor (TGF), nerve growth factor (NGF), brain-derived neurotrophic factor (BDNF), vesicular endothelial growth factor (VEGF), granulocyte-colony stimulating factor (G-CSF), granulocyte-macrophage-colony stimulating factor (GM-CSF), platelet-derived growth factor (PDGF), erythropoietin (EPO), thrombopoietin (TPO), acidic fibroblast growth factor (aFGF or FGF1), basic fibroblast growth factor (bFGF or FGF2), keratinocyte growth factor (KGF-1 or FGF7, and, KGF-2 or FGF10), and hepatocyte growth factor (HGF).

Specific examples of the hormones can include, for example, insulin, glucagon, somatostatin, human growth hormone (hGH), parathyroid hormone (PTH), calcitonin, and exenatide.

Specific examples of the cytokines can include, for example, interleukins, interferons, and tumor necrosis factors (TNFs).

The growth factors, hormones, and cytokines may not be strictly distinguished from one another. For example, a physiologically active protein may be considered to be a growth factor, for example, but may also be considered to be both a growth factor and a hormone, for example.

Furthermore, a physiologically active protein may be an intact protein, or may be a part of a protein. Examples of a part of a protein can include, for example, a part having physiological activity. Specific examples of a part having physiological activity can include, for example, teriparatide, a physiologically active peptide having the N-terminal 34 amino acid residues of parathyroid hormone (PTH).

The term "antibody-related molecule" can refer to a protein containing a molecular species having a single domain or a combination of two or more domains of the domains that make up a complete antibody. Examples of the domains that make up a complete antibody can include heavy chain domains VH, CH1, CH2, and CH3, and light chain domains VL and CL. The antibody-related molecule may be a monomeric protein, or may be a multimeric protein, so long as it contains the above-mentioned molecular species. When the antibody-related molecule is a multimeric protein, it may be a homo-multimer having a single kind of subunit, or may be a hetero-multimer having two or more kinds of subunits. Specific examples of the antibody-related molecules can include, for example, complete antibody, Fab, F(ab'), F(ab')$_2$, Fc, dimer having a heavy chain (H chain) and a light chain (L chain), Fc-fusion protein, heavy chain (H chain), light chain (L chain), light chain Fv (scFv), sc(Fv)$_2$, disulfide-bonded Fv (sdFv), and diabody.

The receptor proteins are not particularly limited. A receptor protein may be, for example, a receptor protein for any of physiologically active proteins and other physiologically active substances. Examples of the other physiologically active substances can include, for example, neurotransmitters such as dopamine. Furthermore, a receptor protein may be an orphan receptor of which the corresponding ligand is not known.

The antigen proteins to be used as vaccines are not particularly limited, so long as they are proteins that can induce an immune response. An antigen protein can be appropriately selected depending on the intended object of the immune response.

In addition, examples of other proteins include liver-type fatty acid-binding protein (LFABP).

Genes encoding these proteins can be modified according to the chosen host and so that the desired activity is obtained. For example, the genes encoding these proteins may each be modified so that the proteins include addition, deletion, substitution, or the like of one or several amino acid residues. The above descriptions concerning variants of the PhoS protein and phoS gene can be applied mutatis mutandis to the heterologous protein to be produced by secretory production by the method as described herein and the gene encoding it. Furthermore, in the genes encoding these proteins, an arbitrary codon may be replaced with an equivalent codon thereof. For example, in the genes encoding these proteins, codons may be optimized as required according to codon frequencies observed in the chosen host.

The genetic construct may further include a nucleic acid sequence encoding an amino acid sequence used for enzymatic digestion between the nucleic acid sequence encoding the amino acid sequence including Gln-Glu-Thr and the nucleic acid sequence encoding the heterologous protein. If the amino acid sequence used for enzymatic digestion is inserted into the fusion protein, the expressed fusion protein can be enzymatically digested to obtain the objective heterologous protein.

The amino acid sequence used for enzymatic digestion is not particularly limited so long as the chosen sequence can be recognized and digested by an enzyme that hydrolyzes a peptide bond, and a sequence can be appropriately chosen according to the amino acid sequence of the objective heterologous protein. The nucleic acid sequence encoding the amino acid sequence used for enzymatic digestion may be designed on the basis of that amino acid sequence, and for example, optimal codons can be used according to codon frequencies observed in the chosen host.

The amino acid sequence used for enzymatic digestion can be a recognition sequence of a protease showing high substrate specificity. Specific examples of such an amino acid sequence can include, for example, a recognition sequence of factor Xa protease and a recognition sequence of proTEV protease. The factor Xa protease and the proTEV protease recognize the amino acid sequence of Ile-Glu-Gly-Arg (=IEGR, SEQ ID NO: 94) and the amino acid sequence of Glu-Asn-Leu-Tyr-Phe-Gln (=ENLYFQ, SEQ ID NO: 95) in a protein, respectively, to specifically digest the protein at the C-terminal side of each recognition sequence.

The N-terminal region of the heterologous protein eventually obtained by the method as described herein may be the same as that of the natural protein, or may not be the same as that of the natural protein. For example, the N-terminal region of the eventually obtained heterologous protein may be that of the natural protein but can include addition or deletion of one or several amino acid residues. Although the number of the "one or several" amino acid residues may differ depending on the full length or structure of the objective heterologous protein, specifically, it can be 1 to 20, 1 to 10, 1 to 5, or 1 to 3.

Furthermore, the heterologous protein to be produced by secretory production may be a protein including a pro-structure moiety (proprotein). When the heterologous protein to be produced by secretory production is a proprotein, the heterologous protein to be eventually obtained may be the proprotein or may not be the proprotein. That is, the proprotein may be processed into the mature protein by cleavage of the pro-structure moiety. The cleavage can be attained with, for example, a protease. When a protease is used, generally, the proprotein can be cleaved at a position substantially the same as that of the natural protein, or at exactly the same position as that of the natural protein so that the same mature protein as the natural mature protein is obtained, in view of the activity of the eventually obtained protein. Therefore, generally, a specific protease that cleaves the proprotein at such a position that the same protein as the naturally occurring mature protein is generated is most preferred. However, the N-terminal region of the heterologous protein to be eventually obtained may not be the same as that of the natural protein as described above. For example, depending on type, purpose of use etc. of the heterologous protein to be produced, a protein having an N-terminus longer or shorter by one to several amino acid residues compared with the natural protein may have more appropriate activity. Proteases can include, for example, commercially available proteases such as Dispase (produced by Boehringer Mannheim) as well as those obtainable from culture broth of a microorganism such as culture broth of actinomycetes. Such proteases may be used in an un-purified state, or may be used after purification to an appropriate purity as required. When the pro-structure moiety is cleaved to obtain a mature protein, the inserted amino acid sequence including Gln-Glu-Thr is removed together with the pro-structure moiety, and therefore the objective protein can be obtained without providing an amino acid sequence used for enzymatic digestion downstream from the amino acid sequence including Gln-Glu-Thr.

The method for introducing the genetic construct into the coryneform bacterium is not particularly limited. The phrase "introduction of the genetic construct" can refer to making a host harbor the genetic construct. The phrase "introduction of the genetic construct" can include not only when the genetic construct that has been preliminarily constructed is collectively introduced into a host, but also can include when at least the heterologous protein gene is introduced into a host and the genetic construct is constructed in the host. In the bacterium, the genetic construct may be present on a vector that autonomously replicates out of the chromosome such as a plasmid, or may be incorporated into the chromosome. The genetic construct can be introduced, for example, in the same manner as that for introduction of a gene in methods for increasing the expression of a gene described above. In addition, for constructing the bacterium, introduction of the genetic structure, introduction of the mutant phoS gene, and other modifications can be performed in any arbitrary order.

The genetic construct can be introduced into a host by using, for example, a vector that includes the genetic construct. For example, the genetic construct can be introduced into a host by ligating the genetic construct with a vector to construct an expression vector of the genetic construct, and transforming the host with the expression vector. Also, when the vector contains a promoter that functions in a coryneform bacterium, an expression vector of the genetic construct can be constructed by ligating the nucleic acid sequence encoding the fusion protein downstream from the promoter. The vector is not particularly limited so long as the vector is able to be autonomously replicable in a coryneform bacterium. The vector usable in a coryneform bacterium is as described above.

Furthermore, the genetic construct can be introduced into the chromosome of a host by using, for example, a transposon such as an artificial transposon. When a transposon is used, the genetic construct can be introduced into the chromosome by homologous recombination or translocation ability of the transposon itself. Furthermore, the genetic construct can also be introduced into the chromosome of a host by other introduction methods utilizing homologous recombination. Examples of the introduction methods utilizing homologous recombination include, for example, methods utilizing a linear DNA, a plasmid having a temperature sensitive replication origin, a plasmid capable of conjugative transfer, a suicide vector not having a replication origin that functions in a host, and so forth. In addition, at least the heterologous protein gene may be introduced into the chromosome so that the genetic construct is present on the chromosome. In this case, a part or all of the constituents contained in the genetic construct, other than the heterologous protein gene, may be inherently present on the chromosome of the host. Specifically, for example, by using a promoter sequence inherently present on the chromosome of the host and a nucleic acid sequence encoding a signal peptide inherently present on the chromosome of the host and ligated downstream from the promoter sequence as they are, and replacing only the gene ligated downstream from the nucleic acid sequence encoding the signal peptide with an objective heterologous protein gene, the genetic construct can be present on the chromosome, and the bacterium can be thereby constructed. A part of the genetic construct, such as the heterologous protein gene, can be introduced into the chromosome in the same manner as that for introduction of the genetic construct into the chromosome.

The genetic construct or a constituent thereof, such as promoter sequence, nucleic acid sequence encoding a signal peptide, or nucleic acid sequence encoding a heterologous protein, can be obtained by, for example, cloning. Specifically, for example, the genetic construct can be obtained by cloning an objective heterologous protein gene from an organism having the objective heterologous protein, and then subjecting the gene to modification such as introduction of the nucleic acid sequence encoding the signal peptide and introduction of the promoter sequence. Furthermore, the genetic construct or a constituent thereof can also be obtained by chemical synthesis. The genetic construct used for the present invention or constituent thereof can be used as it is, or after being modified as required.

Furthermore, when two or more kinds of proteins are expressed, it is sufficient that the genetic constructs for secretory expression of the proteins are harbored by the bacterium so that secretory expression of the objective heterologous proteins can be attained. Specifically, for example, all the genetic constructs for secretory expression of the proteins may be harbored on a single expression vector, or harbored on the chromosome. Alternatively, the genetic constructs for secretory expression of the proteins may be separately harbored on a plurality of expression vectors, or may be separately harbored on one or more expression vectors and the chromosome. The phrase "when two or more kinds of proteins are expressed" can refer to, for example, when two or more kinds of heterologous proteins are produced by secretory production, or when a heteromultimeric protein is produced by secretory production.

The method for introducing the genetic construct into the coryneform bacterium is not particularly limited, and a previously reported and typical method, for example, the protoplast method (Gene, 39, 281-286 (1985)), the electroporation method (Bio/Technology, 7, 1067-1070 (1989)), the electric pulse method (Japanese Patent Laid-open (Kokai) No. 2-207791), and so forth can be used.

<1-2> Method for Producing Heterologous Protein

By culturing the bacterium obtained as described above to express a heterologous protein, a large amount of the heterologous protein is secreted out of the cells.

The bacterium can be cultured according to a previously reported and typical method and conditions. For example, the bacterium can be cultured in a usual medium containing a carbon source, a nitrogen source, and inorganic ions. In order to obtain still higher proliferation, organic micronutrients such as vitamins and amino acids can also be added as required.

As the carbon source, carbohydrates such as glucose and sucrose, organic acids such as acetic acid, alcohols, and others can be used. As the nitrogen source, ammonia gas, aqueous ammonia, ammonium salts, and others can be used. As the inorganic ions, calcium ions, magnesium ions, phosphate ions, potassium ions, iron ions, and so forth are appropriately used as required. The culture can be performed within appropriate ranges of pH such as 5.0 to 8.5, and temperature such as 15 to 37° C. under aerobic conditions for 1 to 7 days. Furthermore, the culture conditions for L-amino acid production by coryneform bacteria and other conditions described for the methods for producing a protein using a Sec- or Tat-dependent signal peptide can be used (refer to WO01/23591 and WO2005/103278). Furthermore, when an inducible promoter is used for expression of the heterologous protein, a promoter-inducing agent can be added to the culture medium. By culturing the bacterium under such conditions, a large amount of the objective protein is produced in cells and efficiently secreted out of the cells. In addition, according to the method as described herein, the produced heterologous protein is secreted out of the cells, and therefore a protein that is generally lethal if it is accumulated in a large amount in cells of microorganisms, such as transglutaminases, can also be continuously produced without lethal effect.

The protein secreted in the medium according to the method as described herein can be separated and purified from the medium after the culture by a method well known to those skilled in the art. For example, after the cells are removed by centrifugation or the like, the protein can be separated and purified by a known appropriate method such as salting out, ethanol precipitation, ultrafiltration, gel filtration chromatography, ion exchange column chromatography, affinity chromatography, medium or high pressure liquid chromatography, reverse phase chromatography, and hydrophobic chromatography, or a combination of these. Furthermore, the culture or culture supernatant may be used as it is. The protein secreted in the cell surface layer according to the method as described herein can also be separated and purified in the same manner as when the protein is secreted in the medium, after solubilizing it by a method well known to those skilled in the art such as elevation of salt concentration and use of a surfactant. Furthermore, the protein secreted in the cell surface layer may be used as, for example, an immobilized enzyme, without solubilizing it.

Secretory production of the objective heterologous protein can be confirmed by performing SDS-PAGE for the culture supernatant and/or a fraction containing the cell surface layer as a sample, and confirming the molecular weight of the separated protein band. Furthermore, secretory production of the objective heterologous protein can also be confirmed by performing Western blotting using antibodies for the culture supernatant and/or a fraction containing the cell surface layer as a sample (Molecular Cloning, Cold spring Harbor Laboratory Press, Cold Spring Harbor (USA), 2001). Furthermore, secretory production of the objective heterologous protein can also be confirmed by detecting an N-terminal amino acid sequence of the objective protein using a protein sequencer. Furthermore, secretory production of the objective heterologous protein can also be confirmed by determining the mass of the objective protein using a mass spectrometer. Furthermore, when the objective heterologous protein is an enzyme or a protein having a certain measurable physiological activity, secretory production of the objective heterologous protein can be confirmed by measuring enzymatic activity or the physiological activity of the objective protein in the culture supernatant and/or a fraction containing the cell surface layer as a sample.

<2> Coryneform Bacterium Harboring Mutant phoS Gene

The present invention also provides a coryneform bacterium harboring a mutant phoS gene. This coryneform bacterium may or may not have an ability of secretory production of a heterologous protein. Hence, this coryneform bacterium may or may not have a genetic construct for secretory expression of a heterologous protein. The above descriptions concerning the "coryneform bacterium used for the method as described herein" can be applied mutatis mutandis to this coryneform bacterium, provided that this coryneform bacterium may not have the genetic construct for secretory expression of a heterologous protein. This coryneform bacterium, for example, can be made to harbor the genetic construct for secretory expression of a heterologous protein and can be used for secretory production of the heterologous protein. That is, an embodiment of this coryneform bacterium is the aforementioned "coryneform bacterium used for the method as described herein".

EXAMPLES

The present invention will be further specifically explained with reference to the following non-limiting examples.

Example 1

(1) Generation of PhoS-mutant Strains Derived from *C. glutamicum* YDK010 Strain The *C. glutamicum* YDK010 strain disclosed in WO2002/081694 was transformed with pPKK50TEV-Teri disclosed in WO2014/126260, which is a secretory expression plasmid of the physiologically active peptide teriparatide. pPKK50TEV-Teri is a secretory expression vector capable of generating the physiologically active teriparatide peptide. pPKK50TEV-Teri is a plasmid having the promoter region of the cspB gene of the *C. glutamicum* ATCC13869 strain and a nucleotide sequence operably-linked downstream from the promoter and encoding a fusion protein (hereinafter, referred to as CspB50TEV-Teri) that includes the CspB signal peptide of the same strain, the N-terminal 50 amino acid residues of mature CspB of the same strain, the ProTEV protease recognition sequence ENLYFQ (SEQ ID No. 95), and teriparatide (WO2014/126260). The *C. glutamicum* YDK010 strain is a cell-surface-layer-protein-CspB-deficient strain of the *C. glutamicum* AJ12036 strain (FERM BP-734). The obtained transformant was cultured on CMDex agar medium (5 g of glucose, 0.4 g of $MgSO_4 \cdot 7H_2O$, 0.01 g of $FeSO_4 \cdot 7H_2O$, 0.01 g of $MnSO_4 \cdot 5H_2O$, 1 g of $KH_2PO_4$, 10 μg of biotin, 10 g of Difco™ Select Soytone (Becton Dickinson), 10 g of Bacto™ Yeast Extract (Becton Dickinson), 3 g of urea, 1.2 g (as total nitrogen) of soybean hydrolysate solution obtained with HCl, and 20 g of agar powder, filled up with water to 1 L, and adjusted to pH6.5) containing 25 mg/L of kanamycin at 30° C., to form colonies.

After the culture, a natural mutant strain into which the phoS gene is introduced with a mutation was selected, and designated as strain YDK0107. The nucleotide sequence of the mutant phoS gene of the YDK0107 strain and the amino acid sequence of the mutant PhoS protein of the YDK0107 strain are shown in SEQ ID NOS: 1 and 2, respectively. In the mutant phoS gene of the YDK0107 strain, the "G" at position 906 of SEQ ID NO: 3 of the wild-type phoS gene of the YDK010 strain has been mutated to "T". Due to this mutation, in the mutant PhoS protein of the YDK0107 strain, the tryptophan residue at position 302 of SEQ ID NO: 4 of the wild-type PhoS protein of the YDK010 strain has been mutated to a cysteine residue. This mutation was designated as PhoS(W302C) mutation. Genomic DNA was prepared with PurElute™ Genomic DNA Kit (EdgeBio), and nucleotide sequencing was carried out with BigDye(R) Terminator v3.1 Cycle Sequencing Kit (Applied Biosystems) and 3130 Genetic Analyzer (Applied Biosystems).

(2) Construction of phoS-gene-substitution Vector Encoding Mutant PhoS(W302C)

PCR was carried out by using primers of SEQ ID NOS: 5 and 6, and genomic DNA of the *C. glutamicum* YDK0107 strain prepared with PurElute™ Genomic DNA Kit (EdgeBio) as the template, to amplify a region of about 1.5 kbp containing a phoS gene encoding the mutant PhoS(W302C) (also referred to as mutant phoS gene or mutant phoS (W302C) gene). PCR was carried out with Pyrobest(R) DNA polymerase (Takara Bio), and the reaction conditions were according to the protocol recommended by the manufacturer.

Then, the amplified DNA fragment of about 1.5 kbp was subject to agarose gel electrophoresis, an objective band was cut out, and the DNA fragment was collected from the gel with Wizard® SV Gel and PCR Clean-Up System (Promega). The collected DNA fragment was inserted at the SmaI site of pBS5T disclosed in WO2006/057450, and then introduced into competent cells of *E. coli* JM109 (Takara Bio). A strain harboring a plasmid with the cloned DNA fragment containing the mutant phoS gene was obtained, the plasmid was collected from the strain, to obtain pBS5T- phoS(W302C), the plasmid into which the mutant phoS gene was cloned. As a result of nucleotide sequencing of the inserted fragment, it was confirmed that the expected gene was cloned. Nucleotide sequencing was carried out with BigDye® Terminator v3.1 Cycle Sequencing Kit (Applied Biosystems) and 3130 Genetic Analyzer (Applied Biosystems).

(3) Construction of PhoS(W302C)-mutant Strain

The *C. glutamicum* YDK010 strain disclosed in WO2002/081694 was transformed with the plasmid pBS5T-phoS (W302C) constructed in Example 1(2). Strain selection from the obtained transformants was carried out according to the method disclosed in WO2006/057450, to obtain YDK010::phoS(W302C), which is a strain in which the wild-type phoS gene on the chromosome was replaced with the mutant phoS gene. Incidentally, even without using the genome DNA of the YDK0107 strain, the YDK010::phoS(W302C) strain can be reproductively constructed by using, for example, the mutant phoS gene obtained by genetic engineering.

(4) Construction of phoS-gene-deletion Vector pBS5TΔphoS

PCR was carried out by using genomic DNA of the *C. glutamicum* ATCC13869 strain prepared with PurElute™ Genomic DNA Kit (EdgeBio) as the template, in combination with primers of SEQ ID NOS: 7 and 8 to amplify a 5'-side upstream region of the phoS gene of about 1 kbp, and in combination with primers of SEQ ID NOS: 9 and 10 to amplify a 3'-side downstream region of the phoS gene of about 1 kbp. PCR was carried out with Pyrobest(R) DNA polymerase (Takara Bio), and the reaction conditions were according to the protocol recommended by the manufacturer. The amplified DNA fragments of about 1 kbp each were subject to agarose gel electrophoresis, objective bands were cut out, and the DNA fragments were collected from the gel with Wizard® SV Gel and PCR Clean-Up System (Promega). The collected two DNA fragments were inserted at the SmaI site of pBS5T disclosed in WO2006/057450 by infusion reaction, to obtain a phoS-gene-deletion vector pBS5TΔphoS. The infusion reaction was carried out with In-Fusion® HD Cloning Kit (Takara Bio), and the reaction conditions were according to the protocol recommended by the manufacturer.

(5) Construction of PhoS-deletion Strain of YDK010 Strain

The *C. glutamicum* YDK010 strain disclosed in WO2002/081694 was transformed with the plasmid pBS5TΔphoS constructed in Example 1(4). Strain selection from the obtained transformants was carried out according to the method disclosed in WO2006/057450, to obtain YDK010::phoS(W302C), which is a strain deficient in the phoS gene.

Example 2

(1) Secretory Production of CspB50TEV-teriparatide Fusion Protein Using CspB Signal Sequence in PhoS (W302C)-Mutant and PhoS-Deletion Strains The *C. glutamicum* YDK010 strain disclosed in WO2002/081694, the YDK0107 strain obtained in Example 1(1), the YDK010::phoS(W302C) strain obtained in Example 1(3), and the YDK010ΔphoS strain obtained in Example 1(5) were each transformed with the plasmid pPKK50TEV-Teri disclosed in WO2014/126260, to obtain strains YDK010/pPKK50TEV-Teri, YDK0107/pPKK50TEV-Teri, YDK010::phoS(W302C)/pPKK50TEV-Teri, and YDK010ΔphoS/pPKK50TEV-Teri. pPKK50TEV-Teri is a secretory expression plasmid capable of generating the physiologically active teriparatide peptide. The obtained transformants were each cultured on MMTG liquid medium (120 g of glucose, 3 g of $MgSO_4.7H_2O$, 30 g of $(NH_4)_2SO_4$, 1.5 g of $KH_2PO_4$, 0.03 g of $FeSO_4.7H_2O$, 0.03 g of $MnSO_4.5H_2O$, 0.45 mg of thiamine hydrochloride, 0.45 mg of biotin, 0.15 g of DL-methionine, 0.2 g (as total nitrogen) of soybean hydrolysate solution obtained with HCl, and 50 g of $CaCO_3$, filled up with water to 1 L, and adjusted to pH7.0) containing 25 mg/L of kanamycin at 30° C. for 72 hr. After completion of the culture, 5 μL of the culture supernatant obtained by centrifuging each culture broth was subjected to reduced SDS-PAGE, and then staining was carried out with SYPRO Orange (Life Technologies). As a result, the secretion amount of CspB50TEV-Teri was significantly improved in the YDK0107 and YDK010::phoS (W302C) strains, as compared with the YDK010 strain (FIG. 1). After the staining, the band intensity of CspB50TEV-Teri was digitized with image analysis software Multi Gauge (FUJIFILM), and the average value of the band intensity observed upon expressing CspB50TEV-Teri in each strain was calculated as a relative value based on the average value of the band intensity observed upon expressing CspB50TEV-Teri in the YDK010 strain, which was taken as 1. As a result, it was confirmed that the secretion amount of CspB50TEV-Teri was improved about 13.2-fold in the YDK0107 strain and about 12.5-fold in the YDK010::phoS(W302C) strain, as compared with the YDK010 strain (Table 1). By contrast, the secretion amount of CspB50TEV-Teri was reduced about 0.2-fold in the YDK010ΔphoS strain, as compared with the YDK010 strain. From this, the PhoS(W302C) mutation is shown to be an effective mutation that leads to a significant improvement of the amount of CspB50TEV-Teri that is secreted. By contrast, deletion of the phoS gene showed no advantageous effect in secretion of CspB50TEV-Teri.

TABLE 1

| Strain | Relative intensity |
| --- | --- |
| YDK010/pPKK50TEV-Teri | 1.0 |
| YDK0107/pPKK50TEV-Teri | 13.2 |
| YDK010::phoS(W302C)/pPKK50TEV-Teri | 12.5 |
| YDK010ΔphoS/pPKK50TEV-Teri | 0.2 |

According to Appl. Environ. Microbiol., 94, 1131-1150 (2012), the region having positions 266-330 of the PhoS protein of the *C. glutamicum* ATCC13032 strain is considered to be a HisKA domain, and the HisKA domain contains a histidine residue that is autophosphorylated. Because the tryptophan residue at position 302 is present in the HisKA domain, the amino acid sequences of HisKA domains of PhoS homologues of various *Corynebacterium* bacteria were compared by alignment. FIG. 2 shows an alignment comparison of the amino acid sequences of HisKA domains of PhoS proteins from strains *C. glutamicum* YDK0107, *C. glutamicum* YDK010, and *C. glutamicum* ATCC13869 predicted from the nucleotide sequences analyzed with Big-Dye® Terminator v3.1 Cycle Sequencing Kit (Applied Biosystems) and 3130 Genetic Analyzer (Applied Biosystems), as well as the amino acid sequences of HisKA domains of PhoS homologues from strains *C. glutamicum* ATCC13032 (Genbank Accession No. NP_601807), *C. glutamicum* ATCC14067 (Genbank Accession No. KEI24167), *C. callunae* (Genbank Accession No. WP_015652043), *C. crenatum* (Genbank Accession No. WP_031512002), and *C. efficiens* (Genbank Accession No. WP_006769148). The homologues have a homology of 70% or more from database by BLAST search using the amino acid sequence of SEQ ID NO: 4 as the query sequence. In FIG. 2, the amino acid residue at position 302 is indicated. As a result, it was revealed that the tryptophan residue at position 302 is conserved in *Corynebacterium* bacteria, except in the YDK0107 strain. While the PhoS protein is known to be a sensor kinase as a part of a two-component regulatory system, the effect of this protein on secretory production of a heterologous protein has not been reported. Furthermore, due to the highly conserved nature of the amino acid at position 302, a mutation at this residue would not be expected to have an effect on the secretion amount of a heterologous protein.

Example 3: Secretory Production of Liver-type Fatty Acid-binding Protein (LFABP) Fused with Mature CspB N-terminal Amino Acid Residues Using CspB Signal Sequence in PhoS(W302C)-mutant Strain (1) Construction of Secretory Expression Plasmid of Liver-type Fatty Acid-binding Protein (LFABP) Fused with the N-Terminal 6 Amino Acid Residues of CspB Mature Protein The amino acid sequence of liver-type fatty acid-binding protein of human (hereinafter, referred to as LFABP) has already been determined (Genbank Accession No. NP_001434). This amino acid sequence is shown as SEQ ID NO: 11. Considering the codon frequency of *C. glutamicum*, a nucleotide sequence encoding LFABP was designed. In addition, a fusion protein (hereinafter, referred to as CspB6Xa-LFABP) of the CspB signal peptide 30 amino acid residues of the *C. glutamicum* ATCC13869 strain, the N-terminal 6 amino acid residues of CspB mature protein of the same strain, the Factor Xa protease recognition sequence IEGR, and LFABP, and a nucleotide sequence encoding the fusion protein were designed. The designed nucleotide sequence encoding the fusion protein is shown as SEQ ID NO: 12, and the amino acid sequence of the fusion protein is shown as SEQ ID NO: 13.

Then, an expression cassette of CspB6Xa-LFABP was synthesized, in which the promoter of cspB gene of the *C. glutamicum* ATCC13869 strain was linked upstream of the DNA of SEQ ID NO: 12, and a KpnI site was added at both the 5'-side and 3'-side termini. The synthesized DNA fragment was treated with the restriction enzyme KpnI and inserted at a KpnI site in pPK4 disclosed in Japanese Patent Laid-open (Kokai) No. 9-322774, to construct pPK4_CspB6Xa-LFABP, which is a secretory expression plasmid of CspB6Xa-LFABP. As a result of nucleotide sequencing of the inserted fragment, it was confirmed that the expected gene encoding CspB6Xa-LFABP was constructed. Nucleotide sequencing was carried out with Big-Dye® Terminator v3.1 Cycle Sequencing Kit (Applied Biosystems) and 3130 Genetic Analyzer (Applied Biosystems).

(2) Secretory Expression Liver-type Fatty Acid-binding Protein (LFABP) Fused with N-terminal 6 Amino Acid Residues of CspB Mature Protein The *C. glutamicum* YDK010 strain disclosed in WO2002/081694 and the YDK010::phoS(W302C) strain constructed in Example 1(3) were each transformed with pPK4_CspB6Xa-LFABP constructed in Example 3(1), which is a secretory expression plasmid of LFABP fused with the N-terminal 6 amino acid residues of mature CspB and the Factor Xa protease recognition sequence IEGR, to obtain strains YDK010/pPK4_CspB6Xa-LFABP and YDK010::phoS(W302C)/pPK4_CspB6Xa-LFABP.

The obtained transformants were each cultured on MMTG liquid medium (120 g of glucose, 3 g of $MgSO_4.7H_2O$, 30 g of $(NH_4)_2SO_4$, 1.5 g of $KH_2PO_4$, 0.03 g of $FeSO_4.7H_2O$, 0.03 g of $MnSO_4.5H_2O$, 0.45 mg of thiamine hydrochloride, 0.45 mg of biotin, 0.15 g of DL-methionine, 0.2 g (as total nitrogen) of soybean hydrolysate solution obtained with HCl, and 50 g of $CaCO_3$, filled up with water to 1 L, and adjusted to pH7.0) containing 25 mg/L of kanamycin at 30° C. for 72 hr. After completion of the culture, 6.5 µL of each culture supernatant obtained by centrifugation was subjected to reduced SDS-PAGE, and then staining was carried out with Quick-CBB (Wako Pure Chemical Industries).

Figure 3:
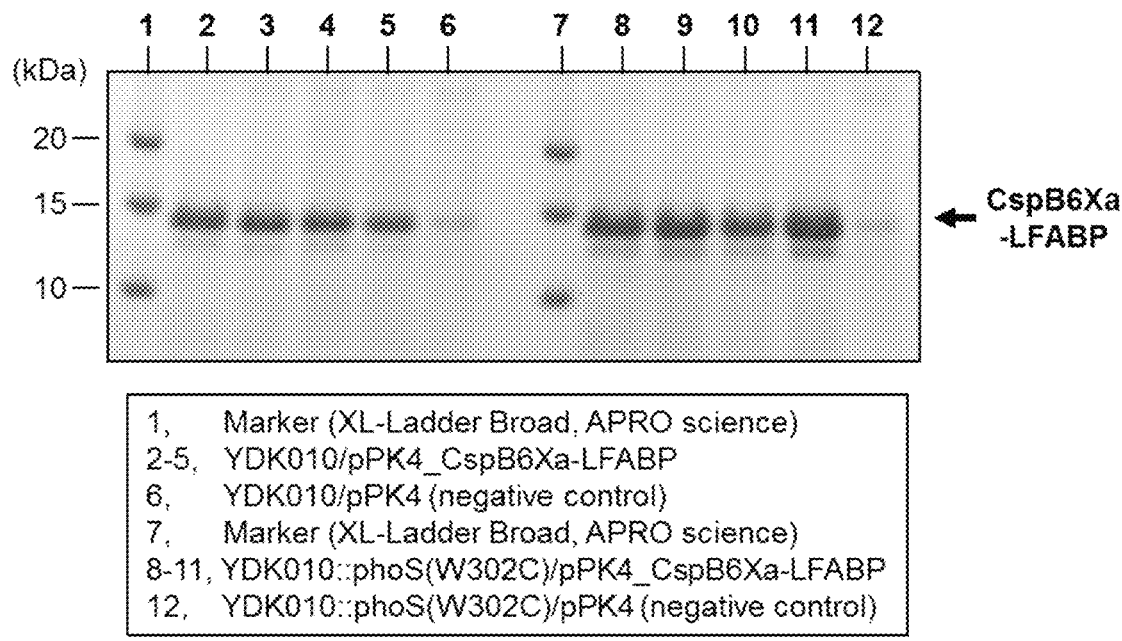
FIG. 3 is a photograph showing the results of SDS-PAGE observed upon expressing CspB6Xa-LFABP (LFABP fused with CspB signal sequence and mature CspB N-terminal sequence) in the *C. glutamicum* YDK010 strain and PhoS (W302C)-mutant strain thereof.

As a result, a band indicating a protein having the molecular weight of CspB6Xa-LFABP was densely detected in the YDK010::phoS(W302C) strain, as compared with the YDK010 strain, and hence, it was confirmed that the secretion amount of CspB6Xa-LFABP was significantly improved in the YDK010::phoS(W302C) strain (FIG. 3). After the staining, the band intensity of CspB6Xa-LFABP was digitized with image analysis software Multi Gauge (FUJIFILM), and the average value of the band intensity observed upon expressing CspB6Xa-LFABP in the YDK010::phoS(W302C) strain was calculated as a relative value based on the average value of the band intensity observed upon expressing CspB6Xa-LFABP in the YDK010 strain which was taken as 1. As a result, it was confirmed that the secretion amount of CspB6Xa-LFABP was improved about 1.9-fold in the YDK010::phoS(W302C) strain, as compared with the YDK010 strain (Table 2). From this, it was revealed that the PhoS(W302C) mutation is an effective mutation that leads to a significant improvement of the secretion amount also in secretion of CspB6Xa-LFABP.

TABLE 2

| Strain | Relative intensity |
|---|---|
| YDK010/pPK4_CspB6Xa-LFABP | 1.0 |
| YDK010::phoS(W302C)/pPK4_CspB6Xa-LFABP | 1.9 |

Example 4: Secretory Production of Exenatide Precursor (ExCP) Fused with Mature CspB N-Terminal Amino Acid Residues Using CspB Signal Sequence in PhoS(W302C)-mutant Strain (1) Construction of Secretory Expression Plasmid of Exenatide Precursor (ExCP) Fused with N-terminal 6 Amino Acid Residues of CspB Mature Protein The amino acid sequence of a physiologically active peptide exenatide has already been determined (Genbank Accession No. P26349). Because the activated exenatide is amidated at the C-terminus, a precursor having a Cys-Pro dipeptide added at the C-terminus (hereinafter, referred to as ExCP) is shown as SEQ ID NO: 14. Considering the codon frequency of *C. glutamicum*, a nucleotide sequence encoding ExCP was designed. In addition, a fusion protein was designed (hereinafter, referred to as CspB6TEV-ExCP) having 30 amino acid residues of the CspB signal peptide of the *C. glutamicum* ATCC13869 strain, the N-terminal 6 amino acid residues of CspB mature protein of the same strain, the ProTEV protease recognition sequence ENLYFQ, and ExCP. A nucleotide sequence encoding the fusion protein was also designed. The nucleotide sequence encoding the fusion protein is shown as SEQ ID NO: 15, and the amino acid sequence of the fusion protein is shown as SEQ ID NO: 16.

Then, an expression cassette of CspB6TEV-ExCP was synthesized, in which the promoter of cspB gene of the *C. glutamicum* ATCC13869 strain was linked upstream of the DNA of SEQ ID NO: 15, and a KpnI site was added at both the 5'-side and 3'-side termini. The synthesized DNA fragment was treated with the restriction enzyme KpnI and inserted at a KpnI site of pPK4 disclosed in Japanese Patent Laid-open (Kokai) No. 9-322774, to construct pPK4_CspB6TEV-ExCP, which is a secretory expression plasmid of CspB6TEV-ExCP. As a result of nucleotide sequencing of the inserted fragment, it was confirmed that the expected gene encoding CspB6TEV-ExCP was constructed. Nucleotide sequencing was carried out with Big-Dye® Terminator v3.1 Cycle Sequencing Kit (Applied Biosystems) and 3130 Genetic Analyzer (Applied Biosystems).

(2) Secretory Expression Exenatide Precursor (ExCP) Fused with N-terminal 6 Amino Acid Residues of CspB Mature Protein The *C. glutamicum* YDK010 strain disclosed in WO2002/081694 and the YDK010::phoS(W302C) strain constructed in Example 1(3) were each transformed with pPK4_CspB6TEV-ExCP constructed in Example 4(1), which is a secretory expression plasmid of ExCP fused with the N-terminal 6 amino acid residues of mature CspB and the ProTEV protease recognition sequence, to obtain strains YDK010/pPK4_CspB6TEV-ExCP and YDK010::phoS (W302C)/pPK4_CspB6TEV-ExCP.

The obtained transformants were each cultured on MMTG liquid medium (120 g of glucose, 3 g of $MgSO_4.7H_2O$, 30 g of $(NH_4)_2SO_4$, 1.5 g of $KH_2PO_4$, 0.03 g of $FeSO_4.7H_2O$, 0.03 g of $MnSO_4.5H_2O$, 0.45 mg of thiamine hydrochloride, 0.45 mg of biotin, 0.15 g of DL-methionine, 0.2 g (as total nitrogen) of soybean hydrolysate solution obtained with HCl, and 50 g of $CaCO_3$, filled up with water to 1 L, and adjusted to pH7.0) containing 25 mg/L of kanamycin at 30° C. for 72 hr. After completion of the culture, 6.5 μL of each culture supernatant obtained by centrifugation was subjected to reduced SDS-PAGE, and then staining was carried out with Quick-CBB (Wako Pure Chemical Industries).

Figure 4:
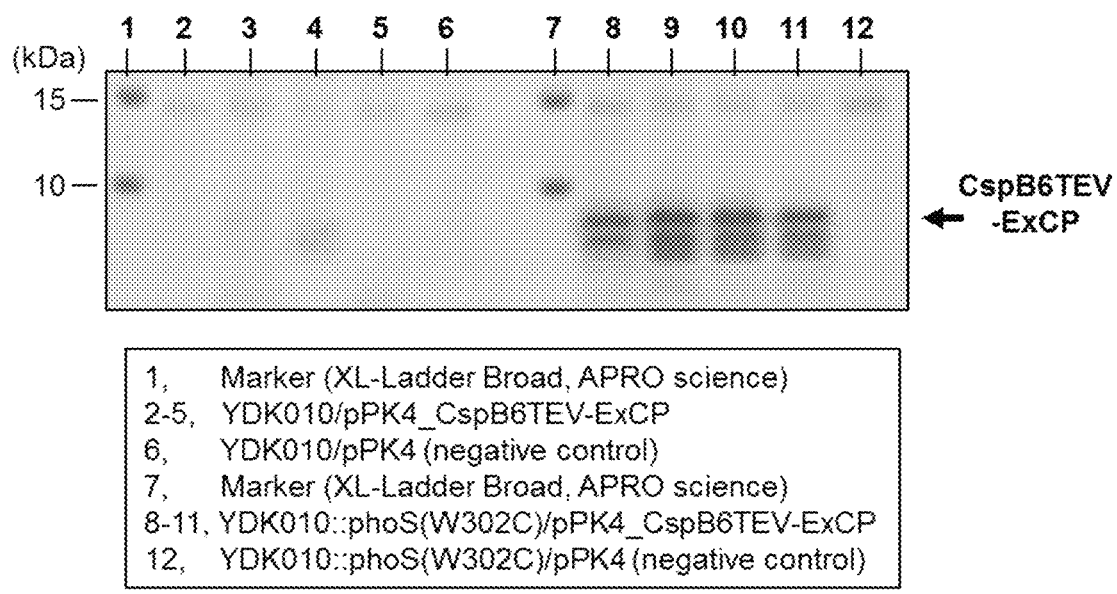
FIG. 4 is a photograph showing the results of SDS-PAGE observed upon expressing CspB6TEV-ExCP (Exenatide fused with CspB signal sequence and mature CspB N-terminal sequence) in the *C. glutamicum* YDK010 strain and PhoS(W302C)-mutant strain thereof.

As a result, a dense band indicating a protein having the molecular weight of CspB6TEV-ExCP was detected in the YDK010::phoS(W302C) strain while the same band was barely detectable in the YDK010 strain, and hence, it was confirmed that the secretion amount of CspB6TEV-ExCP was significantly improved in the YDK010::phoS(W302C) strain (FIG. 4). In addition, the secretion amount of CspB6TEV-ExCP observed for each of the strains was averaged and shown in Table 3 with scores ranging from "±" to "+++". From this, it was revealed that the PhoS(W302C) mutation is an effective mutation that leads to a significant improvement of the secretion amount in secretion of CspB6TEV-ExCP.

TABLE 3

| Strain | Secretion amount |
| --- | --- |
| YDK010/pPK4_CspB6TEV-ExCP | ± |
| YDK010::phoS(W302C)/pPK4_CspB6TEV-ExCP | +++ |

From Examples 2-4, it was concluded that the secretory expression amount of an objective protein can be significantly improved by using the PhoS(W302C)-mutant strain regardless of the type of protein to be expressed, the number of N-terminal amino acid residues of mature CspB that fused with the protein, and the type of protease recognition sequence, when using the Sec secretion system in the CspB fusion method as disclosed in WO2013/062029. This is a method for expressing a heterologous protein fused with N-terminal amino acid residues of mature CspB, Example 5: Secretory Production of Protransglutaminase Using TorA Signal Sequence in PhoS(W302C)-mutant Strain (1) Construction of Co-Expression Plasmid of tatABC Genes Encoding Tat Secretion System and Gene Encoding Protransglutaminase Having an Added TorA Signal Sequence (a) Construction of pPK5, which is a Vector Based on the pPK4 Vector, but with a Modified NaeI Recognition Sequence pPK4 is disclosed in Japanese Patent Laid-open (Kokai) No. 9-322774 and contains the recognition sequence of restriction enzyme NaeI, which is gccggc. Primers SEQ ID NOS: 17 and 18 were synthesized to contain a sequence gcaggc, which is modified as compared to the NaeI recognition sequence gccggc, and adjacent sequences of pPK4. Then, PCR was carried out by using SEQ ID NOS: 17 and 18 as primers, and pPK4 as the template, to amplify a full-length plasmid of about 5.6 kbp. PCR was carried out with Pyrobest® DNA polymerase (Takara Bio), and the reaction conditions were 95° C. for 5 min, and 12 cycles of (95° C. for 30 sec. 55° C. for 1 min, and 72° C. for 12 min).

The PCR product was then treated with restriction enzyme DpnI, to digest the methylated template DNA. The non-methylated plasmid obtained after the DpnI digestion was introduced into competent cells of *E. coli* JM109 (Takara Bio), to obtain the plasmid. As a result of nucleotide sequencing, it was confirmed that the plasmid contained the modified NaeI recognition sequence. Nucleotide sequencing was carried out with BigDye® Terminator v3.1 Cycle Sequencing Kit (Applied Biosystems) and 3130 Genetic Analyzer (Applied Biosystems). The thus-obtained vector with the modified NaeI recognition sequence was designated as pPK5.

(b) Construction of pPK5-tatABC, which is a pPK5 Vector Containing the tatABC Genes PCR was then carried out by using SEQ ID NOS: 19 and 20 as primers, and pVtatABC disclosed in WO2005/103278, which is an amplification plasmid of Tat secretion system, as the template, to amplify a DNA fragment of about 3.7 kbp containing a sequence encoding the tatABC genes. The SEQ ID NO: 20 primer was designed to contain the recognition sequences of restriction enzymes KpnI and ApaI. PCR was carried out with Pyrobest® DNA polymerase (Takara Bio), and the reaction conditions were according to the protocol recommended by the manufacturer. This DNA fragment was phosphorylated at the termini with a BKL Kit (Takara Bio), treated with KpnI, blunt-ended with BKL Kit (TakaraBio), and inserted into the pPK5 vector that was dephosphorylated at the termini with CIAP (Takara Bio), to construct pPK5-tatABC, which is a vector containing the tatABC genes. A ligation reaction was carried out with DNA Ligation Kit Ver.2.1 (Takara Bio), and the reaction conditions were according to the protocol recommended by the manufacturer. As a result of nucleotide sequencing of the inserted fragment, it was confirmed that the objective genes were inserted. Nucleotide sequencing was carried out with Big- Dye® Terminator v3.1 Cycle Sequencing Kit (Applied Biosystems) and 3130 Genetic Analyzer (Applied Biosystems).

(c) Construction of pPK6, a pPK5-tatABC Vector with Modified KpnI and XbaI Recognition Sequences in the tatABC Genes In the tatABC gene region in the pPK5-tatABC plasmid constructed in (b), the recognition sequences for restriction enzymes KpnI and XbaI, ggtacc and tctcaga, respectively, are each present. Primers SEQ ID NOS: 21 and 22 were synthesized to contain a sequence ggaacc and adjacent sequences of pPK5-tatABC. Primers SEQ ID NOS: 23 and 24 were synthesized to contain a sequence tgtaga and adjacent sequences of pPK5-tatABC.

First, to modify the KpnI recognition sequence in the tatABC gene region, PCR was carried out by using SEQ ID NOS: 21 and 22 as primers, and pPK5-tatABC as the template, to amplify a full-length plasmid of about 9.4 kbp. PCR was carried out with Pyrobest® DNA polymerase (Takara Bio), and the reaction conditions were 95° C. for 5 min, and 12 cycles of (95° C. for 30 sec. 55° C. for 1 min, and 72° C. for 12 min).

The PCR product was then treated with restriction enzyme DpnI, to digest the methylated template DNA. The non-methylated plasmid obtained after the DpnI digestion was introduced into competent cells of E. coli JM109 (Takara Bio), to obtain the plasmid. Thus, pPK5-tatABCΔKpnI, which is a vector with modified KpnI recognition sequences in the tatABC gene region was constructed.

Then, to modify the XbaI recognition sequence in the tatABC gene region, PCR was carried out by using SEQ ID NOS: 23 and 24 as primers, and pPK5-tatABCΔKpnI as the template, to amplify a full-length plasmid of about 9.4 kbp. PCR was carried out with Pyrobest® DNA polymerase (Takara Bio), and the reaction conditions were 95° C. for 5 min, and 12 cycles of (95° C. for 30 sec. 55° C. for 1 min, and 72° C. for 12 min).

The PCR product was then treated with restriction enzyme DpnI, to digest the methylated template DNA. The non-methylated plasmid obtained after the DpnI digestion was introduced into competent cells of E. coli JM109 (Takara Bio), to obtain the plasmid. Thus, pPK5-tatABCΔKpnIΔXbaI, which is a vector with modified XbaI recognition sequences in the tatABC gene region was constructed. As a result of nucleotide sequencing, it was confirmed that the objective genes were constructed. Nucleotide sequencing was carried out with BigDye® Terminator v3.1 Cycle Sequencing Kit (Applied Biosystems) and 3130 Genetic Analyzer (Applied Biosystems).

Figure 5:
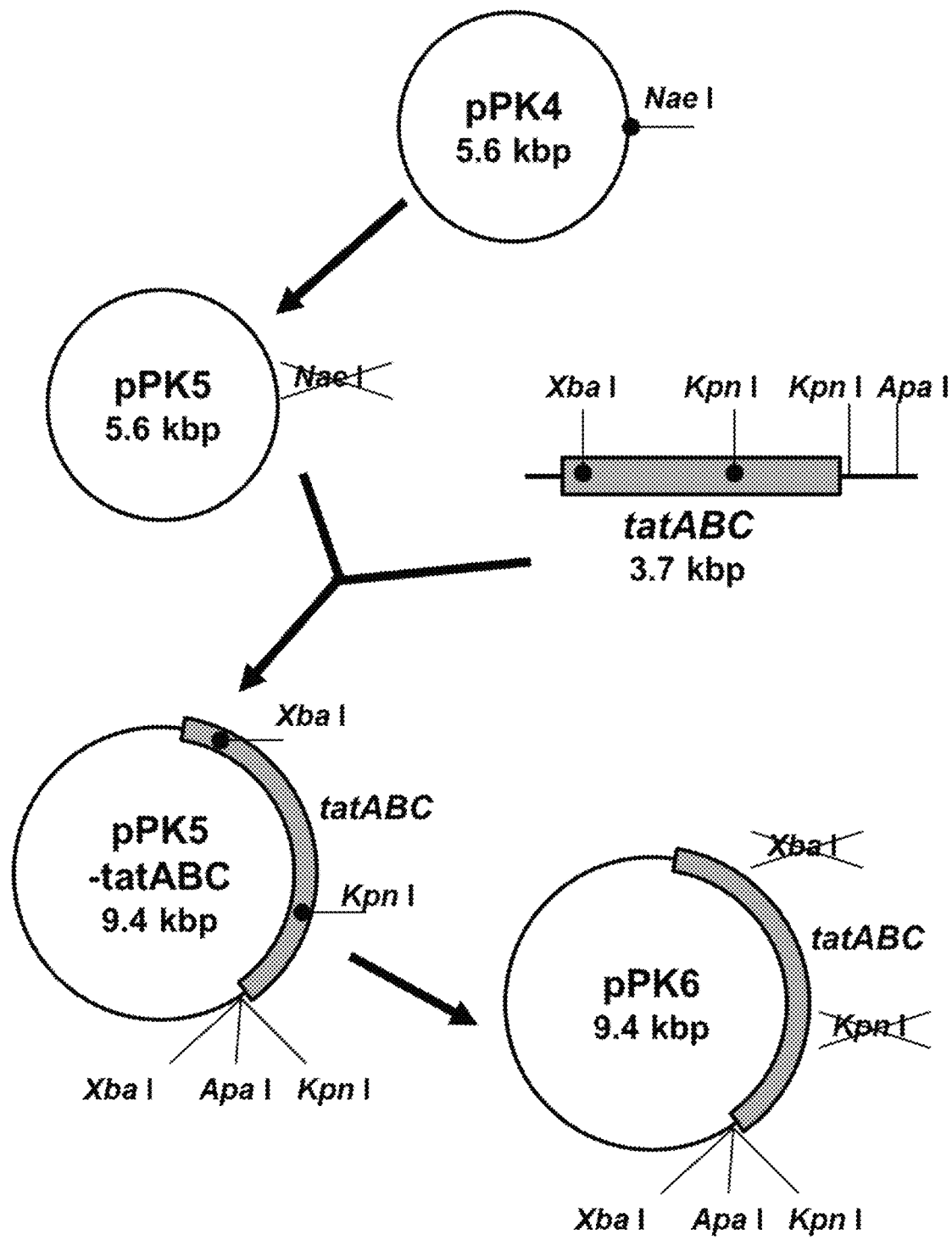
FIG. 5 is a diagram showing a construction scheme of pPK6 vector.

The thus-obtained vector carrying the tatABC genes based on the pPK4 vector was designated as pPK6. The construction scheme of pPK6 from pPK4 is shown in FIG. 5. To amplify the TatABC secretion system during secretory expression of a protein using the Tat system, two plasmids, that is, a secretory expression plasmid of an objective protein, and pVtatABC, which is an amplification plasmid of the Tat secretion system, were necessarily used in the method of WO2005/103278. By contrast, use of the pPK6 vector enabled the expression of an objective protein and amplification of the TatABC secretion system in one plasmid.

(d) Construction of pPK6-TorAss, which is a pPK6 Vector Containing the cspB Promoter and DNA Encoding a TorA Signal Sequence PCR was carried out by using SEQ ID NOS: 25 and 26 as primers, and pPTGFP disclosed in Appl. Environ. Microbiol., 72, 7183-7192(2006) as the template, to amplify a DNA fragment of about 0.7 kbp containing a promoter region of cspB gene of the C. glutamicum ATCC13869 strain and a nucleotide sequence encoding the TorA signal sequence of E. coli. The primer of SEQ ID NO: 26 was designed to contain the recognition sequences of restriction enzymes ApaI and NaeI. PCR was carried out with Pyrobest® DNA polymerase (Takara Bio), and the reaction conditions were according to the protocol recommended by the manufacturer. This DNA fragment was treated with KpnI and ApaI, and inserted into the KpnI-ApaI site of the pPK6 vector constructed in (c), to construct pPK6-TorAss, which is a vector carrying the promoter region of cspB gene of the C. glutamicum ATCC13869 strain and the nucleotide sequence encoding the TorA signal sequence of E. coli. A ligation reaction was carried out with DNA Ligation Kit Ver.2.1 (Takara Bio), and the reaction conditions were according to the protocol recommended by the manufacturer. As a result of nucleotide sequencing of the inserted fragment, it was confirmed that the expected gene was inserted. Nucleotide sequencing was carried out with Big-Dye® Terminator v3.1 Cycle Sequencing Kit (Applied Biosystems) and 3130 Genetic Analyzer (Applied Biosystems).

(e) Construction of Secretory Expression Vector of Protransglutaminase Using the pPK6-TorAss Vector PCR was carried out by using SEQ ID NOS: 27 and 28 as primers, and pPKSPTG1 disclosed in WO2001/23591, which is a secretory expression vector of protransglutaminase, as the template, to amplify a DNA fragment of about 1.1 kbp encoding protransglutaminase. The primer of SEQ ID NO: 28 was designed to contain the recognition sequence of restriction enzyme XbaI. PCR was carried out with Pyrobest® DNA polymerase (Takara Bio), and the reaction conditions were according to the protocol recommended by the manufacturer. This DNA fragment was treated with XbaI, and inserted into the NaeI-XbaI site of the pPK6-TorAss vector constructed in (d), to construct pPK6_T_PTG, which is a co-expression vector of the TatABC secretion system and protransglutaminase with the added TorA signal sequence. A ligation reaction was carried out with DNA Ligation Kit Ver.2.1 (Takara Bio), and the reaction conditions were according to the protocol recommended by the manufacturer. As a result of nucleotide sequencing of the inserted fragment, it was confirmed that the expected gene was inserted. Nucleotide sequencing was carried out with BigDye(R) Terminator v3.1 Cycle Sequencing Kit (Applied Biosystems) and 3130 Genetic Analyzer (Applied Biosystems).

Figure 6:
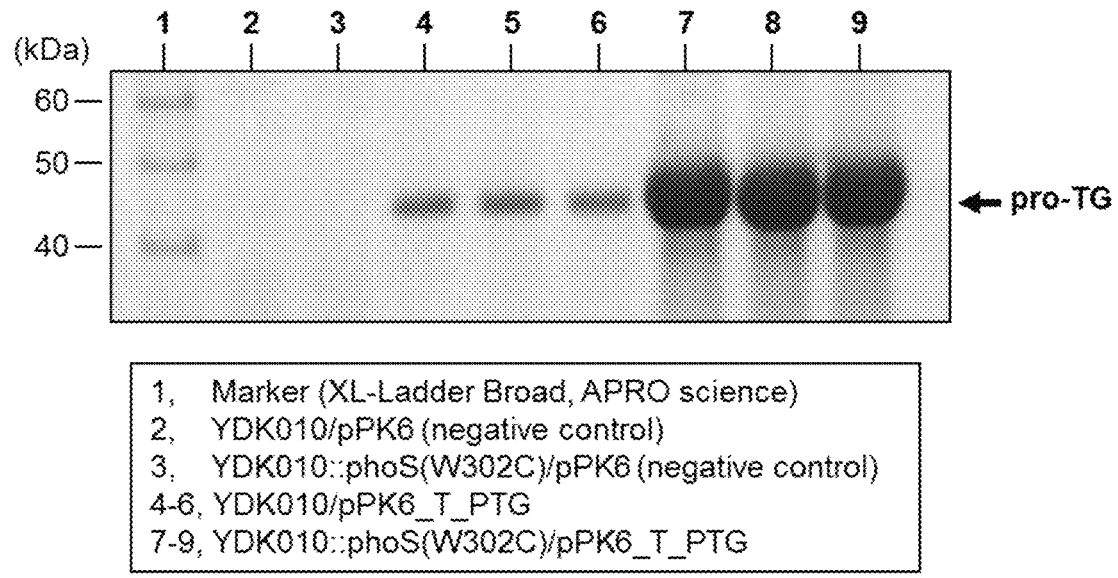
FIG. 6 is a photograph showing results of SDS-PAGE observed upon expressing protransglutaminase fused with *E. coli* TorA signal sequence in the *C. glutamicum* YDK010 strain and PhoS(W302C)-mutant strain thereof.

(2) Secretory Expression of Protransglutaminase Using a TorA Signal Sequence in the YDK010 and YDK010::phoS (W302C) Strains The C. glutamicum YDK010 strain disclosed in WO2002/081694 and the YDK010::phoS(W302C) strain obtained in Example 1(3) were each transformed with pPK6_T_PTG obtained in Example 5(1)(e), which is a secretory expression plasmid of protransglutaminase, to obtain strains YDK010/pPK6_T_PTG and YDK010::phoS(W302C)/pPK6_T_PTG. The obtained transformants were each cultured on MMTG liquid medium (120 g of glucose, 3 g of $MgSO_4.7H_2O$, 30 g of $(NH_4)_2SO_4$, 1.5 g of $KH_2PO_4$, 0.03 g of $FeSO_4.7H_2O$, 0.03 g of $MnSO_4.5H_2O$, 0.45 mg of thiamine hydrochloride, 0.45 mg of biotin, 0.15 g of DL-methionine, 0.2 g (as total nitrogen) of soybean hydrolysate solution obtained with HCl, and 50 g of $CaCO_3$, filled up with water to 1 L, and adjusted to pH7.0) containing 25 mg/L of kanamycin at 30° C. for 72 hr. After completion of the culture, 5 μL of each of the culture supernatants obtained by centrifugation was subjected to reduced SDS-PAGE, and then staining was carried out with Quick-CBB (Wako Pure Chemical Industries). As a result, the secretion amount of protransglutaminase was significantly improved in the YDK010::phoS (W302C) strain, as compared with the YDK010 strain (FIG. 6). After the staining, the band intensity of protransglutaminase was digitized with image analysis software Multi Gauge (FUJIFILM), and the average value of the band intensity observed upon expressing protransglutaminase in the YDK010::phoS(W302C) strain was calculated as a relative value based on the average value of the band intensity observed upon expressing protransglutaminase in the YDK010 strain which was taken as 1. As a result, it was confirmed that the secretion amount of protransglutaminase was improved about 7.2-fold in the YDK010::phoS (W302C) strain, as compared with the YDK010 strain (Table 4). From this, it was revealed that the PhoS(W302C) mutation is an effective mutation that leads to a significant improvement of the amount of protransglutaminase using the TorA signal sequence that is secreted.

TABLE 4

| Strain | Relative intensity |
|---|---|
| YDK010/pPK6_T_PTG | 1.0 |
| YDK010::phoS(W302C)/pPK6_T_PTG | 7.2 |

Example 6: Secretory Production of Protein Glutaminase with a Pro-structure Moiety Using a TorA Signal Sequence in the PhoS(W302C)-mutant Strain (1) Construction of Co-expression Plasmid Containing the tatABC Genes Encoding the Tat Secretion System and a Gene Expressing the Protein Glutaminase with a Pro-structure Moiety and an Added TorA Signal Sequence PCR was carried out by using SEQ ID NOS: 29 and 30 as primers, and pPKT-PPG disclosed in WO2005/103278, which is an expression plasmid for protein glutaminase with a pro-structure moiety, as the template, to amplify a promoter region of cspB gene of the *C. glutamicum* ATCC13869 strain, and a nucleotide sequence operably linked downstream from the promoter and encoding a fusion protein of the TorA signal sequence of *E. coli* and protein glutaminase with a pro-structure moiety of *Chryseobacterium proteolyticum*. The primers of SEQ ID NO: 29 and 30 were each designed to contain the recognition sequence of restriction enzyme XbaI. PCR was carried out with Pyrobest® DNA polymerase (Takara Bio), and the reaction conditions were according to the protocol recommended by the manufacturer. This DNA fragment was treated with XbaI, and inserted into the XbaI site of the pPK6 vector constructed in Example 5(1), to construct pPK6_T_PPG, which is a co-expression vector of the TatABC secretion system and protein glutaminase with a pro-structure moiety and the added TorA signal sequence. A ligation reaction was carried out with DNA Ligation Kit <Mighty Mix> (Takara Bio), and the reaction conditions were according to the protocol recommended by the manufacturer. As a result of nucleotide sequencing of the inserted fragment, it was confirmed that the objective gene was inserted. Nucleotide sequencing was carried out with BigDye® Terminator v3.1 Cycle Sequencing Kit (Applied Biosystems) and 3130 Genetic Analyzer (Applied Biosystems).

Figure 7:
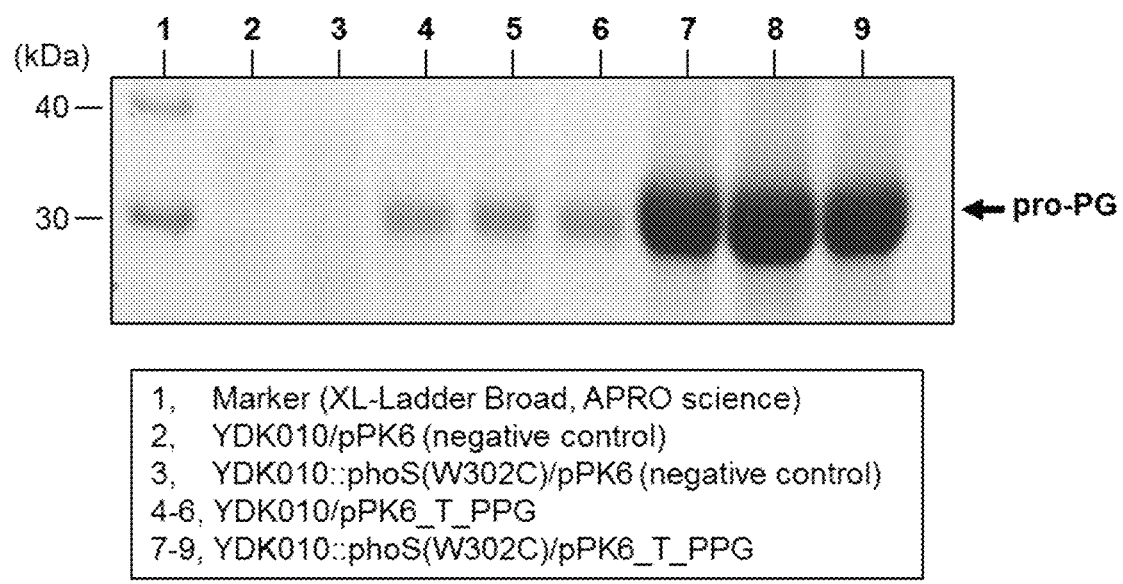
FIG. 7 is a photograph showing results of SDS-PAGE observed upon expressing protein glutaminase comprising a pro-structure moiety and fused with *E. coli* TorA signal sequence in the *C. glutamicum* YDK010 strain and PhoS (W302C)-mutant strain thereof.

(2) Secretory Expression of Glutaminase with a Pro-Structure Moiety Using TorA Signal Sequence in the YDK010 and YDK010::phoS(W302C) Strains The *C. glutamicum* YDK010 strain disclosed in WO2002/081694 and the YDK010::phoS(W302C) strain obtained in Example 1(3) were each transformed with pPK6_T_PPG obtained in Example 6(1), which is a secretory expression plasmid for glutaminase with a pro-structure moiety, to obtain strains YDK010/pPK6_T_PPG and YDK010:PhoS (W302C)/pPK6_T_PPG. The obtained transformants were each cultured on MMTG liquid medium (120 g of glucose, 3 g of MgSO$_4$.7H$_2$O, 30 g of (NH$_4$)$_2$SO$_4$, 1.5 g of KH$_2$PO$_4$, 0.03 g of FeSO$_4$.7H$_2$O, 0.03 g of MnSO$_4$.5H$_2$O, 0.45 mg of thiamine hydrochloride, 0.45 mg of biotin, 0.15 g of DL-methionine, 0.2 g (as total nitrogen) of soybean hydrolysate solution obtained with HCl, and 50 g of CaCO$_3$, filled up with water to 1 L, and adjusted to pH7.0) containing 25 mg/L of kanamycin at 30° C. for 72 hr. After completion of the culture, 5 of each culture supernatant obtained by centrifugation was subjected to reduced SDS-PAGE, and then staining was carried out with Quick-CBB (Wako Pure Chemical Industries). As a result, the amount of glutaminase with a pro-structure moiety that was secreted was significantly improved in the YDK010::phoS(W302C) strain, as compared with the YDK010 strain (FIG. 7). After the staining, the band intensity of the glutaminase with a pro-structure moiety was digitized with image analysis software Multi Gauge (FUJIFILM), and the average value of the band intensity was calculated as a relative value based on the average value of the band intensity observed upon expressing glutaminase with a pro-structure moiety in the YDK010 strain, which was taken as 1. As a result, it was confirmed that the amount of glutaminase with a pro-structure moiety that was secreted was improved about 8.3-fold in the YDK010::phoS(W302C) strain, as compared with the YDK010 strain (Table 5). From this, it was revealed that the PhoS(W302C) mutation is an effective mutation that leads to a significant improvement of the amount of glutaminase with a pro-structure moiety using the TorA signal sequence that can be secreted.

TABLE 5

| Strain | Relative intensity |
|---|---|
| YDK010/pPK6_T_PPG | 1.0 |
| YDK010::phoS(W302C)/pPK6_T_PPG | 8.3 |

Example 7: Secretory Production of Isomaltodextranase Using IMD Signal Sequence in PhoS(W302C)-mutant Strain (1) Construction of Co-expression Plasmid Containing the tatABC Genes Encoding Tat Secretion System and Gene Encoding Isomaltodextranase PCR was carried out by using SEQ ID NOS: 29 and 31 as primers, and pPKI-IMD disclosed in WO2005/103278, which is an expression plasmid for isomaltodextranase, as the template, to amplify the promoter region of the cspB gene of the *C. glutamicum* ATCC13869 strain, and an IMD gene sequence of *Arthrobacter globiformis* (including a coding region of the IMD signal sequence) operably linked downstream from the promoter. The primers of SEQ ID NO: 29 and 31 were each designed to contain the recognition sequence of restriction enzyme XbaI. PCR was carried out with PrimeSTAR® GXL DNA Polymerase (Takara Bio), and the reaction conditions were according to the protocol recommended by the manufacturer. This DNA fragment was treated with XbaI, and inserted into the XbaI site of the pPK6 vector constructed in Example 5(1), to construct pPK6_I_IMD, which is a co-expression vector for the TatABC secretion system and isomaltodextranase including the IMD signal sequence. A ligation reaction was carried out with the DNA Ligation Kit <Mighty Mix> (Takara Bio), and the reaction conditions were according to the protocol recommended by the manufacturer. As a result of nucleotide sequencing of the inserted fragment, it was confirmed that the objective gene was inserted. Nucleotide sequencing was carried out with BigDye® Terminator v3.1 Cycle Sequencing Kit (Applied Biosystems) and 3130 Genetic Analyzer (Applied Biosystems).

Figure 8:
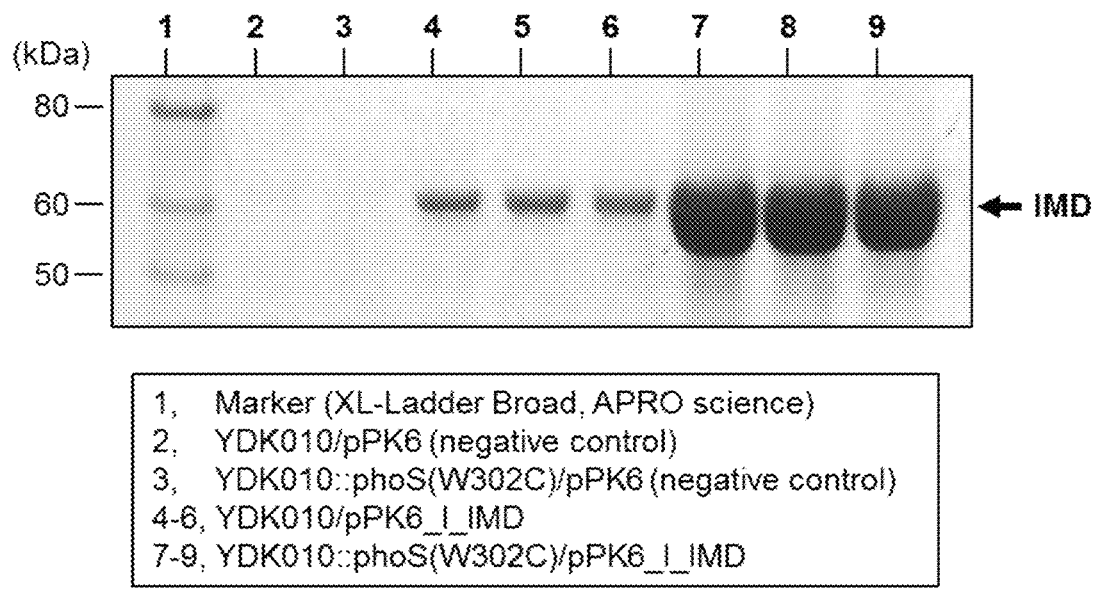
FIG. 8 is a photograph showing results of SDS-PAGE observed upon expressing *Arthrobacter globiformis* isomaltodextranase including a signal sequence in the *C. glutamicum* YDK010 strain and PhoS(W302C)-mutant strain thereof.

(2) Secretory Expression of Isomaltodextranase Using IMD Signal Sequence in the YDK010 and YDK010::phoS (W302C) Strains The C. glutamicum YDK010 strain disclosed in WO2002/081694 and the YDK010::phoS(W302C) strain obtained in Example 1(3) were each transformed with pPK6_I_IMD obtained in Example 7(1), which is an expression plasmid of isomaltodextranase, to obtain strains YDK010/pPK6_I_IMD and YDK010::phoS(W302C)/pPK6_I_IMD. The obtained transformants were each cultured on MMTG liquid medium (120 g of glucose, 3 g of $MgSO_4 \cdot 7H_2O$, 30 g of $(NH_4)_2SO_4$, 1.5 g of $KH_2PO_4$, 0.03 g of $FeSO_4 \cdot 7H_2O$, 0.03 g of $MnSO_4 \cdot 5H_2O$, 0.45 mg of thiamine hydrochloride, 0.45 mg of biotin, 0.15 g of DL-methionine, 0.2 g (as total nitrogen) of soybean hydrolysate solution obtained with HCl, and 50 g of $CaCO_3$, filled up with water to 1 L, and adjusted to pH7.0) containing 25 mg/L of kanamycin at 30° C. for 72 hr. After completion of the culture, 5 µL of each culture supernatant obtained by centrifugation was subjected to reduced SDS-PAGE, and then staining was carried out with Quick-CBB (Wako Pure Chemical Industries). As a result, the amount of secreted isomaltodextranase was significantly improved in the YDK010::phoS(W302C) strain, as compared with the YDK010 strain (FIG. 8). After the staining, the band intensity of isomaltodextranase was digitized with image analysis software Multi Gauge (FUJIFILM), and the average value of the band intensity observed upon expressing isomaltodextranase in the YDK010::phoS (W302C) strain was calculated as a relative value based on the average value of the band intensity observed upon expressing isomaltodextranase in the YDK010 strain, which was taken as 1. As a result, it was confirmed that the secretion amount of isomaltodextranase was improved to about 6.6-fold in the YDK010::phoS(W302C) strain, as compared with the YDK010 strain (Table 6). From this, it was revealed that the PhoS(W302C) mutation is an effective mutation that leads to a significant improvement of the amount of isomaltodextranase that can be secreted using the IMD signal sequence of A. globiformis.

TABLE 6

| Strain | Relative intensity |
| --- | --- |
| YDK010/pPK6_I_IMD | 1.0 |
| YDK010::phoS(W302C)/pPK6_I_IMD | 6.6 |

From Examples 5-7, it was revealed that, when using the Tat secretion system as disclosed in WO2005/103278 for secretory expression of a heterologous protein, the amount of an objective protein that is expressed by secretion can be significantly improved by using the PhoS(W302C)-mutant strain regardless of the type of protein to be expressed and the chosen signal sequence.

Hence, from Examples 2-7, it was revealed that the amount of an objective protein that can be secreted can be significantly improved by using the PhoS(W302C)-mutant strain regardless of the difference in the type of secretion pathway to be used, the type of signal sequence to be used, and the type of protein to be expressed.

Example 8: Functional Complementation of PhoS-deletion Strain Through Plasmid Amplification of phoS Gene (1) Construction of Amplification Plasmids of Wild-type phoS Gene and Mutant phoS(W302C) Gene (a) Construction of Amplification Plasmid for Wild-type phoS Gene PCR was carried out by using SEQ ID NOS: 32 and 33 as primers, and genomic DNA of the C. glutamicum YDK010 strain prepared with PurElute™ Genomic DNA Kit (EdgeBio) as the template, to amplify a region of about 1.5 kbp containing the wild-type phoS gene. PCR was carried out with Pyrobest® DNA polymerase (Takara Bio), and the reaction conditions were according to the protocol recommended by the manufacturer.

Then, the amplified DNA fragment of about 1.5 kbp was subject to agarose gel electrophoresis, an objective band was cut out, and the DNA fragment was collected from the gel with Wizard® SV Gel and PCR Clean-Up System (Promega). The collected DNA fragment was inserted at SmaI site of the pVC7 vector disclosed in Japanese Patent Laid-open (Kokai) No. 9-070291 by infusion reaction, which is a shuttle vector having a chloramphenicol resistance gene and that is capable of replicating in both E. coli and coryneform bacteria, to obtain pVphoS(WT), which is an amplification plasmid of the wild-type phoS gene. The infusion reaction was carried out with In-Fusion® HD Cloning Kit (Takara Bio), and the reaction conditions were according to the protocol recommended by the manufacturer. As a result of nucleotide sequencing of the inserted fragment, it was confirmed that the objective gene was inserted. Nucleotide sequencing was carried out with BigDye® Terminator v3.1 Cycle Sequencing Kit (Applied Biosystems) and 3130 Genetic Analyzer (Applied Biosystems).

(b) Construction of Amplification Plasmid of Mutant phoS(W302C) Gene

Similarly, PCR was carried out by using SEQ ID NOS: 32 and 33 as primers, and genomic DNA of the C. glutamicum YDK010::phoS(W302C) strain prepared with PurElute™ Genomic DNA Kit (EdgeBio) as the template, to amplify a region of about 1.5 kbp containing the mutant phoS (W302C) gene. PCR was carried out with Pyrobest® DNA polymerase (Takara Bio), and the reaction conditions were according to the protocol recommended by the manufacturer.

Then, the amplified DNA fragment of about 1.5 kbp was subject to agarose gel electrophoresis, an objective band was cut out, and the DNA fragment was collected from the gel with Wizard® SV Gel and PCR Clean-Up System (Promega). The collected DNA fragment was inserted at SmaI site of the pVC7 vector disclosed in Japanese Patent Laid-open (Kokai) No. 9-070291 by infusion reaction, to obtain pVphoS(W302C), which is an amplification plasmid of the mutant phoS(W302C) gene. The infusion reaction was carried out with In-Fusion® HD Cloning Kit (Takara Bio), and the reaction conditions were according to the protocol recommended by the manufacturer. As a result of nucleotide sequencing of the inserted fragment, it was confirmed that the expected gene was inserted. Nucleotide sequencing was carried out with BigDye® Terminator v3.1 Cycle Sequencing Kit (Applied Biosystems) and 3130 Genetic Analyzer (Applied Biosystems).

Figure 9:
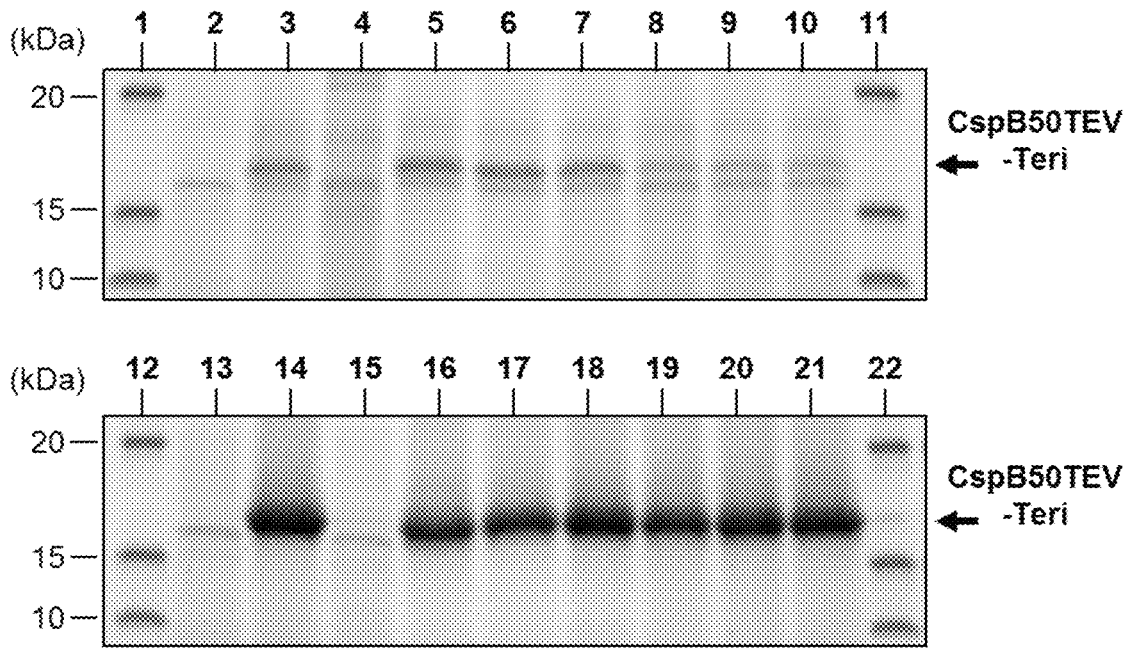
FIG. 9 is a photograph showing results of SDS-PAGE observed upon expressing CspB50TEV-Teri in PhoS-deletion strain of the *C. glutamicum* YDK010 strain, and PhoS-complemented strains thereof.

(2) Effect of Amplification of Wild-type phoS Gene or Mutant phoS(W302C) Gene on Secretory Expression of CspB50TEV-Teri Using PhoS-deletion Strain The YDK010ΔphoS strain constructed in Example 1(5) was transformed with pPKK50TEV-Teri disclosed in WO2014/126260 in combination with pVphoS(WT) or pVphoS(W302C) constructed in Example 8(1). In addition, as a control, the YDK010ΔphoS strain constructed in Example 1(5) was transformed with the pPK4 vector disclosed in Japanese Patent Laid-open (Kokai) No. 9-322774 in combination with pVphoS(WT) or pVphoS(W302C) constructed in Example 8(1). The obtained transformants were each cultured on MMTG liquid medium (120 g of glucose, 3 g of $MgSO_4.7H_2O$, 30 g of $(NH_4)_2SO_4$, 1.5 g of $KH_2PO_4$, 0.03 g of $FeSO_4.7H_2O$, 0.03 g of $MnSO_4.5H_2O$, 0.45 mg of thiamine hydrochloride, 0.45 mg of biotin, 0.15 g of DL-methionine, 0.2 g (as total nitrogen) of soybean hydrolysate solution obtained with HCl, and 50 g of $CaCO_3$, filled up with water to 1 L, and adjusted to pH7.0) containing 6 mg/L of chloramphenicol and 25 mg/L of kanamycin at 30° C. for 72 hr. After completion of the culture, 5 μL of each culture supernatant obtained by centrifugation was subjected to reduced SDS-PAGE, and then staining was carried out with SYPRO Orange (Life Technologies), to compare the secretion amount of CspB50TEV-Teri (FIG. 9). In addition, the secretion amount of CspB50TEV-Teri observed for a part of the strains was shown in Table 7 with scores ranging from "+" to "+++". As a result, when introducing pVphoS(WT) into the YDK010ΔphoS strain, the secretion amount of CspB50TEV-Teri was equivalent to that observed for the YDK010 strain, and when introducing pVphoS(W302C) into the YDK010ΔphoS strain, the secretion amount of CspB50TEV-Teri was equivalent to that observed for the YDK010::phoS(W302C) strain. From this, it was revealed that deletion of the phoS gene on the chromosome can be functionally complemented by amplifying any wild-type or mutant phoS genes on a plasmid. Therefore, it was revealed that an effect equivalent to that obtained by mutating the phoS gene on the chromosome can be obtained by utilizing an expression plasmid of a mutant phoS gene.

TABLE 7

| Strain | Secretion amount |
|---|---|
| YDK010/pPKK50TEV-Teri | + |
| YDK010::phoS(W302C)/pPKK50TEV-Teri | +++ |
| YDK010ΔphoS/pVphoS(WT)/pPKK50TEV-Teri | + |
| YDK010ΔphoS/pVphoS(W302C)/pPKK50TEV-Teri | +++ |

Example 9: Secretory Expression of Heterologous Protein Using Strains Expressing Mutant PhoS(W302X) in which the Tryptophan Residue at Position 302 of Wild-type PhoS Protein was Replaced with an Arbitrary Amino Acid Residue (1) Construction of Expression Plasmids of Mutant phoS Genes Encoding Various Mutant PhoS(W302X) Proteins Plasmids pVphoS(W302X) for expression of mutant PhoS(W302X) in which the tryptophan residue at position 302 of the wild-type PhoS protein (W302) was replaced with another amino acid residue were constructed. The "X" represents an arbitrary amino acid residue.

To construct pVphoS(W302S), which is an expression plasmid of the mutant PhoS(W302S) protein, PCR was carried out by using the pVphoS(WT) plasmid constructed in Example 8(1) as the template, in combination with primers of SEQ ID NOS: 32 and 34 to amplify a region of about 0.9 kbp containing an N-terminal side of the phoS gene, and in combination with primers of SEQ ID NOS: 33 and 35 to amplify a region of about 0.6 kbp containing a C-terminal side of the phoS gene. The primers of SEQ ID NOS: 34 and 35 were designed so as to replace the codon (tgg) encoding the tryptophan residue at position 302 of the wild-type PhoS protein with a codon (tcc) encoding a serine residue. PCR was carried out with Pyrobest® DNA polymerase (Takara Bio), and the reaction conditions were according to the protocol recommended by the manufacturer. The amplified DNA fragments were subject to agarose gel electrophoresis, objective bands were cut out, and the DNA fragments were collected from the gel with Wizard® SV Gel and PCR Clean-Up System (Promega). The two DNA fragments were inserted at the SmaI site of the pVC7 vector disclosed in Japanese Patent Laid-open (Kokai) No. 9-070291 by infusion reaction, to obtain pVphoS(W302S), which is an amplification plasmid of the mutant phoS (W302S) gene. The infusion reaction was carried out with In-Fusion® HD Cloning Kit (Takara Bio), and the reaction conditions were according to the protocol recommended by the manufacturer. As a result of nucleotide sequencing of the inserted fragment, it was confirmed that the objective gene was constructed. Nucleotide sequencing was carried out with BigDye® Terminator v3.1 Cycle Sequencing Kit (Applied Biosystems) and 3130 Genetic Analyzer (Applied Biosystems).

In the same manner, the following plasmids were constructed: a plasmid pVphoS(W302A) for expression of the mutant PhoS(W302A) protein, a plasmid pVphoS(W302V) for expression of the mutant PhoS(W302V) protein, a plasmid pVphoS(W302M) for expression of the mutant PhoS(W302M) protein, a plasmid pVphoS(W302F) for expression of the mutant PhoS(W302F) protein, a plasmid pVphoS(W302Y) for expression of the mutant PhoS(W302Y) protein, a plasmid pVphoS(W302D) for expression of the mutant PhoS(W302D) protein, a plasmid pVphoS(W302N) for expression of the mutant PhoS(W302N) protein, a plasmid pVphoS(W302H) for expression of the mutant PhoS (W302H) protein, and a plasmid pVphoS(W302K) for expression of the mutant PhoS(W302K) protein. The primer sets for amplifying a region containing an N-terminal side of the phoS gene and the primer sets for amplifying a region containing a C-terminal side of the phoS gene used in PCR for constructing the respective plasmids are shown in Table 8.

TABLE 8

| Plasmid | N-terminal region | | C-terminal region | |
|---|---|---|---|---|
| pVphoS (W302S) | SEQ ID NO: 32 | SEQ ID NO: 34 | SEQ ID NO: 33 | SEQ ID NO: 35 |
| pVphoS (W302A) | SEQ ID NO: 32 | SEQ ID NO: 36 | SEQ ID NO: 33 | SEQ ID NO: 37 |
| pVphoS (W302V) | SEQ ID NO: 32 | SEQ ID NO: 38 | SEQ ID NO: 33 | SEQ ID NO: 39 |
| pVphoS (W302M) | SEQ ID NO: 32 | SEQ ID NO: 40 | SEQ ID NO: 33 | SEQ ID NO: 41 |
| pVphoS (W302F) | SEQ ID NO: 32 | SEQ ID NO: 42 | SEQ ID NO: 33 | SEQ ID NO: 43 |
| pVphoS (W302Y) | SEQ ID NO: 32 | SEQ ID NO: 44 | SEQ ID NO: 33 | SEQ ID NO: 45 |
| pVphoS (W302D) | SEQ ID NO: 32 | SEQ ID NO: 46 | SEQ ID NO: 33 | SEQ ID NO: 47 |
| pVphoS (W302N) | SEQ ID NO: 32 | SEQ ID NO: 48 | SEQ ID NO: 33 | SEQ ID NO: 49 |
| pVphoS (W302H) | SEQ ID NO: 32 | SEQ ID NO: 50 | SEQ ID NO: 33 | SEQ ID NO: 51 |
| pVphoS (W302K) | SEQ ID NO: 32 | SEQ ID NO: 52 | SEQ ID NO: 33 | SEQ ID NO: 53 |

Figure 10:
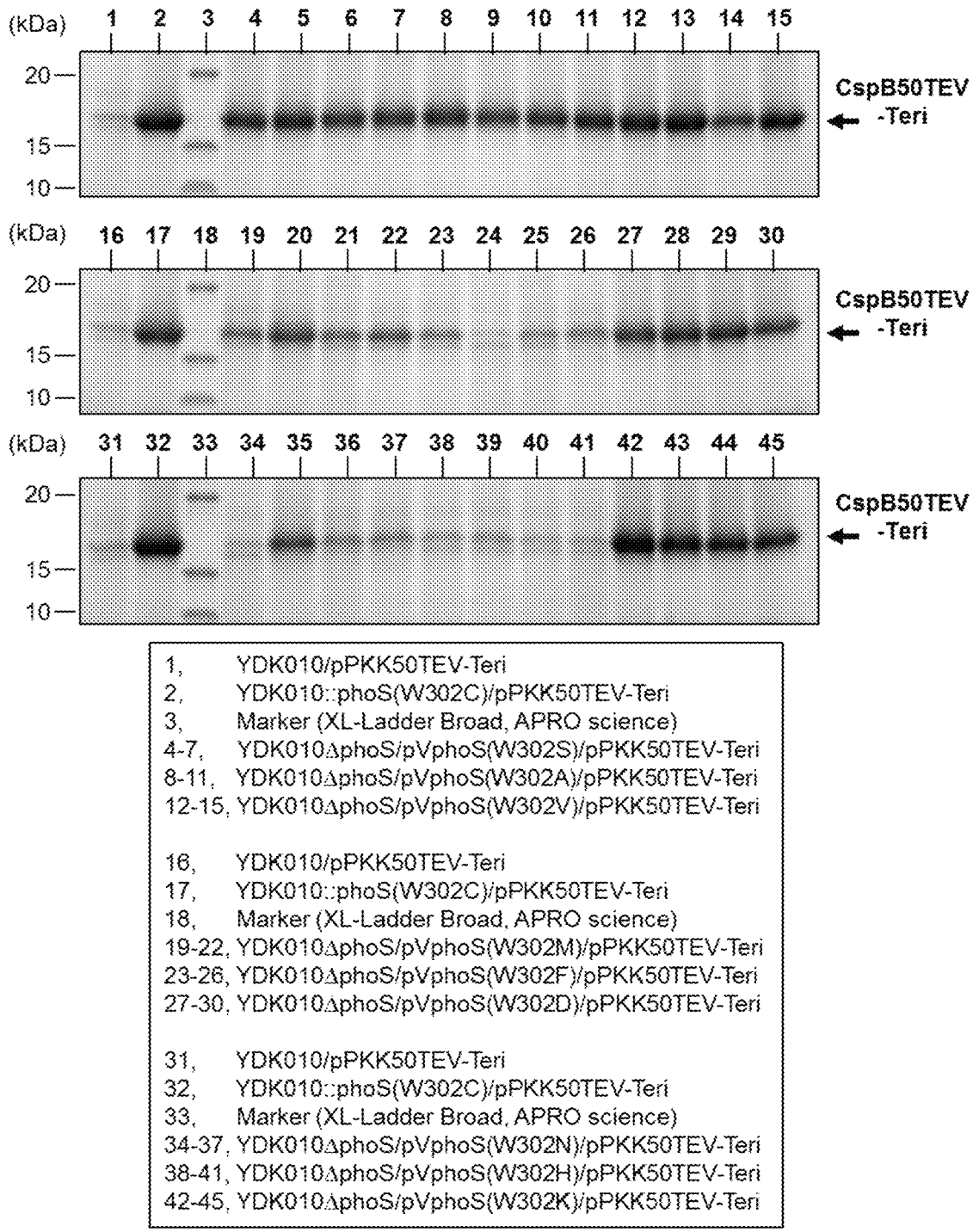
FIG. 10 is a photograph showing results of SDS-PAGE observed upon expressing CspB50TEV-Teri in PhoS-deletion strains of *C. glutamicum* YDK010 introduced with various mutant phoS(W302X) genes.

(2) Effect of Amplification of Various PhoS(W302X) Proteins on Secretory Expression of CspB50TEV-Teri Using PhoS-deletion Strain The YDK010ΔphoS strain constructed in Example 1(5) was transformed with pPKK50TEV-Teri disclosed in WO2014/126260 in combination with each of the various pVphoS(W302X) plasmids constructed in Example 9(1). The obtained transformants were each cultured on MMTG liquid medium (120 g of glucose, 3 g of MgSO$_4$.7H$_2$O, 30 g of (NH$_4$)$_2$SO$_4$, 1.5 g of KH$_2$PO$_4$, 0.03 g of FeSO$_4$.7H$_2$O, 0.03 g of MnSO$_4$.5H$_2$O, 0.45 mg of thiamine hydrochloride, 0.45 mg of biotin, 0.15 g of DL-methionine, 0.2 g (as total nitrogen) of soybean hydrolysate solution obtained with HCl, and 50 g of CaCO$_3$, filled up with water to 1 L, and adjusted to pH7.0) containing 6 mg/L of chloramphenicol and 25 mg/L of kanamycin at 30° C. for 72 hr. After completion of the culture, 5 µL of each culture supernatant obtained by centrifugation was subjected to reduced SDS-PAGE, and then staining was carried out with SYPRO Orange (Life Technologies), to compare the secretion amount of CspB50TEV-Teri (FIG. 10). In addition, the secretion amount of CspB50TEV-Teri observed for each of the strains was shown in Table 9 with scores ranging from "+" to "+++". As a result, it was revealed that the secretion amount of CspB50TEV-Teri is significantly improved when the tryptophan residue at position 302 of the wild-type PhoS protein is replaced with an amino acid residue other than an aromatic amino acid or histidine residue, such as a cysteine residue, as compared with the wild-type PhoS protein. Incidentally, regarding the pVphoS(W302Y)-introduced strain, no transformant was obtained, and hence, the secretion amount of CspB50TEV-Teri could not be evaluated.

From this, it was revealed that mutation of the tryptophan residue at position 302 of the wild-type PhoS protein leads to a significant improvement of the amount of a heterologous protein that is secreted, when the residue is mutated to be an arbitrary amino acid residue other than an aromatic amino acid or histidine residues, such as a cysteine residue.

TABLE 9

| Plasmid | Secretion amount of CspB50TEV-Teri |
|---|---|
| pVphoS(WT) | + |
| pVphoS(W302C) | +++ |
| pVphoS(W302S) | +++ |
| pVphoS(W302A) | +++ |
| pVphoS(W302V) | +++ |
| pVphoS(W302M) | ++ |
| pVphoS(W302F) | + |
| pVphoS(W302Y) | n.t. |
| pVphoS(W302D) | +++ |

TABLE 9-continued

| Plasmid | Secretion amount of CspB50TEV-Teri |
|---|---|
| pVphoS(W302N) | ++ |
| pVphoS(W302H) | + |
| pVphoS(W302K) | +++ | n.t; not tested

Example 10: Construction of PhoS(W302C)-mutant Strain from *Corynebacterium glutamicum* ATCC13869 Strain and Secretory Expression of Heterologous Protein (1) Construction of *C. glutamicum* ATCC13869::phoS (W302C) Strain The *C. glutamicum* ATCC13869 strain was transformed with pBS5T-phoS(W302C) constructed in Example 1(2), which is a vector for substitution of the mutant phoS gene. Strain selection from the obtained transformants was carried out according to the method disclosed in WO2006/057450, to obtain ATCC13869::phoS(W302C), which is a strain in which the wild-type phoS gene on the chromosome was replaced with the mutant phoS gene.

(2) Secretory Expression Exenatide Precursor (ExCP) Fused with N-terminal 6 Amino Acid Residues of CspB Mature Protein in *C. glutamicum* ATCC13869::phoS (W302C) Strain The *C. glutamicum* ATCC13869 strain and the ATCC13869::phoS(W302C) strain constructed in Example 10(1) were each transformed with pPK4_CspB6TEV-ExCP constructed in Example 4(1), which is a secretory expression plasmid of ExCP fused with the N-terminal 6 amino acid residues of mature CspB and the ProTEV protease recognition sequence, to obtain strains ATCC13869/pPK4_CspB6TEV-ExCP and ATCC13869::phoS(W302C)/pPK4_CspB6TEV-ExCP.

The obtained transformants were each cultured on MMTG liquid medium (120 g of glucose, 3 g of MgSO$_4$.7H$_2$O, 30 g of (NH$_4$)$_2$SO$_4$, 1.5 g of KH$_2$PO$_4$, 0.03 g of FeSO$_4$.7H$_2$O, 0.03 g of MnSO$_4$.5H$_2$O, 0.45 mg of thiamine hydrochloride, 0.45 mg of biotin, 0.15 g of DL-methionine, 0.2 g (as total nitrogen) of soybean hydrolysate solution obtained with HCl, and 50 g of CaCO$_3$, filled up with water to 1 L, and adjusted to pH7.0) containing 25 mg/L of kanamycin at 30° C. for 72 hr. After completion of the culture, 6.5 µL of each culture supernatant obtained by centrifugation was subjected to reduced SDS-PAGE, and then staining was carried out with Quick-CBB (Wako Pure Chemical Industries).

Figure 11:
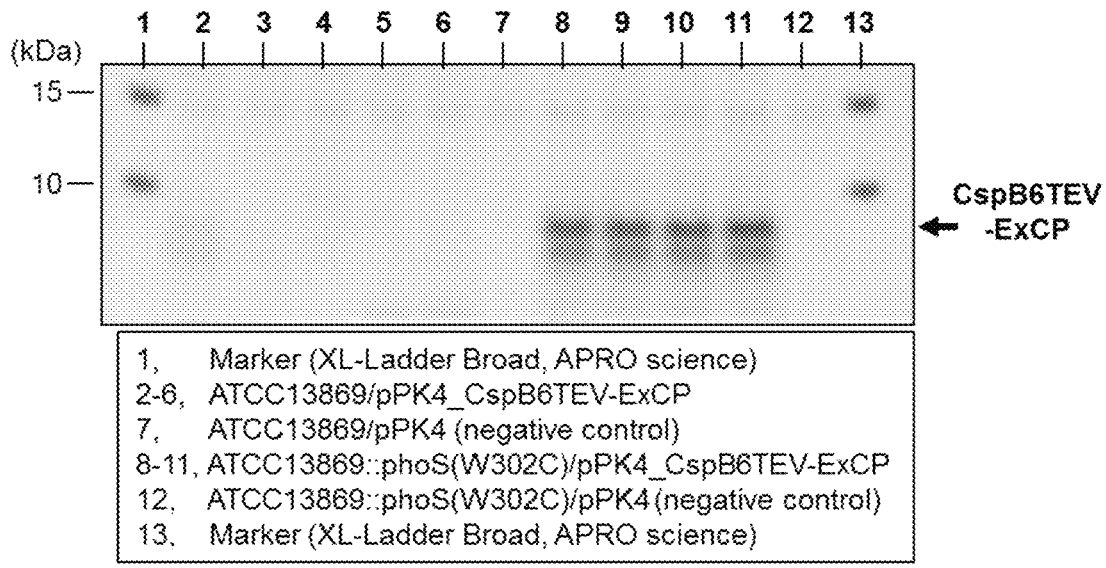
FIG. 11 is a photograph showing results of SDS-PAGE observed upon expressing CspB6TEV-ExCP in the *C. glutamicum* ATCC13869 strain and PhoS(W302C)-mutant strain thereof.

As a result, as with the case of using the YDK010 strain as the genetic background, a dense band indicating a protein having the molecular weight of CspB6TEV-ExCP was detected in the ATCC13869::phoS(W302C) strain while it was barely detectable in the ATCC13869 strain, and hence, it was confirmed that the secretion amount of CspB6TEV-ExCP was significantly improved in the ATCC13869::phoS (W302C) strain (FIG. 11). From this, it was revealed that the PhoS(W302C) mutation is an effective mutation that leads to a significant improvement in the amount of CspB6TEV-ExCP that is secreted when using the ATCC13869 strain as the genetic background.

Example 11: Construction of CspB-deletion Strain from *Corynebacterium Glutamicum* ATCC13869::phoS(W302C) Strain and Secretory Expression of Heterologous Protein (1) Construction of *C. glutamicum* ATCC13869::phoS (W302C)ΔcspB Strain The ATCC13869::phoS(W302C) strain was transformed with pBS5T-ΔcspB disclosed in WO2013/065869, which is a vector for deletion of the cspB gene. Strain selection from the obtained transformants was carried out according to the method disclosed in WO2006/057450, to obtain ATCC13869::phoS(W302C)ΔcspB, which is a strain deficient in the cspB gene.

(2) Secretory Expression Liver-type Fatty Acid-binding Protein (LFABP) Fused with N-terminal 6 Amino Acid Residues of CspB Mature Protein in *C. glutamicum* ATCC13869::phoS(W302C)ΔcspB Strain The *C. glutamicum* ATCC13869ΔcspB strain disclosed in WO2013/065869 and the ATCC13869::phoS(W302C) ΔcspB strain constructed in Example 11(1) were each transformed with pPK4_CspB6Xa-LFABP constructed in Example 3(1), which is a secretory expression plasmid of LFABP fused with the N-terminal 6 amino acid residues of mature CspB and the Factor Xa protease recognition sequence IEGR, to obtain strains ATCC13869ΔcspB/ pPK4_CspB6Xa-LFABP and ATCC13869::phoS(W302C) ΔcspB/pPK4_CspB6Xa-LFABP.

The obtained transformants were each cultured on MMTG liquid medium (120 g of glucose, 3 g of MgSO$_4$.7H$_2$O, 30 g of (NH$_4$)$_2$SO$_4$, 1.5 g of KH$_2$PO$_4$, 0.03 g of FeSO$_4$.7H$_2$O, 0.03 g of MnSO$_4$.5H$_2$O, 0.45 mg of thiamine hydrochloride, 0.45 mg of biotin, 0.15 g of DL-methionine, 0.2 g (as total nitrogen) of soybean hydrolysate solution obtained with HCl, and 50 g of CaCO$_3$, filled up with water to 1 L, and adjusted to pH7.0) containing 25 mg/L of kanamycin at 30° C. for 72 hr. After completion of the culture, 6.5 μL of each culture supernatant obtained by centrifugation was subjected to reduced SDS-PAGE, and then staining was carried out with Quick-CBB (Wako Pure Chemical Industries).

Figure 12:
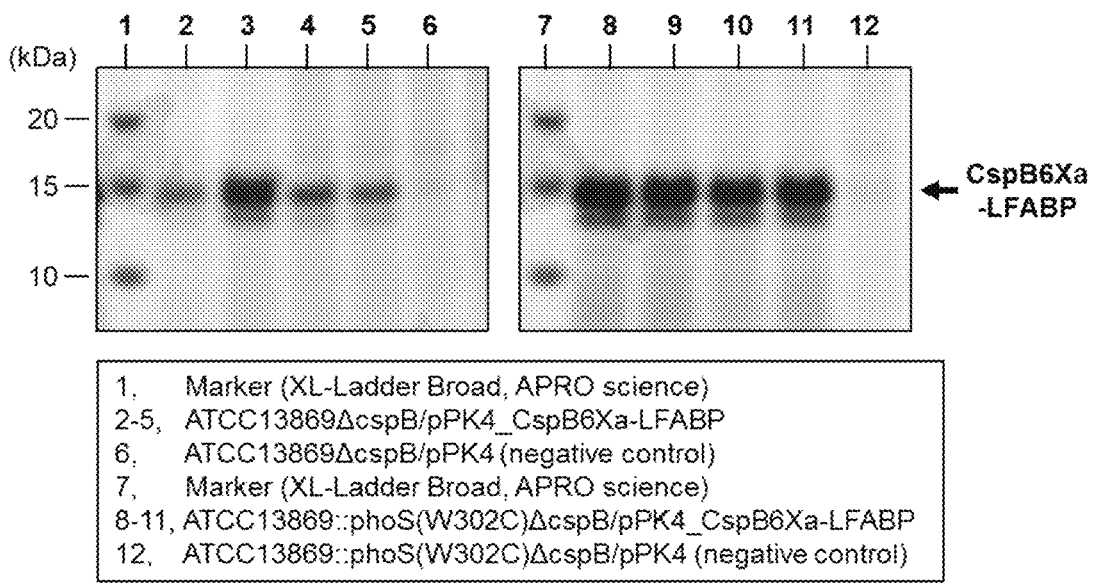
FIG. 12 is a photograph showing results of SDS-PAGE observed upon expressing CspB6Xa-LFABP in the *C. glutamicum* ATCC13869ΔcspB strain and PhoS(W302C)-mutant strain thereof.

As a result, as with the case of using the YDK010 strain as the genetic background, a dense band was detected indicating a protein having the molecular weight of CspB6Xa-LFABP in the ATCC13869::phoS(W302C)ΔcspB strain, as compared with the ATCC13869ΔcspB strain, and hence, it was confirmed that the amount of CspB6Xa-LFABP that was secreted was significantly improved in the ATCC13869::phoS(W302C)ΔcspB strain (FIG. 12). From this, it was revealed that the PhoS(W302C) mutation is an effective mutation that leads to a significant improvement in the amount of CspB6Xa-LFABP that is secreted when using the ATCC13869ΔcspB strain as the genetic background.

From Examples 10-11, it was revealed that the secretory expression amount of an objective protein can be significantly improved by using the PhoS(W302C)-mutant strain and also when using the ATCC13869 or ATCC13869ΔcspB strain as the genetic background.

Hence, From Examples 2-11, it was revealed that the secretion amount of an objective protein can be significantly improved by using the PhoS(W302C)-mutant strain regardless of the genetic background of the host strain.

INDUSTRIAL APPLICABILITY

According to the present invention, heterologous proteins can be efficiently produced by secretory production.

EXPLANATION OF SEQUENCE LISTING

SEQ ID NOS:
1: Nucleotide sequence of mutant phoS gene of *C. glutamicum* YDK0107
2: Amino acid sequence of mutant PhoS protein of *C. glutamicum* YDK0107
3: Nucleotide sequence of wild-type phoS gene of *C. glutamicum* YDK010
4: Amino acid sequence of wild-type PhoS protein of *C. glutamicum* YDK010
5 to 10: Primers
11: Amino acid sequence of LFABP
12: Nucleotide sequence encoding CspB6Xa-LFABP
13: Amino acid sequence of CspB6Xa-LFABP
14: Amino acid sequence of Exenatide precursor
15: Nucleotide sequence encoding CspB6TEV-ExCP
16: Amino acid sequence of CspB6TEV-ExCP
17 to 53: Primers
54: Amino acid sequence of PhoS protein of *C. glutamicum* ATCC 13032
55: Amino acid sequence of PhoS protein of *C. glutamicum* ATCC 14067
56: Amino acid sequence of PhoS protein of *C. callunae*
57: Amino acid sequence of PhoS protein of *C. crenatum*
58: Amino acid sequence of PhoS protein of *C. efficiens*
59: Amino acid sequence of HisAK domain of PhoS protein of *C. glutamicum* YDK0107
60: Amino acid sequence of HisAK domain of PhoS protein of *C. glutamicum* YDK010
61: Amino acid sequence of HisAK domain of PhoS protein of *C. glutamicum* ATCC 13869
62: Amino acid sequence of HisAK domain of PhoS protein of *C. glutamicum* ATCC 13032
63: Amino acid sequence of HisAK domain of PhoS protein of *C. glutamicum* ATCC 14067
64: Amino acid sequence of HisAK domain of PhoS protein of *C. callunae*
65: Amino acid sequence of HisAK domain of PhoS protein of *C. crenatum*
66: Amino acid sequence of HisAK domain of PhoS protein of *C. efficiens*
67: Nucleotide sequence of cspB gene of *C. glutamicum* ATCC 13869
68: Amino acid sequence of CspB protein of *C. glutamicum* ATCC 13869
69: Nucleotide sequence of tatA gene of *C. glutamicum* ATCC 13032
70: Amino acid sequence of TatA protein of *C. glutamicum* ATCC 13032
71: Nucleotide sequence of tatB gene of *C. glutamicum* ATCC 13032
72: Amino acid sequence of TatB protein of *C. glutamicum* ATCC 13032
73: Nucleotide sequence of tatC gene of *C. glutamicum* ATCC 13032

74: Amino acid sequence of TatC protein of *C. glutamicum* ATCC 13032
75: Amino acid sequence of TorA signal peptide
76: Amino acid sequence of SufI signal peptide
77: Amino acid sequence of PhoD signal peptide
78: Amino acid sequence of LipA signal peptide
79: Amino acid sequence of IMD signal peptide
80 and 81: Amino acid sequence of twin-arginine motif
82: Amino acid sequence of PS1 signal peptide
83: Amino acid sequence of PS2 signal peptide
84: Amino acid sequence of SlpA signal peptide
85: Amino acid sequence of CspB mature protein of *C. glutamicum* ATCC 13869
86 to 93: Amino acid sequences of insertion sequence used in the present invention in one embodiment
94: Recognition sequence of factor Xa protease
95: Recognition sequence of ProTEV protease
96: Nucleotide sequence of phoR gene of *C. glutamicum* ATCC 13032
97: Amino acid sequence of PhoR protein of *C. glutamicum* ATCC 13032

The invention claimed is:

1. A method for producing a heterologous protein comprising:
   culturing a coryneform bacterium comprising a genetic construct that allows for expression and secretion of a heterologous protein; and
   collecting the secreted heterologous protein,
   wherein the coryneform bacterium has been modified to comprise a polynucleotide encoding a mutant phosphate sensor kinase (PhoS) protein,
   wherein the mutant PhoS protein has PhoS sensor kinase activity and comprises an amino acid sequence having at least 90% sequence identity to the amino acid sequence of SEQ ID NO: 4, and wherein the tryptophan residue at the position corresponding to amino acid 302 of SEQ ID NO: 4 in the amino acid sequence of the mutant PhoS protein is replaced with an amino acid residue
   selected from the group consisting of lysine, alanine, valine, serine, cysteine, methionine, aspartic acid, and asparagine,
   wherein the genetic construct comprises, in the direction from 5' to 3', a promoter sequence that is able to function in the coryneform bacterium, a nucleic acid sequence encoding a signal peptide that is able to function in the coryneform bacterium, and a nucleic acid sequence encoding the heterologous protein, and
   wherein the heterologous protein is expressed as a fusion protein with the signal peptide.

2. The method according to claim 1, wherein the signal peptide is a Tat-dependent signal peptide.

3. The method according to claim 2, wherein the Tat-dependent signal peptide is selected from the group consisting of TorA, SufI, PhoD, LipA, and IMD.

4. The method according to claim 2, wherein the coryneform bacterium has been further modified so that the expression of one or more genes encoding a Tat secretion system is/are increased as compared to a coryneform bacterium that has not been modified to increase the expression of one or more genes encoding a Tat secretion system, wherein the modification is selected from the group consisting of increasing the copy number of the one or more genes encoding a Tat secretion system, replacing the promoter of the one or more genes encoding a Tat secretion system with a stronger promoter, and a combination thereof.

5. The method according to claim 4, wherein the one or more genes encoding a Tat secretion system are tatA, tatB, tatC, and tatE.

6. The method according to claim 1, wherein the signal peptide is a Sec-dependent signal peptide.

7. The method according to claim 6, wherein the Sec-dependent signal peptide is selected from the group consisting of PS1, PS2, and S1pA.

8. The method according to claim 1, wherein the genetic construct further comprises a nucleic acid sequence encoding an amino acid sequence comprising Gln-Glu-Thr between the nucleic acid sequence encoding the signal peptide that is able to function in the coryneform bacterium and the nucleic acid sequence encoding the heterologous protein.

9. The method according to claim 8, wherein the genetic construct further comprises a nucleic acid sequence encoding an amino acid sequence capable of being cleaved by a protease between the nucleic acid sequence encoding the amino acid sequence comprising Gln-Glu-Thr and the nucleic acid sequence encoding the heterologous protein.

10. The method according to claim 1, wherein the coryneform bacterium belongs to the genus *Corynebacterium*.

11. The method according to claim 10, wherein the coryneform bacterium is *Corynebacterium glutamicum*.

12. The method according to claim 11, wherein the coryneform bacterium is a modified *Corynebacterium glutamicum* AJ12036 strain or a modified *Corynebacterium glutamicum* ATCC13869 strain.

13. The method according to claim 1, wherein a gene encoding a cell surface layer protein has been inactivated in the coryneform bacterium.

* * * * *

SEQUENCE LISTING

```
<160> NUMBER OF SEQ ID NOS: 97

<210> SEQ ID NO 1
<211> LENGTH: 1458
<212> TYPE: DNA
<213> ORGANISM: Corynebacterium glutamicum

<400> SEQUENCE: 1
atggaaaacc cttatgtcgc tgcgctcgat gacgataaaa aagaagtcgg cgcaataaaa      60
gaagcagaaa aagaacctga aataggtccc atcagagctg ccggacgagc cataccgctg     120
cgcacccgca tcattttgat cgtggtgggt atcgccgggc ttggtttgct ggtcaacgcg     180
attgctgttt ccagcctcat gcgtgaagtt tcctataccc gcatggatca agagctagag     240
acctcgatgg ggacgtgggc gcataacgtt gagctgttta atttcgatgg cgtccgccaa     300
gggccaccca gcgattatta tgtggccaag gttttcctg atggatccag cattattttc      360
aacgatgcac aatcggcacc caatctagct gaaaccacca tcggtactgg tccacacact     420
gtggatgctg ctagcggttc tgcctccaac actccgtggc gtgtgatggc ggaaaagaac     480
ggtgacatta tcaccgtggt gggtaaaagc atgggcgtg aaacaaacct gctgtaccga      540
ttggtgatgg tgcagatgat catcggcgcg ctgattctgg ttgctatttt gattacttca     600
ctcttcctag tcagacgctc gttgcggccg ttgagagaag ttgaagagac cgccaccagg     660
attgcgggcg gtgatttgga tcgacgtgtc ccgcagtggc aatgaccac agaagtcgga      720 cagctgtcga atgccctcaa tatcatgttg gagcagctcc aagcctcaat tctgaccgcc     780
cagcaaaaag aagctcagat gcgccgattc gttggcgacg cctcccacga gctccgcaca     840
ccactgacct ctgtgaaggg cttcaccgag ctgtattcat caggtgcaac agatgatgcc     900
aactgtgtca tgtccaagat cggtggcgaa gcccaacgca tgagtgtgct tgtggaagac     960
ctcctgtcac tgacgcgtgc cgaaggccag caaatggaga agcaccgcgt tgacgtgctg    1020
gaactcgcat tggcagtacg cggatccatg cgagcagcct ggccagatcg caccgtcaac    1080
gtgtccaata aagccgagtc cattccagtt gttgaaggcg acccaacccg cctccaccaa    1140
gttctcacca acctggttgc caacggactc aaccacggcg gaccggacgc ggaagtcagc    1200
attgagatca acaccgatgg gcaaaacgtg aggattctcg tggcagacaa cggtgtcgga    1260
atgtctgaag aagatgccca gcatatcttc gagcgtttct accgcgccga ttcctcccgc    1320
tcacgcgcat ccggcggatc gggcctcggc cttgcgatca cgaaatccct ggtcgaaggc    1380
cacggcggca cagtcaccgt cgacagcgtg caaggcgaag gcacggtgtt cacgatcacc    1440
ttgccggcgg tttcttaa                                                  1458

<210> SEQ ID NO 2
<211> LENGTH: 485
<212> TYPE: PRT
<213> ORGANISM: Corynebacterium glutamicum
```

-continued

<400> SEQUENCE: 2

Met Glu Asn Pro Tyr Val Ala Ala Leu Asp Asp Lys Lys Glu Val
1               5                   10                  15

Gly Ala Ile Lys Glu Ala Glu Lys Glu Pro Glu Ile Gly Pro Ile Arg
                20                  25                  30

Ala Ala Gly Arg Ala Ile Pro Leu Arg Thr Arg Ile Ile Leu Ile Val
            35                  40                  45

Val Gly Ile Ala Gly Leu Leu Leu Val Asn Ala Ile Ala Val Ser
    50                  55                  60

Ser Leu Met Arg Glu Val Ser Tyr Thr Arg Met Asp Gln Glu Leu Glu
65                  70                  75                  80

Thr Ser Met Gly Thr Trp Ala His Asn Val Glu Leu Phe Asn Phe Asp
                85                  90                  95

Gly Val Arg Gln Gly Pro Pro Ser Asp Tyr Tyr Val Ala Lys Val Phe
                100                 105                 110

Pro Asp Gly Ser Ser Ile Ile Phe Asn Asp Ala Gln Ser Ala Pro Asn
            115                 120                 125

Leu Ala Glu Thr Thr Ile Gly Thr Gly Pro His Thr Val Asp Ala Ala
130                 135                 140

Ser Gly Ser Ala Ser Asn Thr Pro Trp Arg Val Met Ala Glu Lys Asn
145                 150                 155                 160

Gly Asp Ile Ile Thr Val Val Gly Lys Ser Met Gly Arg Glu Thr Asn
                165                 170                 175

Leu Leu Tyr Arg Leu Val Met Val Gln Met Ile Ile Gly Ala Leu Ile
            180                 185                 190

Leu Val Ala Ile Leu Ile Thr Ser Leu Phe Leu Val Arg Arg Ser Leu
        195                 200                 205

Arg Pro Leu Arg Glu Val Glu Glu Thr Ala Thr Arg Ile Ala Gly Gly
210                 215                 220

Asp Leu Asp Arg Arg Val Pro Gln Trp Pro Met Thr Thr Glu Val Gly
225                 230                 235                 240

Gln Leu Ser Asn Ala Leu Asn Ile Met Leu Glu Gln Leu Gln Ala Ser
                245                 250                 255

Ile Leu Thr Ala Gln Gln Lys Glu Ala Gln Met Arg Arg Phe Val Gly
            260                 265                 270

Asp Ala Ser His Glu Leu Arg Thr Pro Leu Thr Ser Val Lys Gly Phe
        275                 280                 285

Thr Glu Leu Tyr Ser Ser Gly Ala Thr Asp Asp Ala Asn Cys Val Met
    290                 295                 300

Ser Lys Ile Gly Gly Glu Ala Gln Arg Met Ser Val Leu Val Glu Asp
305                 310                 315                 320

Leu Leu Ser Leu Thr Arg Ala Glu Gly Gln Gln Met Glu Lys His Arg
                325                 330                 335

Val Asp Val Leu Glu Leu Ala Leu Ala Val Arg Gly Ser Met Arg Ala
            340                 345                 350

Ala Trp Pro Asp Arg Thr Val Asn Val Ser Asn Lys Ala Glu Ser Ile
        355                 360                 365

Pro Val Val Glu Gly Asp Pro Thr Arg Leu His Gln Val Leu Thr Asn
    370                 375                 380

Leu Val Ala Asn Gly Leu Asn His Gly Gly Pro Asp Ala Glu Val Ser
385                 390                 395                 400

Ile Glu Ile Asn Thr Asp Gly Gln Asn Val Arg Ile Leu Val Ala Asp

```
                    405                 410                 415
Asn Gly Val Gly Met Ser Glu Glu Asp Ala Gln His Ile Phe Glu Arg
            420                 425                 430

Phe Tyr Arg Ala Asp Ser Ser Arg Ser Arg Ala Ser Gly Gly Ser Gly
        435                 440                 445

Leu Gly Leu Ala Ile Thr Lys Ser Leu Val Glu Gly His Gly Gly Thr
    450                 455                 460

Val Thr Val Asp Ser Val Gln Gly Glu Gly Thr Val Phe Thr Ile Thr
465                 470                 475                 480

Leu Pro Ala Val Ser
            485

<210> SEQ ID NO 3
<211> LENGTH: 1458
<212> TYPE: DNA
<213> ORGANISM: Corynebacterium glutamicum

<400> SEQUENCE: 3
atggaaaacc cttatgtcgc tgcgctcgat gacgataaaa agaagtcgg cgcaataaaa      60 gaagcagaaa agaacctga  ataggtcccc atcagagctg ccggacgagc cataccgctg    120
cgcacccgca tcattttgat cgtggtgggt atcgccgggc ttggtttgct ggtcaacgcg    180
attgctgttt ccagcctcat gcgtgaagtt tcctataccc gcatggatca agagctagag    240
acctcgatgg ggacgtgggc gcataacgtt gagctgttta atttcgatgg cgtccgccaa    300
gggccaccca gcgattatta tgtggccaag gttttcctg atggatccag cattattttc     360
aacgatgcac aatcggcacc caatctagct gaaaccacca tcggtactgg tccacacact    420
gtggatgctg ctagcggttc tgcctccaac actccgtggc gtgtgatggc ggaaaagaac    480
ggtgacatta tcaccgtggt gggtaaaagc atggggcgtg aaacaaacct gctgtaccga    540
ttggtgatgg tgcagatgat catcggcgcg ctgattctgg ttgctatttt gattacttca    600
ctcttcctag tcagacgctc gttgcggccg ttgagagaag ttgaagagac cgccaccagg    660
attgcgggcg tgatttggat cgacgtgtc ccgcagtggc caatgaccac agaagtcgga    720
cagctgtcga atgccctcaa tatcatgttg gagcagctcc aagcctcaat tctgaccgcc    780
cagcaaaaag aagctcagat gcgccgattc gttggcgacg cctcccacga gctccgcaca    840
ccactgacct ctgtgaaggg cttcaccgag ctgtattcat caggtgcaac agatgatgcc    900
aactgggtca tgtccaagat cggtggcgaa gcccaacgca tgagtgtgct tgtggaagac    960
ctcctgtcac tgacgcgtgc cgaaggccag caaatggaga agcaccgcgt tgacgtgctg   1020
gaactcgcat tggcagtacg cggatccatg cgagcagcct ggccagatcg caccgtcaac   1080
gtgtccaata agccgagtc cattccagtt gttgaaggcg acccaacccg cctccaccaa   1140
gttctcacca acctggttgc caacggactc aaccacggcg gaccggacgc ggaagtcagc   1200
attgagatca caccgatgg gcaaaacgtg aggattctcg tggcagacaa cggtgtcgga   1260
atgtctgaag aagatgccca gcatatcttc gagcgtttct accgcgccga ttcctcccgc   1320
tcacgcgcat ccggcggatc gggcctcggc cttgcgatca cgaaatccct ggtcgaaggc   1380
cacggcggca cagtcaccgt cgacagcgtg caaggcgaag gcacggtgtt cacgatcacc   1440
ttgccggcgg tttcttaa                                                 1458

<210> SEQ ID NO 4
<211> LENGTH: 485
<212> TYPE: PRT
```

<213> ORGANISM: Corynebacterium glutamicum

<400> SEQUENCE: 4

```
Met Glu Asn Pro Tyr Val Ala Ala Leu Asp Asp Lys Lys Glu Val
1               5                   10                  15

Gly Ala Ile Lys Glu Ala Glu Lys Glu Pro Glu Ile Gly Pro Ile Arg
            20                  25                  30

Ala Ala Gly Arg Ala Ile Pro Leu Arg Thr Arg Ile Ile Leu Ile Val
            35                  40                  45

Val Gly Ile Ala Gly Leu Gly Leu Leu Val Asn Ala Ile Ala Val Ser
    50                  55                  60

Ser Leu Met Arg Glu Val Ser Tyr Thr Arg Met Asp Gln Glu Leu Glu
65                  70                  75                  80

Thr Ser Met Gly Thr Trp Ala His Asn Val Glu Leu Phe Asn Phe Asp
                85                  90                  95

Gly Val Arg Gln Gly Pro Pro Ser Asp Tyr Tyr Val Ala Lys Val Phe
            100                 105                 110

Pro Asp Gly Ser Ser Ile Ile Phe Asn Asp Ala Gln Ser Ala Pro Asn
            115                 120                 125

Leu Ala Glu Thr Thr Ile Gly Thr Gly Pro His Thr Val Asp Ala Ala
    130                 135                 140

Ser Gly Ser Ala Ser Asn Thr Pro Trp Arg Val Met Ala Glu Lys Asn
145                 150                 155                 160

Gly Asp Ile Ile Thr Val Val Gly Lys Ser Met Gly Arg Glu Thr Asn
                165                 170                 175

Leu Leu Tyr Arg Leu Val Met Val Gln Met Ile Ile Gly Ala Leu Ile
            180                 185                 190

Leu Val Ala Ile Leu Ile Thr Ser Leu Phe Leu Val Arg Arg Ser Leu
    195                 200                 205

Arg Pro Leu Arg Glu Val Glu Glu Thr Ala Thr Arg Ile Ala Gly Gly
    210                 215                 220

Asp Leu Asp Arg Arg Val Pro Gln Trp Pro Met Thr Thr Glu Val Gly
225                 230                 235                 240

Gln Leu Ser Asn Ala Leu Asn Ile Met Leu Glu Gln Leu Gln Ala Ser
                245                 250                 255

Ile Leu Thr Ala Gln Gln Lys Gly Ala Gln Met Arg Arg Phe Val Gly
            260                 265                 270

Asp Ala Ser His Glu Leu Arg Thr Pro Leu Thr Ser Val Lys Gly Phe
            275                 280                 285

Thr Glu Leu Tyr Ser Ser Gly Ala Thr Asp Asp Ala Asn Trp Val Met
    290                 295                 300

Ser Lys Ile Gly Gly Glu Ala Gln Arg Met Ser Val Leu Val Glu Asp
305                 310                 315                 320

Leu Leu Ser Leu Thr Arg Ala Glu Gly Gln Gln Met Glu Lys His Arg
                325                 330                 335

Val Asp Val Leu Glu Leu Ala Leu Ala Val Arg Gly Ser Met Arg Ala
            340                 345                 350

Ala Trp Pro Asp Arg Thr Val Asn Val Ser Asn Lys Ala Glu Ser Ile
            355                 360                 365

Pro Val Val Glu Gly Asp Pro Thr Arg Leu His Gln Val Leu Thr Asn
    370                 375                 380

Leu Val Ala Asn Gly Leu Asn His Gly Gly Pro Asp Ala Glu Val Ser
385                 390                 395                 400
```

-continued

```
Ile Glu Ile Asn Thr Asp Gly Gln Asn Val Arg Ile Leu Val Ala Asp
            405                 410                 415
Asn Gly Val Gly Met Ser Glu Glu Asp Ala Gln His Ile Phe Glu Arg
        420                 425                 430
Phe Tyr Arg Ala Asp Ser Ser Arg Ser Arg Ala Ser Gly Gly Ser Gly
    435                 440                 445
Leu Gly Leu Ala Ile Thr Lys Ser Leu Val Glu Gly His Gly Gly Thr
450                 455                 460
Val Thr Val Asp Ser Val Gln Gly Glu Gly Thr Val Phe Thr Ile Thr
465                 470                 475                 480
Leu Pro Ala Val Ser
            485

<210> SEQ ID NO 5
<211> LENGTH: 25
<212> TYPE: DNA
<213> ORGANISM: Artificial Sequence
<220> FEATURE:
<223> OTHER INFORMATION: primer

<400> SEQUENCE: 5
aggcagcaaa acaccgagga ctcaa                                           25

<210> SEQ ID NO 6
<211> LENGTH: 25
<212> TYPE: DNA
<213> ORGANISM: Artificial Sequence
<220> FEATURE:
<223> OTHER INFORMATION: primer

<400> SEQUENCE: 6
cgggcttggt ttgctggtca acgcg                                           25

<210> SEQ ID NO 7
<211> LENGTH: 33
<212> TYPE: DNA
<213> ORGANISM: Artificial Sequence
<220> FEATURE:
<223> OTHER INFORMATION: primer

<400> SEQUENCE: 7
tcgagctcgg tacccggcta atcctctggc ctg                                  33

<210> SEQ ID NO 8
<211> LENGTH: 33
<212> TYPE: DNA
<213> ORGANISM: Artificial Sequence
<220> FEATURE:
<223> OTHER INFORMATION: primer

<400> SEQUENCE: 8
taactaattt ctcctaggca tcaagggccg gaa                                  33

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
aggagaaatt agttacgtgg                                                 20
```

<210> SEQ ID NO 10
<211> LENGTH: 33
<212> TYPE: DNA
<213> ORGANISM: Artificial Sequence
<220> FEATURE:
<223> OTHER INFORMATION: primer

<400> SEQUENCE: 10

```
ctctagagga tcccccggat gtacgtggaa gac                                     33
```

<210> SEQ ID NO 11
<211> LENGTH: 127
<212> TYPE: PRT
<213> ORGANISM: Homo sapiens

<400> SEQUENCE: 11

```
Met Ser Phe Ser Gly Lys Tyr Gln Leu Gln Ser Gln Glu Asn Phe Glu
1               5                   10                  15

Ala Phe Met Lys Ala Ile Gly Leu Pro Glu Glu Leu Ile Gln Lys Gly
            20                  25                  30

Lys Asp Ile Lys Gly Val Ser Glu Ile Val Gln Asn Gly Lys His Phe
        35                  40                  45

Lys Phe Thr Ile Thr Ala Gly Ser Lys Val Ile Gln Asn Glu Phe Thr
    50                  55                  60

Val Gly Glu Glu Cys Glu Leu Glu Thr Met Thr Gly Glu Lys Val Lys
65                  70                  75                  80

Thr Val Val Gln Leu Glu Gly Asp Asn Lys Leu Val Thr Thr Phe Lys
                85                  90                  95

Asn Ile Lys Ser Val Thr Glu Leu Asn Gly Asp Ile Ile Thr Asn Thr
            100                 105                 110

Met Thr Leu Gly Asp Ile Val Phe Lys Arg Ile Ser Lys Arg Ile
        115                 120                 125
```

<210> SEQ ID NO 12
<211> LENGTH: 504
<212> TYPE: DNA
<213> ORGANISM: Homo sapiens

<400> SEQUENCE: 12

```
atgtttaaca accgtatccg cactgcagct ctcgctggtg caatcgcaat ctccaccgca       60
gcttccggcg tagctatccc agcattcgct caggagacca cccaaccat cgagggccgc      120
atgtccttct ccggcaagta ccagctgcag tcccaggaaa acttcgaggc attcatgaag     180
gctatcggtc tgccagaaga gctcatccag aagggcaagg atatcaaggg tgtttccgaa    240
atcgtgcaga acggcaagca cttcaagttc accatcaccg caggttccaa ggtcatccag    300
aacgagttca ccgttggcga agagtgcgaa ctcgagacca tgaccggtga aaaggttaag    360
accgtggtcc agctggaggg cgacaacaag ctcgtgacca ccttcaagaa catcaagtcc    420
gtcaccgaac tgaacggcga tatcatcacc aacaccatga ccctcggtga catcgtgttc    480
aagcgcatct ccaagcgtat ctaa                                            504
```

<210> SEQ ID NO 13
<211> LENGTH: 167
<212> TYPE: PRT
<213> ORGANISM: Homo sapiens

<400> SEQUENCE: 13

```
Met Phe Asn Asn Arg Ile Arg Thr Ala Ala Leu Ala Gly Ala Ile Ala
1               5                   10                  15
```

Ile Ser Thr Ala Ala Ser Gly Val Ala Ile Pro Ala Phe Ala Gln Glu
            20                  25                  30

Thr Asn Pro Thr Ile Glu Gly Arg Met Ser Phe Ser Gly Lys Tyr Gln
        35                  40                  45

Leu Gln Ser Gln Glu Asn Phe Glu Ala Phe Met Lys Ala Ile Gly Leu
    50                  55                  60

Pro Glu Glu Leu Ile Gln Lys Gly Lys Asp Ile Lys Gly Val Ser Glu
65                  70                  75                  80

Ile Val Gln Asn Gly Lys His Phe Lys Phe Thr Ile Thr Ala Gly Ser
                85                  90                  95

Lys Val Ile Gln Asn Glu Phe Thr Val Gly Glu Glu Cys Glu Leu Glu
            100                 105                 110

Thr Met Thr Gly Glu Lys Val Lys Thr Val Gln Leu Glu Gly Asp
        115                 120                 125

Asn Lys Leu Val Thr Thr Phe Lys Asn Ile Lys Ser Val Thr Glu Leu
    130                 135                 140

Asn Gly Asp Ile Ile Thr Asn Thr Met Thr Leu Gly Asp Ile Val Phe
145                 150                 155                 160

Lys Arg Ile Ser Lys Arg Ile
                165

<210> SEQ ID NO 14
<211> LENGTH: 41
<212> TYPE: PRT
<213> ORGANISM: Heloderma suspectum

<400> SEQUENCE: 14

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Cys Pro
        35                  40

<210> SEQ ID NO 15
<211> LENGTH: 252
<212> TYPE: DNA
<213> ORGANISM: Heloderma suspectum

<400> SEQUENCE: 15
atgtttaaca accgtatccg cactgcagct ctcgctggtg caatcgcaat ctccaccgca      60
gcttccggcg tagctatccc agcattcgct caggagacca acccaaccga aaacctgtac     120
ttccagcacg gcgagggaac cttcacgtct gatctgtcta agcagatgga ggaagaggca     180
gttcgcctgt tcattgagtg gctgaaaaat ggcggtcctt ctagcggtgc acctccccccc    240 tcctgcccat ga                                                         252

<210> SEQ ID NO 16
<211> LENGTH: 83
<212> TYPE: PRT
<213> ORGANISM: Heloderma suspectum

<400> SEQUENCE: 16

Met Phe Asn Asn Arg Ile Arg Thr Ala Ala Leu Ala Gly Ala Ile Ala
1               5                   10                  15

Ile Ser Thr Ala Ala Ser Gly Val Ala Ile Pro Ala Phe Ala Gln Glu
            20                  25                  30

```
Thr Asn Pro Thr Glu Asn Leu Tyr Phe Gln His Gly Glu Gly Thr Phe
         35                  40                  45

Thr Ser Asp Leu Ser Lys Gln Met Glu Glu Glu Ala Val Arg Leu Phe
     50                  55                  60

Ile Glu Trp Leu Lys Asn Gly Gly Pro Ser Ser Gly Ala Pro Pro Pro
65                  70                  75                  80

Ser Cys Pro

<210> SEQ ID NO 17
<211> LENGTH: 27
<212> TYPE: DNA
<213> ORGANISM: Artificial Sequence
<220> FEATURE:
<223> OTHER INFORMATION: primer

<400> SEQUENCE: 17
cgagccacca ggcaggcggg aaaatcg                                        27

<210> SEQ ID NO 18
<211> LENGTH: 27
<212> TYPE: DNA
<213> ORGANISM: Artificial Sequence
<220> FEATURE:
<223> OTHER INFORMATION: primer

<400> SEQUENCE: 18 cgatttccc gcctgcctgg tggctcg                                         27

<210> SEQ ID NO 19
<211> LENGTH: 23
<212> TYPE: DNA
<213> ORGANISM: Artificial Sequence
<220> FEATURE:
<223> OTHER INFORMATION: primer

<400> SEQUENCE: 19
cccgcttgat cattccttta agg                                            23

<210> SEQ ID NO 20
<211> LENGTH: 36
<212> TYPE: DNA
<213> ORGANISM: Artificial Sequence
<220> FEATURE:
<223> OTHER INFORMATION: primer

<400> SEQUENCE: 20
aatgggccct ttggtacccc taaataatat cggtcc                              36

<210> SEQ ID NO 21
<211> LENGTH: 27
<212> TYPE: DNA
<213> ORGANISM: Artificial Sequence
<220> FEATURE:
<223> OTHER INFORMATION: primer

<400> SEQUENCE: 21
cgtgctctag gggaaccgtg cgttccc                                        27

<210> SEQ ID NO 22
<211> LENGTH: 27
<212> TYPE: DNA
<213> ORGANISM: Artificial Sequence
<220> FEATURE:
<223> OTHER INFORMATION: primer
```

```
<400> SEQUENCE: 22
gggaacgcac ggttccccta gagcacg                                              27

<210> SEQ ID NO 23
<211> LENGTH: 27
<212> TYPE: DNA
<213> ORGANISM: Artificial Sequence
<220> FEATURE:
<223> OTHER INFORMATION: primer

<400> SEQUENCE: 23
cgacgctgaa gttgtagaga tcatccg                                              27

<210> SEQ ID NO 24
<211> LENGTH: 27
<212> TYPE: DNA
<213> ORGANISM: Artificial Sequence
<220> FEATURE:
<223> OTHER INFORMATION: primer

<400> SEQUENCE: 24
cggatgatct ctacaacttc agcgtcg                                              27

<210> SEQ ID NO 25
<211> LENGTH: 28
<212> TYPE: DNA
<213> ORGANISM: Artificial Sequence
<220> FEATURE:
<223> OTHER INFORMATION: primer

<400> SEQUENCE: 25
ggcggtaccc aaattcctgt gaagtagc                                             28

<210> SEQ ID NO 26
<211> LENGTH: 44
<212> TYPE: DNA
<213> ORGANISM: Artificial Sequence
<220> FEATURE:
<223> OTHER INFORMATION: primer

<400> SEQUENCE: 26
ggcgggcccg ccggcagtcg cacgtcgcgg cgttaacaat gacg                           44

<210> SEQ ID NO 27
<211> LENGTH: 24
<212> TYPE: DNA
<213> ORGANISM: Artificial Sequence
<220> FEATURE:
<223> OTHER INFORMATION: primer

<400> SEQUENCE: 27
gacaatggcg cggggaaga gacg                                                  24

<210> SEQ ID NO 28
<211> LENGTH: 22
<212> TYPE: DNA
<213> ORGANISM: Artificial Sequence
<220> FEATURE:
<223> OTHER INFORMATION: primer

<400> SEQUENCE: 28
caggtcgact ctagaggatc cc                                                   22

<210> SEQ ID NO 29
```

```
<211> LENGTH: 30
<212> TYPE: DNA
<213> ORGANISM: Artificial Sequence
<220> FEATURE:
<223> OTHER INFORMATION: primer

<400> SEQUENCE: 29
atattattta ggtctagaca aattcctgtg                                        30

<210> SEQ ID NO 30
<211> LENGTH: 35
<212> TYPE: DNA
<213> ORGANISM: Artificial Sequence
<220> FEATURE:
<223> OTHER INFORMATION: primer

<400> SEQUENCE: 30
ctgcaggtcg actctagaat taattaaaat ccaca                                  35

<210> SEQ ID NO 31
<211> LENGTH: 38
<212> TYPE: DNA
<213> ORGANISM: Artificial Sequence
<220> FEATURE:
<223> OTHER INFORMATION: primer

<400> SEQUENCE: 31
ctgcaggtcg actctagatc acatgtccaa ctctatcc                               38

<210> SEQ ID NO 32
<211> LENGTH: 35
<212> TYPE: DNA
<213> ORGANISM: Artificial Sequence
<220> FEATURE:
<223> OTHER INFORMATION: primer

<400> SEQUENCE: 32
ctctagagga tccccatgga aaacccttat gtcgc                                  35

<210> SEQ ID NO 33
<211> LENGTH: 34
<212> TYPE: DNA
<213> ORGANISM: Artificial Sequence
<220> FEATURE:
<223> OTHER INFORMATION: primer

<400> SEQUENCE: 33
tcgagctcgg taccettaag aaaccgccgg caag                                   34

<210> SEQ ID NO 34
<211> LENGTH: 30
<212> TYPE: DNA
<213> ORGANISM: Artificial Sequence
<220> FEATURE:
<223> OTHER INFORMATION: primer

<400> SEQUENCE: 34
catgacggag ttggcatcat ctgttgcacc                                        30

<210> SEQ ID NO 35
<211> LENGTH: 29
<212> TYPE: DNA
<213> ORGANISM: Artificial Sequence
<220> FEATURE:
<223> OTHER INFORMATION: primer

<400> SEQUENCE: 35
```

```
gccaactccg tcatgtccaa gatcggtgg                                        29

<210> SEQ ID NO 36
<211> LENGTH: 30
<212> TYPE: DNA
<213> ORGANISM: Artificial Sequence
<220> FEATURE:
<223> OTHER INFORMATION: primer

<400> SEQUENCE: 36
catgactgcg ttggcatcat ctgttgcacc                                       30

<210> SEQ ID NO 37
<211> LENGTH: 29
<212> TYPE: DNA
<213> ORGANISM: Artificial Sequence
<220> FEATURE:
<223> OTHER INFORMATION: primer

<400> SEQUENCE: 37
gccaacgcag tcatgtccaa gatcggtgg                                        29

<210> SEQ ID NO 38
<211> LENGTH: 30
<212> TYPE: DNA
<213> ORGANISM: Artificial Sequence
<220> FEATURE:
<223> OTHER INFORMATION: primer

<400> SEQUENCE: 38
catgaccacg ttggcatcat ctgttgcacc                                       30

<210> SEQ ID NO 39
<211> LENGTH: 29
<212> TYPE: DNA
<213> ORGANISM: Artificial Sequence
<220> FEATURE:
<223> OTHER INFORMATION: primer

<400> SEQUENCE: 39
gccaacgtgg tcatgtccaa gatcggtgg                                        29

<210> SEQ ID NO 40
<211> LENGTH: 30
<212> TYPE: DNA
<213> ORGANISM: Artificial Sequence
<220> FEATURE:
<223> OTHER INFORMATION: primer

<400> SEQUENCE: 40
catgaccatg ttggcatcat ctgttgcacc                                       30

<210> SEQ ID NO 41
<211> LENGTH: 29
<212> TYPE: DNA
<213> ORGANISM: Artificial Sequence
<220> FEATURE:
<223> OTHER INFORMATION: primer

<400> SEQUENCE: 41
gccaacatgg tcatgtccaa gatcggtgg                                        29

<210> SEQ ID NO 42
<211> LENGTH: 30
<212> TYPE: DNA
```

```
<213> ORGANISM: Artificial Sequence
<220> FEATURE:
<223> OTHER INFORMATION: primer

<400> SEQUENCE: 42
catgacgaag ttggcatcat ctgttgcacc                                      30

<210> SEQ ID NO 43
<211> LENGTH: 29
<212> TYPE: DNA
<213> ORGANISM: Artificial Sequence
<220> FEATURE:
<223> OTHER INFORMATION: primer

<400> SEQUENCE: 43
gccaacttcg tcatgtccaa gatcggtgg                                       29

<210> SEQ ID NO 44
<211> LENGTH: 30
<212> TYPE: DNA
<213> ORGANISM: Artificial Sequence
<220> FEATURE:
<223> OTHER INFORMATION: primer

<400> SEQUENCE: 44
catgacgtag ttggcatcat ctgttgcacc                                      30

<210> SEQ ID NO 45
<211> LENGTH: 29
<212> TYPE: DNA
<213> ORGANISM: Artificial Sequence
<220> FEATURE:
<223> OTHER INFORMATION: primer

<400> SEQUENCE: 45
gccaactacg tcatgtccaa gatcggtgg                                       29

<210> SEQ ID NO 46
<211> LENGTH: 30
<212> TYPE: DNA
<213> ORGANISM: Artificial Sequence
<220> FEATURE:
<223> OTHER INFORMATION: primer

<400> SEQUENCE: 46
catgacatcg ttggcatcat ctgttgcacc                                      30

<210> SEQ ID NO 47
<211> LENGTH: 29
<212> TYPE: DNA
<213> ORGANISM: Artificial Sequence
<220> FEATURE:
<223> OTHER INFORMATION: primer

<400> SEQUENCE: 47
gccaacgatg tcatgtccaa gatcggtgg                                       29

<210> SEQ ID NO 48
<211> LENGTH: 30
<212> TYPE: DNA
<213> ORGANISM: Artificial Sequence
<220> FEATURE:
<223> OTHER INFORMATION: primer

<400> SEQUENCE: 48
catgacgttg ttggcatcat ctgttgcacc                                      30
```

<210> SEQ ID NO 49
<211> LENGTH: 29
<212> TYPE: DNA
<213> ORGANISM: Artificial Sequence
<220> FEATURE:
<223> OTHER INFORMATION: primer

<400> SEQUENCE: 49
gccaacaacg tcatgtccaa gatcggtgg                                    29

<210> SEQ ID NO 50
<211> LENGTH: 30
<212> TYPE: DNA
<213> ORGANISM: Artificial Sequence
<220> FEATURE:
<223> OTHER INFORMATION: primer

<400> SEQUENCE: 50
catgacgtgg ttggcatcat ctgttgcacc                                   30

<210> SEQ ID NO 51
<211> LENGTH: 29
<212> TYPE: DNA
<213> ORGANISM: Artificial Sequence
<220> FEATURE:
<223> OTHER INFORMATION: primer

<400> SEQUENCE: 51
gccaaccacg tcatgtccaa gatcggtgg                                    29

<210> SEQ ID NO 52
<211> LENGTH: 30
<212> TYPE: DNA
<213> ORGANISM: Artificial Sequence
<220> FEATURE:
<223> OTHER INFORMATION: primer

<400> SEQUENCE: 52
catgaccttg ttggcatcat ctgttgcacc                                   30

<210> SEQ ID NO 53
<211> LENGTH: 29
<212> TYPE: DNA
<213> ORGANISM: Artificial Sequence
<220> FEATURE:
<223> OTHER INFORMATION: primer

<400> SEQUENCE: 53
gccaacaagg tcatgtccaa gatcggtgg                                    29

<210> SEQ ID NO 54
<211> LENGTH: 485
<212> TYPE: PRT
<213> ORGANISM: Corynebacterium glutamicum

<400> SEQUENCE: 54

Met Glu Asn Pro Tyr Val Ala Ala Leu Asp Asp Glu Asn Gln Glu Val
1               5                   10                  15

Gly Val Lys Lys Glu Ala Glu Lys Glu Pro Glu Ile Gly Pro Ile Arg
            20                  25                  30

Ala Ala Gly Arg Ala Ile Pro Leu Arg Thr Arg Ile Ile Leu Ile Val
        35                  40                  45

Val Gly Ile Ala Gly Leu Gly Leu Leu Val Asn Ala Ile Ala Val Ser

```
            50                  55                  60
Ser Leu Met Arg Glu Val Ser Tyr Thr Arg Met Asp Gln Glu Leu Glu
 65                  70                  75                  80

Thr Ser Met Gly Thr Trp Ala His Asn Val Glu Leu Phe Asn Phe Asp
                 85                  90                  95

Gly Val Arg Gln Gly Pro Pro Ser Asp Tyr Tyr Val Ala Lys Val Phe
            100                 105                 110

Pro Asp Gly Ser Ser Ile Ile Phe Asn Asp Ala Gln Ser Ala Pro Asp
            115                 120                 125

Leu Ala Glu Thr Thr Ile Gly Thr Gly Pro His Thr Val Asp Ala Ala
            130                 135                 140

Ser Gly Ser Ala Ser Asn Thr Pro Trp Arg Val Met Ala Glu Lys Asn
145                 150                 155                 160

Gly Asp Ile Ile Thr Val Val Gly Lys Ser Met Gly Arg Glu Thr Asn
                165                 170                 175

Leu Leu Tyr Arg Leu Val Met Val Gln Met Ile Ile Gly Ala Leu Ile
                180                 185                 190

Leu Val Ala Ile Leu Ile Thr Ser Leu Phe Leu Val Arg Arg Ser Leu
            195                 200                 205

Arg Pro Leu Arg Glu Val Glu Glu Thr Ala Thr Arg Ile Ala Gly Gly
    210                 215                 220

Asp Leu Asp Arg Arg Val Pro Gln Trp Pro Met Thr Thr Glu Val Gly
225                 230                 235                 240

Gln Leu Ser Asn Ala Leu Asn Ile Met Leu Glu Gln Leu Gln Ala Ser
                245                 250                 255

Ile Leu Thr Ala Gln Gln Lys Glu Ala Gln Met Arg Arg Phe Val Gly
            260                 265                 270

Asp Ala Ser His Glu Leu Arg Thr Pro Leu Thr Ser Val Lys Gly Phe
            275                 280                 285

Thr Glu Leu Tyr Ser Ser Gly Ala Thr Asp Asp Ala Asn Trp Val Met
    290                 295                 300

Ser Lys Ile Gly Gly Glu Ala Gln Arg Met Ser Val Leu Val Glu Asp
305                 310                 315                 320

Leu Leu Ser Leu Thr Arg Ala Glu Gly Gln Gln Met Glu Lys His Arg
                325                 330                 335

Val Asp Val Leu Glu Leu Ala Leu Ala Val Arg Gly Ser Met Arg Ala
            340                 345                 350

Ala Trp Pro Asp Arg Thr Val Asn Val Ser Asn Lys Ala Glu Ser Ile
            355                 360                 365

Pro Val Val Lys Gly Asp Pro Thr Arg Leu His Gln Val Leu Thr Asn
370                 375                 380

Leu Val Ala Asn Gly Leu Asn His Gly Gly Pro Asp Ala Glu Val Ser
385                 390                 395                 400

Ile Glu Ile Asn Thr Asp Gly Gln Asn Val Arg Ile Leu Val Ala Asp
                405                 410                 415

Asn Gly Val Gly Met Ser Glu Glu Asp Ala Gln His Ile Phe Glu Arg
            420                 425                 430

Phe Tyr Arg Ala Asp Ser Arg Ser Arg Ala Ser Gly Gly Ser Gly
            435                 440                 445

Leu Gly Leu Ala Ile Thr Lys Ser Leu Val Glu Gly His Gly Gly Thr
    450                 455                 460

Val Thr Val Asp Ser Val Gln Gly Glu Gly Thr Val Phe Thr Ile Thr
465                 470                 475                 480
```

Leu Pro Ala Val Ser
            485

<210> SEQ ID NO 55
<211> LENGTH: 485
<212> TYPE: PRT
<213> ORGANISM: Corynebacterium glutamicum

<400> SEQUENCE: 55

Met Glu Asn Pro Tyr Val Ala Ala Leu Asp Asp Glu Asn Gln Glu Val
1               5                   10                  15

Gly Val Lys Lys Glu Ala Glu Lys Glu Pro Glu Ile Gly Pro Ile Arg
            20                  25                  30

Ala Ala Gly Arg Ala Ile Pro Leu Arg Thr Arg Ile Ile Leu Ile Val
        35                  40                  45

Val Gly Ile Ala Gly Leu Gly Leu Leu Val Asn Ala Ile Ala Val Ser
    50                  55                  60

Ser Leu Met Arg Glu Val Ser Tyr Thr Arg Met Asp Gln Glu Leu Glu
65                  70                  75                  80

Thr Ser Met Gly Thr Trp Ala His Asn Val Glu Leu Phe Asn Phe Asp
                85                  90                  95

Gly Val Arg Gln Gly Pro Pro Ser Asp Tyr Tyr Val Ala Lys Val Phe
            100                 105                 110

Pro Asp Gly Ser Ser Ile Ile Phe Asn Asp Ala Gln Ser Ala Pro Asp
        115                 120                 125

Leu Ala Glu Thr Thr Ile Gly Thr Gly Pro His Thr Val Asp Ala Ala
    130                 135                 140

Ser Gly Ser Ala Ser Asn Thr Pro Trp Arg Val Met Ala Glu Lys Asn
145                 150                 155                 160

Gly Asp Ile Ile Thr Val Val Gly Lys Ser Met Gly Arg Glu Thr Asn
                165                 170                 175

Leu Leu Tyr Arg Leu Val Val Val Gln Met Ile Ile Gly Ala Leu Ile
            180                 185                 190

Leu Val Ala Ile Leu Ile Thr Ser Leu Phe Leu Val Arg Arg Ser Leu
        195                 200                 205

Arg Pro Leu Arg Glu Val Glu Glu Thr Ala Thr Arg Ile Ala Gly Gly
    210                 215                 220

Asp Leu Asp Arg Arg Val Pro Gln Trp Pro Met Thr Thr Glu Val Gly
225                 230                 235                 240

Gln Leu Ser Asn Ala Leu Asn Ile Met Leu Glu Gln Leu Gln Ala Ser
                245                 250                 255

Ile Leu Thr Ala Gln Gln Lys Glu Ala Gln Met Arg Arg Phe Val Gly
            260                 265                 270

Asp Ala Ser His Glu Leu Arg Thr Pro Leu Thr Ser Val Lys Gly Phe
        275                 280                 285

Thr Glu Leu Tyr Ser Ser Gly Ala Thr Asp Ala Asn Trp Val Met
    290                 295                 300

Ser Lys Ile Gly Gly Glu Ala Gln Arg Met Ser Val Leu Val Glu Asp
305                 310                 315                 320

Leu Leu Ser Leu Thr Arg Ala Glu Gly Gln Gln Met Glu Lys His Arg
                325                 330                 335

Val Asp Val Leu Glu Leu Ala Leu Ala Val Arg Gly Ser Met Arg Ala
            340                 345                 350

Ala Trp Pro Asp Arg Thr Val Asn Val Ser Asn Lys Ala Glu Ser Ile

```
               355                 360                 365
Pro Val Val Glu Gly Asp Pro Thr Arg Leu His Gln Val Leu Thr Asn
370                 375                 380

Leu Val Ala Asn Gly Leu Asn His Gly Gly Pro Asp Ala Glu Val Ser
385                 390                 395                 400

Ile Glu Ile Asn Thr Asp Gly Gln Asn Val Arg Ile Leu Val Ala Asp
                405                 410                 415

Asn Gly Val Gly Met Ser Glu Asp Ala Gln His Ile Phe Glu Arg
            420                 425                 430

Phe Tyr Arg Ala Asp Ser Ser Arg Ser Arg Ala Ser Gly Gly Ser Gly
            435                 440                 445

Leu Gly Leu Ala Ile Thr Lys Ser Leu Val Glu Gly His Gly Gly Thr
450                 455                 460

Val Thr Val Asp Ser Val Gln Gly Glu Gly Thr Val Phe Thr Ile Thr
465                 470                 475                 480

Leu Pro Ala Val Ser
                485

<210> SEQ ID NO 56
<211> LENGTH: 504
<212> TYPE: PRT
<213> ORGANISM: Corynebacterium callunae

<400> SEQUENCE: 56

Met Glu Asn Pro Tyr Val Ala Ala Leu Asp Lys Asn Ser Asn Phe Gly
1               5                   10                  15

Ala Lys Asp Thr Asp Ser Ala Val Ser Asp Ser Thr Glu Val Ser Gln
                20                  25                  30

Asn Asn Asp Gly Ile Gly Thr Pro Ala Thr Ala Glu Pro Lys Val Gly
            35                  40                  45

Pro Ile Arg Thr Ala Gly Arg Ala Met Pro Leu Arg Thr Arg Ile Ile
50                  55                  60

Leu Leu Val Val Gly Ile Ala Gly Leu Gly Leu Leu Val Asn Ala Val
65                  70                  75                  80

Ala Val Ser Ser Leu Met Arg Glu Val Ser Tyr Thr Arg Met Asp Gln
                85                  90                  95

Asp Leu Glu Ser Ala Met Gly Thr Trp Val Arg Asn Val Glu Leu Phe
                100                 105                 110

Asn Phe Asp Gly Val Arg Gln Gly Pro Pro Ser Asp Tyr Tyr Val Ala
            115                 120                 125

Lys Val Phe Pro Asp Gly Ser Ser Ile Ile Phe Asn Asp Ala Glu Ser
130                 135                 140

Ala Pro Asp Leu Gly Gln Thr Thr Ile Gly Thr Gly Pro His Thr Val
145                 150                 155                 160

Glu Ala Ala Glu Gly Ser Ala Ser Ser Thr His Trp Arg Val Met Ala
                165                 170                 175

Ala Lys Asn Gly Asp Val Ile Thr Val Val Gly Lys Ser Met Gly Arg
                180                 185                 190

Glu Ser Thr Leu Leu Tyr Arg Leu Val Val Gln Met Val Ile Gly
            195                 200                 205

Val Leu Ile Leu Ile Ala Ile Leu Ile Gly Ser Phe Phe Leu Val Arg
            210                 215                 220

Arg Ser Leu Lys Pro Leu Arg Glu Val Glu Glu Thr Ala Ser Arg Ile
225                 230                 235                 240
```

```
Ala Gly Gly Glu Leu Asp Arg Arg Val Pro Gln Trp Pro Met Thr Thr
            245                 250                 255

Glu Val Gly Gln Leu Ala Asn Ala Leu Asn Ile Met Leu Glu Gln Leu
        260                 265                 270

Gln Thr Ser Ile Met Asn Ala Gln Gln Lys Glu Ala Gln Met Arg Arg
    275                 280                 285

Phe Val Gly Asp Ala Ser His Glu Leu Arg Thr Pro Leu Thr Ser Val
290                 295                 300

Lys Gly Phe Thr Glu Leu Tyr Ser Ser Gly Thr Gln Asp Ala Asp
305                 310                 315                 320

Trp Val Leu Ser Lys Ile Gly Gly Glu Ala Gln Arg Met Ser Val Leu
                325                 330                 335

Val Glu Asp Leu Leu Ser Leu Thr Arg Ala Glu Gly Gln Gln Met Glu
            340                 345                 350

Lys His Arg Val Asp Met Leu Glu Leu Ala Leu Ala Val Arg Gly Ser
        355                 360                 365

Leu Lys Ala Ala Trp Pro Asp Arg Thr Val Asn Val Ala Asn Arg Ser
    370                 375                 380

Glu Asn Ile Pro Val Val Glu Gly Asp Pro Thr Arg Leu His Gln Val
385                 390                 395                 400

Leu Thr Asn Leu Val Ala Asn Gly Leu Asn His Gly Gly Pro Glu Ala
                405                 410                 415

Glu Val Asn Ile Gln Val Glu Thr Ala Asp Asp Lys Val Lys Ile Leu
            420                 425                 430

Val Ile Asp Asn Gly Val Gly Met Ser Lys Glu Asp Ala Glu His Ile
        435                 440                 445

Phe Glu Arg Phe Tyr Arg Ala Asp Thr Ser Arg Ser Arg Ala Ser Gly
    450                 455                 460

Gly Ser Gly Leu Gly Leu Ala Ile Thr Lys Ser Leu Val Glu Gly His
465                 470                 475                 480

Gly Gly Thr Ile Thr Val Asp Ser Glu Leu Gly Lys Thr Val Phe
                485                 490                 495

Ser Ile Ile Leu Pro Ala Ala Glu
            500

<210> SEQ ID NO 57
<211> LENGTH: 458
<212> TYPE: PRT
<213> ORGANISM: Corynebacterium crenatum

<400> SEQUENCE: 57

Ile Gly Pro Ile Arg Ala Ala Gly Arg Ala Ile Pro Leu Arg Thr Arg
1               5                   10                  15

Ile Ile Leu Ile Val Val Gly Ile Ala Gly Leu Gly Leu Leu Val Asn
            20                  25                  30

Ala Ile Ala Val Ser Ser Leu Met Arg Glu Val Ser Tyr Thr Arg Met
        35                  40                  45

Asp Gln Glu Leu Glu Thr Ser Met Gly Thr Trp Ala His Asn Val Glu
    50                  55                  60

Leu Phe Asn Phe Asp Gly Val Arg Gln Gly Pro Pro Ser Asp Tyr Tyr
65                  70                  75                  80

Val Ala Lys Val Phe Pro Asp Gly Ser Ser Ile Ile Phe Asn Asp Ala
                85                  90                  95

Gln Ser Ala Pro Asp Leu Ala Glu Thr Thr Ile Gly Thr Gly Pro His
            100                 105                 110
```

Thr Val Asp Ala Ala Ser Gly Ser Ala Ser Asn Thr Pro Trp Arg Val
    115                 120                 125

Met Ala Glu Lys Asn Gly Asp Ile Ile Thr Val Val Gly Lys Ser Met
    130                 135                 140

Gly Arg Glu Thr Asn Leu Leu Tyr Arg Leu Val Met Val Gln Met Ile
145                 150                 155                 160

Ile Gly Ala Leu Ile Leu Val Ala Ile Leu Thr Ser Leu Phe Leu
                165                 170                 175

Val Arg Arg Ser Leu Arg Pro Leu Arg Glu Val Glu Glu Thr Ala Thr
                180                 185                 190

Arg Ile Ala Gly Gly Asp Leu Asp Arg Arg Val Pro Gln Trp Pro Met
                195                 200                 205

Thr Thr Glu Val Gly Gln Leu Ser Asn Ala Leu Asn Ile Met Leu Glu
    210                 215                 220

Gln Leu Gln Ala Ser Ile Leu Ser Ala Gln Gln Lys Glu Ala Gln Met
225                 230                 235                 240

Arg Arg Phe Val Gly Asp Ala Ser His Glu Leu Arg Thr Pro Leu Thr
                245                 250                 255

Ser Val Lys Gly Phe Thr Glu Leu Tyr Ser Ser Gly Ala Thr Asp Asp
                260                 265                 270

Ala Asn Trp Val Met Ser Lys Ile Gly Gly Glu Ala Gln Arg Met Ser
                275                 280                 285

Val Leu Val Glu Asp Leu Leu Ser Leu Thr Arg Ala Glu Gly Gln Gln
                290                 295                 300

Met Glu Lys His Arg Val Asp Val Leu Glu Leu Ala Leu Ala Val Arg
305                 310                 315                 320

Gly Ser Met Arg Ala Ala Trp Pro Asp Arg Thr Val Asn Val Ser Asn
                325                 330                 335

Lys Ala Ala Ser Ile Pro Val Val Glu Gly Asp Pro Thr Arg Leu His
                340                 345                 350

Gln Val Leu Thr Asn Leu Val Ala Asn Gly Leu Asn His Gly Gly Pro
                355                 360                 365

Asp Ala Glu Val Ser Ile Glu Ile Asn Thr Asp Gly Gln Asn Val Arg
                370                 375                 380

Ile Leu Val Ala Asp Asn Gly Val Gly Met Ser Glu Glu Asp Ala Gln
385                 390                 395                 400

His Ile Phe Glu Arg Phe Tyr Arg Ala Asp Ser Ser Arg Ser Arg Ala
                405                 410                 415

Ser Gly Gly Ser Gly Leu Gly Leu Ala Ile Thr Lys Ser Leu Val Glu
                420                 425                 430

Gly His Gly Gly Thr Val Thr Val Asp Ser Val Gln Gly Glu Gly Thr
                435                 440                 445

Val Phe Thr Ile Thr Leu Pro Ala Val Ser
    450                 455

<210> SEQ ID NO 58
<211> LENGTH: 471
<212> TYPE: PRT
<213> ORGANISM: Corynebacterium efficiens

<400> SEQUENCE: 58

Met Thr Ala Pro Glu Asn Pro His Ala Gln Val Thr Pro Val Gly Arg
1               5                   10                  15

Phe Arg Gln Ala Ala Arg Gly Val Pro Leu Arg Thr Arg Ile Ile Leu

-continued

```
                20                  25                  30
Leu Val Val Gly Ile Ala Gly Leu Gly Leu Val Asn Ala Ile Ala
                35                  40                  45
Val Ser Ser Leu Met Arg Glu Val Ser Tyr Ser Arg Met Asp Gln Glu
50                  55                  60
Leu Glu Ser Ala Met Asn Ser Trp Ala Gln Thr Ala Glu Leu Phe Gly
65                  70                  75                  80
Ser Ile Thr Leu Gly Pro Pro Ser Asp Tyr Tyr Val Arg Ile Phe
                85                  90                  95
Pro Asp Gly Ser His Met Val Phe Asn Gln Ser Asp Ser Ala Pro Asp
                100                 105                 110
Leu Gly Glu Thr Thr Ile Gly Ile Gly Pro His Thr Ala Ser Ala Ala
                115                 120                 125
Pro Gly Ser Ser Ser Ser Val Pro Trp Arg Val Ile Ala Ile Ser Asp
                130                 135                 140
Asn Gly Thr Ile Thr Val Val Gly Lys Ser Leu Ala Pro Glu Ser Met
145                 150                 155                 160
Leu Leu Tyr Arg Leu Val Ile Val Gln Leu Val Ile Gly Met Leu Ile
                165                 170                 175
Val Val Ala Ile Leu Leu Ser Ser Leu Tyr Leu Val Asn Arg Ser Leu
                180                 185                 190
Arg Pro Leu Arg Glu Val Glu Lys Thr Ala Lys Ser Ile Ala Gly Gly
                195                 200                 205
Asp Leu Asp Arg Arg Val Pro Gln Trp Pro Met Thr Thr Glu Val Gly
                210                 215                 220
Gln Leu Ala Asn Ala Leu Asn Ile Met Leu Glu Gln Leu Gln Ala Ser
225                 230                 235                 240
Ile Leu Ser Ala Gln Glu Lys Glu Ser Gln Met Arg Arg Phe Val Gly
                245                 250                 255
Asp Ala Ser His Glu Leu Arg Thr Pro Leu Thr Ser Val Lys Gly Tyr
                260                 265                 270
Ser Glu Leu Tyr His Ser Gly Ala Thr Arg Asp Ala Asp Trp Val Leu
                275                 280                 285
Ser Lys Ile Ser Gly Glu Ala Gln Arg Met Ser Val Leu Val Glu Asp
                290                 295                 300
Leu Leu Ser Leu Thr Arg Ala Glu Gly Gln Gln Met Glu Lys Arg Pro
305                 310                 315                 320
Val Asp Val Leu Glu Leu Ser Leu Ser Val Ala Ser Ser Met Arg Ala
                325                 330                 335
Ala Trp Pro Glu Arg Ser Ile Thr Val Val Asn Lys Thr Gly Ser Leu
                340                 345                 350
Pro Val Val Glu Gly Asp Ala Thr Arg Leu His Gln Val Leu Thr Asn
                355                 360                 365
Leu Val Asn Asn Gly Leu Asn His Gly Gly Pro Asp Ala Ser Val Glu
                370                 375                 380
Ile Glu Ile Ser Ala Glu Gly Gly Ser Val Leu Val Arg Val Val Asp
385                 390                 395                 400
Asp Gly Val Gly Met Thr Ala Glu Asp Ala Gln His Ile Phe Glu Arg
                405                 410                 415
Phe Tyr Arg Thr Asp Thr Ser Arg Ser Arg Ala Ser Gly Gly Ser Gly
                420                 425                 430
Leu Gly Leu Ala Ile Thr Lys Ser Leu Val Glu Gly His Arg Gly Thr
                435                 440                 445
```

Ile Thr Val Asp Ser Glu Val Gly Glu Gly Thr Val Phe Thr Ile Thr
450                 455                 460

Leu Pro Ser Arg Met Glu Asp
465                 470

<210> SEQ ID NO 59
<211> LENGTH: 65
<212> TYPE: PRT
<213> ORGANISM: Corynebacterium glutamicum

<400> SEQUENCE: 59

Gln Met Arg Arg Phe Val Gly Asp Ala Ser His Glu Leu Arg Thr Pro
1               5                   10                  15

Leu Thr Ser Val Lys Gly Phe Thr Glu Leu Tyr Ser Ser Gly Ala Thr
            20                  25                  30

Asp Asp Ala Asn Cys Val Met Ser Lys Ile Gly Gly Glu Ala Gln Arg
        35                  40                  45

Met Ser Val Leu Val Glu Asp Leu Leu Ser Leu Thr Arg Ala Glu Gly
    50                  55                  60

Gln
65

<210> SEQ ID NO 60
<211> LENGTH: 65
<212> TYPE: PRT
<213> ORGANISM: Corynebacterium glutamicum

<400> SEQUENCE: 60

Gln Met Arg Arg Phe Val Gly Asp Ala Ser His Glu Leu Arg Thr Pro
1               5                   10                  15

Leu Thr Ser Val Lys Gly Phe Thr Glu Leu Tyr Ser Ser Gly Ala Thr
            20                  25                  30

Asp Asp Ala Asn Trp Val Met Ser Lys Ile Gly Gly Glu Ala Gln Arg
        35                  40                  45

Met Ser Val Leu Val Glu Asp Leu Leu Ser Leu Thr Arg Ala Glu Gly
    50                  55                  60

Gln
65

<210> SEQ ID NO 61
<211> LENGTH: 65
<212> TYPE: PRT
<213> ORGANISM: Corynebacterium glutamicum

<400> SEQUENCE: 61

Gln Met Arg Arg Phe Val Gly Asp Ala Ser His Glu Leu Arg Thr Pro
1               5                   10                  15

Leu Thr Ser Val Lys Gly Phe Thr Glu Leu Tyr Ser Ser Gly Ala Thr
            20                  25                  30

Asp Asp Ala Asn Trp Val Met Ser Lys Ile Gly Gly Glu Ala Gln Arg
        35                  40                  45

Met Ser Val Leu Val Glu Asp Leu Leu Ser Leu Thr Arg Ala Glu Gly
    50                  55                  60

Gln
65

<210> SEQ ID NO 62
<211> LENGTH: 65

<212> TYPE: PRT
<213> ORGANISM: Corynebacterium glutamicum

<400> SEQUENCE: 62

Gln Met Arg Arg Phe Val Gly Asp Ala Ser His Glu Leu Arg Thr Pro
1               5                   10                  15

Leu Thr Ser Val Lys Gly Phe Thr Glu Leu Tyr Ser Ser Gly Ala Thr
            20                  25                  30

Asp Asp Ala Asn Trp Val Met Ser Lys Ile Gly Gly Glu Ala Gln Arg
        35                  40                  45

Met Ser Val Leu Val Glu Asp Leu Leu Ser Leu Thr Arg Ala Glu Gly
    50                  55                  60

Gln
65

<210> SEQ ID NO 63
<211> LENGTH: 65
<212> TYPE: PRT
<213> ORGANISM: Corynebacterium glutamicum

<400> SEQUENCE: 63

Gln Met Arg Arg Phe Val Gly Asp Ala Ser His Glu Leu Arg Thr Pro
1               5                   10                  15

Leu Thr Ser Val Lys Gly Phe Thr Glu Leu Tyr Ser Ser Gly Ala Thr
            20                  25                  30

Asp Asp Ala Asn Trp Val Met Ser Lys Ile Gly Gly Glu Ala Gln Arg
        35                  40                  45

Met Ser Val Leu Val Glu Asp Leu Leu Ser Leu Thr Arg Ala Glu Gly
    50                  55                  60

Gln
65

<210> SEQ ID NO 64
<211> LENGTH: 65
<212> TYPE: PRT
<213> ORGANISM: Corynebacterium callunae

<400> SEQUENCE: 64

Gln Met Arg Arg Phe Val Gly Asp Ala Ser His Glu Leu Arg Thr Pro
1               5                   10                  15

Leu Thr Ser Val Lys Gly Phe Thr Glu Leu Tyr Ser Ser Gly Ala Thr
            20                  25                  30

Gln Asp Ala Asp Trp Val Leu Ser Lys Ile Gly Gly Glu Ala Gln Arg
        35                  40                  45

Met Ser Val Leu Val Glu Asp Leu Leu Ser Leu Thr Arg Ala Glu Gly
    50                  55                  60

Gln
65

<210> SEQ ID NO 65
<211> LENGTH: 65
<212> TYPE: PRT
<213> ORGANISM: Corynebacterium crenatum

<400> SEQUENCE: 65

Gln Met Arg Arg Phe Val Gly Asp Ala Ser His Glu Leu Arg Thr Pro
1               5                   10                  15

Leu Thr Ser Val Lys Gly Phe Thr Glu Leu Tyr Ser Ser Gly Ala Thr
            20                  25                  30

Asp Asp Ala Asn Trp Val Met Ser Lys Ile Gly Gly Glu Ala Gln Arg
    35                  40                  45

Met Ser Val Leu Val Glu Asp Leu Leu Ser Leu Thr Arg Ala Glu Gly
    50                  55                  60

Gln
65

<210> SEQ ID NO 66
<211> LENGTH: 65
<212> TYPE: PRT
<213> ORGANISM: Corynebacterium efficiens

<400> SEQUENCE: 66

Gln Met Arg Arg Phe Val Gly Asp Ala Ser His Glu Leu Arg Thr Pro
1               5                   10                  15

Leu Thr Ser Val Lys Gly Tyr Ser Glu Leu Tyr His Ser Gly Ala Thr
                20                  25                  30

Arg Asp Ala Asp Trp Val Leu Ser Lys Ile Ser Gly Glu Ala Gln Arg
    35                  40                  45

Met Ser Val Leu Val Glu Asp Leu Leu Ser Leu Thr Arg Ala Glu Gly
    50                  55                  60

Gln
65

<210> SEQ ID NO 67
<211> LENGTH: 1500
<212> TYPE: DNA
<213> ORGANISM: Corynebacterium glutamicum

<400> SEQUENCE: 67

| | |
|---|---|
| atgtttaaca accgtatccg cactgcagct ctcgctggtg caatcgcaat ctccaccgca | 60 |
| gcttccggcg tagctatccc agcattcgct caggagacca acccaacctt caacatcaac | 120 |
| aacggcttca cgatgctga tggatccacc atccagccag ttgagccagt taaccacacc | 180 |
| gaggaaaccc tccgcgacct gactgactcc accggcgctt acctggaaga gttccagtac | 240 |
| ggcaacgttg aggaaatcgt tgaagcatac ctgcaggttc aggcttccgc agacggattc | 300 |
| gatccttctg agcaggctgc ttacgaggct ttcgaggctg ctcgcgttcg tgcatcccag | 360 |
| gagctcgcgg cttccgctga gaccatcact aagacccgcg agtccgttgc ttacgcactc | 420 |
| aaggctgacc gcgaagctac cgcagctttc gaggcttacc tcagcgctct tcgtcaggtt | 480 |
| tcagtcatca cgatctgat cgctgatgct aacgccaaga caagactga ctttgcagag | 540 |
| atcgagctct acgatgttct ttacaccgac gccgacatct ctggcgatgc tccacttctt | 600 |
| gctcctgcat acaaggagct gaaggacctt caggctgagg ttgacgcaga cttcgagtgg | 660 |
| ttgggcgagt cgcaattga taacaatgaa dacaactacg tcattcgtac tcacatccct | 720 |
| gctgtagagg cactcaaggc agcgatcgat tcactggtcg acaccgttga gccacttcgt | 780 |
| gcagacgcta tcgctaagaa catcgaggct cagaagtctg acgttctggt tccccagctc | 840 |
| ttcctcgagc gtgcaactgc acagcgcgac accctgcgtg ttgtagaggc aatcttctct | 900 |
| acctctgctc gttacgttga actctacgag aacgtcgaga cgttaacgt tgagaacaag | 960 |
| acccttcgcc agcactactc tttccctgatc cctaacctct tcatcgcagc ggttggcaac | 1020 |
| atcaacgagc tcaacaatgc agatcaggct gcacgtgagc tcttcctcga ttgggacacc | 1080 |
| gacctcacca ccaacgatga ggacgaagct tactaccagg ctaagctcga cttcgctatc | 1140 |

```
gagacctacg caaagatcct gatcaacggt gaagtttggc aggagccact cgcttacgtc    1200
cagaacctgg atgcaggcgc acgtcaggaa gcagctgacc gcgaagcaga gcgcgcagct    1260
gacgcagcat accgcgctga gcagctccgc atcgctcagg aagcagctga cgctcagaag    1320
gctctcgctg aggctcttgc taatgcaggc aacaacgaca acggtggcga caactcctcc    1380
gacgacaagg gaaccggttc ttccgacatc ggaacctggg accttccgc agcaattgca     1440 gctatcatcg cagcaatcgc agctatcttc ccattcctct ccggtatcgt taagttctaa    1500
```

<210> SEQ ID NO 68
<211> LENGTH: 499
<212> TYPE: PRT
<213> ORGANISM: Corynebacterium glutamicum

<400> SEQUENCE: 68

```
Met Phe Asn Asn Arg Ile Arg Thr Ala Ala Leu Ala Gly Ala Ile Ala
1               5                  10                  15

Ile Ser Thr Ala Ala Ser Gly Val Ala Ile Pro Ala Phe Ala Gln Glu
            20                  25                  30

Thr Asn Pro Thr Phe Asn Ile Asn Asn Gly Phe Asn Asp Ala Asp Gly
        35                  40                  45

Ser Thr Ile Gln Pro Val Glu Pro Val Asn His Thr Glu Glu Thr Leu
    50                  55                  60

Arg Asp Leu Thr Asp Ser Thr Gly Ala Tyr Leu Glu Glu Phe Gln Tyr
65                  70                  75                  80

Gly Asn Val Glu Glu Ile Val Glu Ala Tyr Leu Gln Val Gln Ala Ser
                85                  90                  95

Ala Asp Gly Phe Asp Pro Ser Glu Gln Ala Ala Tyr Glu Ala Phe Glu
            100                 105                 110

Ala Ala Arg Val Arg Ala Ser Gln Glu Leu Ala Ala Ser Ala Glu Thr
        115                 120                 125

Ile Thr Lys Thr Arg Glu Ser Val Ala Tyr Ala Leu Lys Ala Asp Arg
    130                 135                 140

Glu Ala Thr Ala Ala Phe Glu Ala Tyr Leu Ser Ala Leu Arg Gln Val
145                 150                 155                 160

Ser Val Ile Asn Asp Leu Ile Ala Asp Ala Asn Ala Lys Asn Lys Thr
                165                 170                 175

Asp Phe Ala Glu Ile Glu Leu Tyr Asp Val Leu Tyr Thr Asp Ala Asp
            180                 185                 190

Ile Ser Gly Asp Ala Pro Leu Leu Ala Pro Ala Tyr Lys Glu Leu Lys
        195                 200                 205

Asp Leu Gln Ala Glu Val Asp Ala Asp Phe Glu Trp Leu Gly Glu Phe
    210                 215                 220

Ala Ile Asp Asn Asn Glu Asp Asn Tyr Val Ile Arg Thr His Ile Pro
225                 230                 235                 240

Ala Val Glu Ala Leu Lys Ala Ala Ile Asp Ser Leu Val Asp Thr Val
                245                 250                 255

Glu Pro Leu Arg Ala Asp Ala Ile Ala Lys Asn Ile Glu Ala Gln Lys
            260                 265                 270

Ser Asp Val Leu Val Pro Gln Leu Phe Leu Glu Arg Ala Thr Ala Gln
        275                 280                 285

Arg Asp Thr Leu Arg Val Val Glu Ala Ile Phe Ser Thr Ser Ala Arg
    290                 295                 300

Tyr Val Glu Leu Tyr Glu Asn Val Glu Asn Val Asn Val Glu Asn Lys
305                 310                 315                 320
```

```
Thr Leu Arg Gln His Tyr Ser Ser Leu Ile Pro Asn Leu Phe Ile Ala
            325                 330                 335

Ala Val Gly Asn Ile Asn Glu Leu Asn Asn Ala Asp Gln Ala Ala Arg
            340                 345                 350

Glu Leu Phe Leu Asp Trp Asp Thr Asp Leu Thr Thr Asn Asp Glu Asp
            355                 360                 365

Glu Ala Tyr Tyr Gln Ala Lys Leu Asp Phe Ala Ile Glu Thr Tyr Ala
            370                 375                 380

Lys Ile Leu Ile Asn Gly Glu Val Trp Gln Glu Pro Leu Ala Tyr Val
385                 390                 395                 400

Gln Asn Leu Asp Ala Gly Ala Arg Gln Glu Ala Ala Asp Arg Glu Ala
            405                 410                 415

Glu Arg Ala Ala Asp Ala Ala Tyr Arg Ala Glu Gln Leu Arg Ile Ala
            420                 425                 430

Gln Glu Ala Ala Asp Ala Gln Lys Ala Leu Glu Ala Leu Ala Asn
            435                 440                 445

Ala Gly Asn Asn Asp Asn Gly Asp Asn Ser Ser Asp Asp Lys Gly
            450                 455                 460

Thr Gly Ser Ser Asp Ile Gly Thr Trp Gly Pro Phe Ala Ala Ile Ala
465                 470                 475                 480

Ala Ile Ile Ala Ala Ile Ala Ala Ile Phe Pro Phe Leu Ser Gly Ile
            485                 490                 495

Val Lys Phe

<210> SEQ ID NO 69
<211> LENGTH: 318
<212> TYPE: DNA
<213> ORGANISM: Corynebacterium glutamicum

<400> SEQUENCE: 69
atgtccctcg gaccatggga aattggaatc attgtcctgc tgatcatcgt gctgttcggc      60
gcgaagaagc tgcctgatgc agctcgttcc atcggccgtt ccatgcgcat cttcaagtct     120
gaagtcaaag aaatgaacaa ggacggcgat accccagaac aacagcagca gcctcagcag     180
cagattgcgc ccaaccagat cgaggctcct cagccaaact tgagcagca ctaccaggga      240 cagcaggttc agcagcctca gaaccctcag acccctgact accgtcagaa ctacgaggat     300
ccaaaccgca cctcttaa                                                   318

<210> SEQ ID NO 70
<211> LENGTH: 105
<212> TYPE: PRT
<213> ORGANISM: Corynebacterium glutamicum

<400> SEQUENCE: 70

Met Ser Leu Gly Pro Trp Glu Ile Gly Ile Ile Val Leu Leu Ile Ile
1               5                   10                  15

Val Leu Phe Gly Ala Lys Lys Leu Pro Asp Ala Ala Arg Ser Ile Gly
            20                  25                  30

Arg Ser Met Arg Ile Phe Lys Ser Glu Val Lys Glu Met Asn Lys Asp
            35                  40                  45

Gly Asp Thr Pro Glu Gln Gln Gln Gln Pro Gln Gln Ile Ala Pro
            50                  55                  60

Asn Gln Ile Glu Ala Pro Gln Pro Asn Phe Glu Gln His Tyr Gln Gly
65                  70                  75                  80
```

Gln Gln Val Gln Gln Pro Gln Asn Pro Gln Thr Pro Asp Tyr Arg Gln
            85                  90                  95

Asn Tyr Glu Asp Pro Asn Arg Thr Ser
        100                 105

<210> SEQ ID NO 71
<211> LENGTH: 471
<212> TYPE: DNA
<213> ORGANISM: Corynebacterium glutamicum

<400> SEQUENCE: 71
atgttttcta gcgtgggttg gggagagatc ttcctcttag tcgttgtggg ccttgttgtc      60
atcggcccgg aacggttgcc tcgtttgatc caggacgcac gcgctgcgct gctcgctgca     120
cgtaccgcta tcgacaatgc aaagcagtcg ttggacagtg attttggttc ggaatttgat     180
gaaatccgaa agccactaac ccaggttgca cagtacagcc ggatgagccc caagacggcc     240
atcactaagg cgttatttga taatgattcc tcgttcctgg atgactttga tccaaagaag     300
atcatggccg aaggaacaga aggcgaagct cagcgcaaca agcaggcagc tgacaacaat     360
gcgaatgtgg tggaacgtcc agctgatggt tccaccgcac gcccaacgca aaacgatcca     420
aaagacggcc cgaattactc aggtggcgtc tcttggaccg atattattta g              471

<210> SEQ ID NO 72
<211> LENGTH: 156
<212> TYPE: PRT
<213> ORGANISM: Corynebacterium glutamicum

<400> SEQUENCE: 72

Met Phe Ser Ser Val Gly Trp Gly Glu Ile Phe Leu Leu Val Val Val
1               5                   10                  15

Gly Leu Val Val Ile Gly Pro Glu Arg Leu Pro Arg Leu Ile Gln Asp
            20                  25                  30

Ala Arg Ala Ala Leu Leu Ala Ala Arg Thr Ala Ile Asp Asn Ala Lys
        35                  40                  45

Gln Ser Leu Asp Ser Asp Phe Gly Ser Glu Phe Asp Glu Ile Arg Lys
    50                  55                  60

Pro Leu Thr Gln Val Ala Gln Tyr Ser Arg Met Ser Pro Lys Thr Ala
65                  70                  75                  80

Ile Thr Lys Ala Leu Phe Asp Asn Asp Ser Ser Phe Leu Asp Asp Phe
                85                  90                  95

Asp Pro Lys Lys Ile Met Ala Glu Gly Thr Glu Gly Glu Ala Gln Arg
            100                 105                 110

Asn Lys Gln Ala Ala Asp Asn Asn Ala Asn Val Val Glu Arg Pro Ala
        115                 120                 125

Asp Gly Ser Thr Ala Arg Pro Thr Gln Asn Asp Pro Lys Asp Gly Pro
    130                 135                 140

Asn Tyr Ser Gly Gly Val Ser Trp Thr Asp Ile Ile
145                 150                 155

<210> SEQ ID NO 73
<211> LENGTH: 945
<212> TYPE: DNA
<213> ORGANISM: Corynebacterium glutamicum

<400> SEQUENCE: 73
atgtccattg ttgagcacat caaagagttt cgacgccgac ttcttatcgc tctggcgggc      60
atcctcgtgg gcaccattat cggctttatt tggtacgatt tctcattttg gcagatcccc     120

```
actttgggcg agctgctgag ggatccgtac tgttctctgc ctgctgaatc ccgctgggcc      180
atgagcgact cagaggaatg tcgactgctc gcaaccggcc cgtttgatcc attcatgctt      240
cgccttaaag tagcggcgtt ggtgggtatg gttcttggct cacccgtgtg gctgagccag      300
ctgtggggct ttatcacccc aggtttgatg aagaatgagc gccgttacac cgcaatcttc      360
gtcacgattg ctgttgtgct gtttgtcggc ggtgctgttc ttgcgtactt cgtcgttgca      420
tatggtttgg agttcctcct taccattggt ggagacaccc aggcagcggc cctgactggt      480
gataagtact tcggattctt gctcgcgttg ttggcgattt tcggcgtgag cttcgaagtt      540
ccactggtga tcggcatgct caacattgtg gtatcttgc cttacgatgc cattaaagat       600
aagcgacgca tgatcatcat gattttgttc gtgttcgctg ctttcatgac acccggccag      660
gatcctttca ccatgttggt gttggcgctt tcactcaccg ttctggtaga gcttgccctg      720
cagttctgtc gtttcaacga caaacgccgg gacaagaagc gcccagaatg gcttgatggc      780 gatgaccctct ctgcatcacc actggatact tctgctggtg gagaagatgc tccaagccca    840
gtcgaaaccc cagaggcggt ggagccttcg cggatgctga acccaagtgg ggaggcgtcg      900
ataagctata aacccgggcg cgccgacttc ggtgacgtgc tctag                     945
```

<210> SEQ ID NO 74
<211> LENGTH: 314
<212> TYPE: PRT
<213> ORGANISM: Corynebacterium glutamicum

<400> SEQUENCE: 74

```
Met Ser Ile Val Glu His Ile Lys Glu Phe Arg Arg Arg Leu Leu Ile
1               5                   10                  15

Ala Leu Ala Gly Ile Leu Val Gly Thr Ile Ile Gly Phe Ile Trp Tyr
            20                  25                  30

Asp Phe Ser Phe Trp Gln Ile Pro Thr Leu Gly Glu Leu Leu Arg Asp
        35                  40                  45

Pro Tyr Cys Ser Leu Pro Ala Glu Ser Arg Trp Ala Met Ser Asp Ser
    50                  55                  60

Glu Glu Cys Arg Leu Leu Ala Thr Gly Pro Phe Asp Pro Phe Met Leu
65                  70                  75                  80

Arg Leu Lys Val Ala Ala Leu Val Gly Met Val Leu Gly Ser Pro Val
                85                  90                  95

Trp Leu Ser Gln Leu Trp Gly Phe Ile Thr Pro Gly Leu Met Lys Asn
            100                 105                 110

Glu Arg Arg Tyr Thr Ala Ile Phe Val Thr Ile Ala Val Val Leu Phe
        115                 120                 125

Val Gly Gly Ala Val Leu Ala Tyr Phe Val Val Ala Tyr Gly Leu Glu
    130                 135                 140

Phe Leu Leu Thr Ile Gly Gly Asp Thr Gln Ala Ala Ala Leu Thr Gly
145                 150                 155                 160

Asp Lys Tyr Phe Gly Phe Leu Leu Ala Leu Leu Ala Ile Phe Gly Val
                165                 170                 175

Ser Phe Glu Val Pro Leu Val Ile Gly Met Leu Asn Ile Val Gly Ile
            180                 185                 190

Leu Pro Tyr Asp Ala Ile Lys Asp Lys Arg Arg Met Ile Ile Met Ile
        195                 200                 205

Leu Phe Val Phe Ala Ala Phe Met Thr Pro Gly Gln Asp Pro Phe Thr
    210                 215                 220
```

```
Met Leu Val Leu Ala Leu Ser Leu Thr Val Leu Val Glu Leu Ala Leu
225                 230                 235                 240

Gln Phe Cys Arg Phe Asn Asp Lys Arg Asp Lys Lys Arg Pro Glu
                245                 250                 255

Trp Leu Asp Gly Asp Asp Leu Ser Ala Ser Pro Leu Asp Thr Ser Ala
                260                 265                 270

Gly Gly Glu Asp Ala Pro Ser Pro Val Glu Thr Pro Glu Ala Val Glu
                275                 280                 285

Pro Ser Arg Met Leu Asn Pro Ser Gly Glu Ala Ser Ile Ser Tyr Lys
                290                 295                 300

Pro Gly Arg Ala Asp Phe Gly Asp Val Leu
305                 310
```

<210> SEQ ID NO 75
<211> LENGTH: 39
<212> TYPE: PRT
<213> ORGANISM: Escherichia coli

<400> SEQUENCE: 75

```
Met Asn Asn Asn Asp Leu Phe Gln Ala Ser Arg Arg Arg Phe Leu Ala
1               5                   10                  15

Gln Leu Gly Gly Leu Thr Val Ala Gly Met Leu Gly Pro Ser Leu Leu
                20                  25                  30

Thr Pro Arg Arg Ala Thr Ala
            35
```

<210> SEQ ID NO 76
<211> LENGTH: 27
<212> TYPE: PRT
<213> ORGANISM: Escherichia coli

<400> SEQUENCE: 76

```
Met Ser Leu Ser Arg Arg Gln Phe Ile Gln Ala Ser Gly Ile Ala Leu
1               5                   10                  15

Cys Ala Gly Ala Val Pro Leu Lys Ala Ser Ala
                20                  25
```

<210> SEQ ID NO 77
<211> LENGTH: 48
<212> TYPE: PRT
<213> ORGANISM: Bacillus subtilis

<400> SEQUENCE: 77

```
Met Ala Tyr Asp Ser Arg Phe Asp Glu Trp Val Gln Lys Leu Lys Glu
1               5                   10                  15

Glu Ser Phe Gln Asn Asn Thr Phe Asp Arg Arg Lys Phe Ile Gln Gly
                20                  25                  30

Ala Gly Lys Ile Ala Gly Leu Ser Leu Gly Leu Thr Ile Ala Gln Ser
            35                  40                  45
```

<210> SEQ ID NO 78
<211> LENGTH: 34
<212> TYPE: PRT
<213> ORGANISM: Bacillus subtilis

<400> SEQUENCE: 78

```
Met Lys Phe Val Lys Arg Arg Thr Thr Ala Leu Val Thr Thr Leu Met
1               5                   10                  15

Leu Ser Val Thr Ser Leu Phe Ala Leu Gln Pro Ser Ala Lys Ala Ala
                20                  25                  30
```

Glu His

<210> SEQ ID NO 79
<211> LENGTH: 30
<212> TYPE: PRT
<213> ORGANISM: Arthrobacter globiformis

<400> SEQUENCE: 79

```
Met Met Asn Leu Ser Arg Arg Thr Leu Leu Thr Thr Gly Ser Ala Ala
1               5                   10                  15

Thr Leu Ala Tyr Ala Leu Gly Met Ala Gly Ser Ala Gln Ala
            20                  25                  30
```

<210> SEQ ID NO 80
<211> LENGTH: 7
<212> TYPE: PRT
<213> ORGANISM: Artificial Sequence
<220> FEATURE:
<223> OTHER INFORMATION: Twin-Arginine Motif
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 80

```
Xaa Arg Arg Xaa Phe Leu Lys
1               5
```

<210> SEQ ID NO 81
<211> LENGTH: 5
<212> TYPE: PRT
<213> ORGANISM: Artificial Sequence
<220> FEATURE:
<223> OTHER INFORMATION: Twin-Arginine Motif
<220> FEATURE:
<221> NAME/KEY: misc_feature
<222> LOCATION: (3)..(5)
<223> OTHER INFORMATION: Xaa can be any naturally occurring amino acid

<400> SEQUENCE: 81

```
Arg Arg Xaa Xaa Xaa
1               5
```

<210> SEQ ID NO 82
<211> LENGTH: 43
<212> TYPE: PRT
<213> ORGANISM: Corynebacterium glutamicum

<400> SEQUENCE: 82

```
Met Arg Asp Thr Ala Phe Arg Ser Ile Lys Ala Lys Ala Gln Ala Lys
1               5                   10                  15

Arg Arg Ser Leu Trp Ile Ala Ala Gly Ala Val Pro Thr Ala Ile Ala
            20                  25                  30

Leu Thr Met Ser Leu Ala Pro Met Ala Ser Ala
        35                  40
```

<210> SEQ ID NO 83
<211> LENGTH: 30
<212> TYPE: PRT
<213> ORGANISM: Corynebacterium glutamicum

<400> SEQUENCE: 83

```
Met Phe Asn Asn Arg Ile Arg Thr Ala Ala Leu Ala Gly Ala Ile Ala
1               5                   10                  15

Ile Ser Thr Ala Ala Ser Gly Val Ala Ile Pro Ala Phe Ala
                20                  25                  30
```

<210> SEQ ID NO 84
<211> LENGTH: 25
<212> TYPE: PRT
<213> ORGANISM: Corynebacterium stationis

<400> SEQUENCE: 84

```
Met Lys Arg Met Lys Ser Leu Ala Ala Ala Leu Thr Val Ala Gly Ala
1               5                   10                  15

Met Leu Ala Ala Pro Val Ala Thr Ala
                20                  25
```

<210> SEQ ID NO 85
<211> LENGTH: 469
<212> TYPE: PRT
<213> ORGANISM: Corynebacterium glutamicum

<400> SEQUENCE: 85

```
Gln Glu Thr Asn Pro Thr Phe Asn Ile Asn Asn Gly Phe Asn Asp Ala
1               5                   10                  15

Asp Gly Ser Thr Ile Gln Pro Val Glu Pro Val Asn His Thr Glu Glu
                20                  25                  30

Thr Leu Arg Asp Leu Thr Asp Ser Thr Gly Ala Tyr Leu Glu Glu Phe
            35                  40                  45

Gln Tyr Gly Asn Val Glu Glu Ile Val Glu Ala Tyr Leu Gln Val Gln
        50                  55                  60

Ala Ser Ala Asp Gly Phe Asp Pro Ser Glu Gln Ala Ala Tyr Glu Ala
65                  70                  75                  80

Phe Glu Ala Ala Arg Val Arg Ala Ser Gln Glu Leu Ala Ala Ser Ala
                85                  90                  95

Glu Thr Ile Thr Lys Thr Arg Glu Ser Val Ala Tyr Ala Leu Lys Ala
            100                 105                 110

Asp Arg Glu Ala Thr Ala Ala Phe Glu Ala Tyr Leu Ser Ala Leu Arg
        115                 120                 125

Gln Val Ser Val Ile Asn Asp Leu Ile Ala Asp Ala Asn Ala Lys Asn
    130                 135                 140

Lys Thr Asp Phe Ala Glu Ile Glu Leu Tyr Asp Val Leu Tyr Thr Asp
145                 150                 155                 160

Ala Asp Ile Ser Gly Asp Ala Pro Leu Leu Ala Pro Ala Tyr Lys Glu
                165                 170                 175

Leu Lys Asp Leu Gln Ala Glu Val Asp Ala Asp Phe Glu Trp Leu Gly
            180                 185                 190

Glu Phe Ala Ile Asp Asn Asn Glu Asp Asn Tyr Val Ile Arg Thr His
        195                 200                 205

Ile Pro Ala Val Glu Ala Leu Lys Ala Ala Ile Asp Ser Leu Val Asp
    210                 215                 220

Thr Val Glu Pro Leu Arg Ala Asp Ala Ile Ala Lys Asn Ile Glu Ala
225                 230                 235                 240

Gln Lys Ser Asp Val Leu Val Pro Gln Leu Phe Leu Glu Arg Ala Thr
                245                 250                 255

Ala Gln Arg Asp Thr Leu Arg Val Val Glu Ala Ile Phe Ser Thr Ser
            260                 265                 270
```

-continued

```
Ala Arg Tyr Val Glu Leu Tyr Glu Asn Val Glu Asn Val Asn Val Glu
        275                 280                 285

Asn Lys Thr Leu Arg Gln His Tyr Ser Ser Leu Ile Pro Asn Leu Phe
290                 295                 300

Ile Ala Ala Val Gly Asn Ile Asn Glu Leu Asn Asn Ala Asp Gln Ala
305                 310                 315                 320

Ala Arg Glu Leu Phe Leu Asp Trp Asp Thr Asp Leu Thr Thr Asn Asp
            325                 330                 335

Glu Asp Glu Ala Tyr Tyr Gln Ala Lys Leu Asp Phe Ala Ile Glu Thr
        340                 345                 350

Tyr Ala Lys Ile Leu Ile Asn Gly Glu Val Trp Gln Glu Pro Leu Ala
            355                 360                 365

Tyr Val Gln Asn Leu Asp Ala Gly Ala Arg Gln Glu Ala Ala Asp Arg
370                 375                 380

Glu Ala Glu Arg Ala Ala Asp Ala Ala Tyr Arg Ala Glu Gln Leu Arg
385                 390                 395                 400

Ile Ala Gln Glu Ala Ala Asp Ala Gln Lys Ala Leu Ala Glu Ala Leu
            405                 410                 415

Ala Asn Ala Gly Asn Asn Asp Asn Gly Gly Asp Asn Ser Ser Asp Asp
        420                 425                 430

Lys Gly Thr Gly Ser Ser Asp Ile Gly Thr Trp Gly Pro Phe Ala Ala
            435                 440                 445

Ile Ala Ala Ile Ile Ala Ala Ile Ala Ala Ile Phe Pro Phe Leu Ser
450                 455                 460

Gly Ile Val Lys Phe
465

<210> SEQ ID NO 86
<211> LENGTH: 4
<212> TYPE: PRT
<213> ORGANISM: Corynebacterium glutamicum
<220> FEATURE:
<221> NAME/KEY: misc_feature
<222> LOCATION: (4)..(4)
<223> OTHER INFORMATION: Xaa is Asn, Gly, Thr, Pro, or Ala

<400> SEQUENCE: 86

Gln Glu Thr Xaa
1

<210> SEQ ID NO 87
<211> LENGTH: 5
<212> TYPE: PRT
<213> ORGANISM: Corynebacterium glutamicum
<220> FEATURE:
<221> NAME/KEY: MISC_FEATURE
<222> LOCATION: (4)..(4)
<223> OTHER INFORMATION: Xaa is Asn, Gly, Thr, Pro, or Ala
<220> FEATURE:
<221> NAME/KEY: MISC_FEATURE
<222> LOCATION: (5)..(5)
<223> OTHER INFORMATION: Xaa is Pro, Thr, or Val

<400> SEQUENCE: 87

Gln Glu Thr Xaa Xaa
1               5

<210> SEQ ID NO 88
<211> LENGTH: 6
<212> TYPE: PRT
<213> ORGANISM: Corynebacterium glutamicum
```

```
<220> FEATURE:
<221> NAME/KEY: MISC_FEATURE
<222> LOCATION: (4)..(4)
<223> OTHER INFORMATION: Xaa is Asn, Gly, Thr, Pro, or Ala
<220> FEATURE:
<221> NAME/KEY: MISC_FEATURE
<222> LOCATION: (5)..(5)
<223> OTHER INFORMATION: Xaa is Pro, Thr, or Val
<220> FEATURE:
<221> NAME/KEY: MISC_FEATURE
<222> LOCATION: (6)..(6)
<223> OTHER INFORMATION: Xaa is Thr or Tyr

<400> SEQUENCE: 88

Gln Glu Thr Xaa Xaa Xaa
1               5

<210> SEQ ID NO 89
<211> LENGTH: 6
<212> TYPE: PRT
<213> ORGANISM: Corynebacterium glutamicum

<400> SEQUENCE: 89

Gln Glu Thr Asn Pro Thr
1               5

<210> SEQ ID NO 90
<211> LENGTH: 6
<212> TYPE: PRT
<213> ORGANISM: Corynebacterium glutamicum

<400> SEQUENCE: 90

Gln Glu Thr Gly Thr Tyr
1               5

<210> SEQ ID NO 91
<211> LENGTH: 6
<212> TYPE: PRT
<213> ORGANISM: Corynebacterium glutamicum

<400> SEQUENCE: 91

Gln Glu Thr Thr Val Thr
1               5

<210> SEQ ID NO 92
<211> LENGTH: 6
<212> TYPE: PRT
<213> ORGANISM: Corynebacterium glutamicum

<400> SEQUENCE: 92

Gln Glu Thr Pro Val Thr
1               5

<210> SEQ ID NO 93
<211> LENGTH: 6
<212> TYPE: PRT
<213> ORGANISM: Corynebacterium glutamicum

<400> SEQUENCE: 93

Gln Glu Thr Ala Val Thr
1               5

<210> SEQ ID NO 94
<211> LENGTH: 4
<212> TYPE: PRT
<213> ORGANISM: Artificial Sequence
<220> FEATURE:
```

<223> OTHER INFORMATION: Factor Xa

<400> SEQUENCE: 94

Ile Glu Gly Arg
1

<210> SEQ ID NO 95
<211> LENGTH: 6
<212> TYPE: PRT
<213> ORGANISM: Artificial Sequence
<220> FEATURE:
<223> OTHER INFORMATION: ProTEV

<400> SEQUENCE: 95

Glu Asn Leu Tyr Phe Gln
1               5

<210> SEQ ID NO 96
<211> LENGTH: 708
<212> TYPE: DNA
<213> ORGANISM: Corynebacterium glutamicum

<400> SEQUENCE: 96

```
atggacaacc agtctgacgg acaaatccgc gtactcgtcg ttgatgacga gccaaacatc     60
gtcgagctgc tcaccgtaag ccttaaattc caaggcttcg cagtgatgac cgccaacgat    120
ggcaatgaag ccctgaagat tgctcgtgag ttccgtccag acgcatacat cctcgatgtc    180
atgatgccag gaatggacgg cttcgagctg ctgaccaagc tgcgcggcga aggccttgac    240
agcccagttc tgtacctcac cgcaaaggat gccgtggagc accgcatcca cggcctgacc    300
atcggcgctg acgactacgt gaccaagcct ttctccctgg aagaagtaat cacccgcctg    360
cgcgtgattc ttcgtcgcgg tggagcagtt gaagaagaca cctcaacttc cctgcagtac    420
gcagacctca ccctcaacga tgaaacccac gaggtcacca aggctggcga actgatcgat    480
ctttccccaa ctgaattcaa cctcctgcgc tacctcatgc tcaacgctga agtggtgctg    540
tccaaggcaa agatcctgga taacgtgtgg cactacgatt ttggtggcga cggcaacgtc    600
gtggaatcct acatctccta cctgcgccgc aaggtggaca cccaggatcc gcagctaatt    660
cagactgttc gtggcgttgg atatgttctg cgcacccca gtagctaa               708
```

<210> SEQ ID NO 97
<211> LENGTH: 235
<212> TYPE: PRT
<213> ORGANISM: Corynebacterium glutamicum

<400> SEQUENCE: 97

Met Asp Asn Gln Ser Asp Gly Gln Ile Arg Val Leu Val Val Asp Asp
1               5                   10                  15

Glu Pro Asn Ile Val Glu Leu Leu Thr Val Ser Leu Lys Phe Gln Gly
                20                  25                  30

Phe Ala Val Met Thr Ala Asn Asp Gly Asn Glu Ala Leu Lys Ile Ala
            35                  40                  45

Arg Glu Phe Arg Pro Asp Ala Tyr Ile Leu Asp Val Met Met Pro Gly
        50                  55                  60

Met Asp Gly Phe Glu Leu Leu Thr Lys Leu Arg Gly Glu Gly Leu Asp
65                  70                  75                  80

Ser Pro Val Leu Tyr Leu Thr Ala Lys Asp Ala Val Glu His Arg Ile
                85                  90                  95

His Gly Leu Thr Ile Gly Ala Asp Asp Tyr Val Thr Lys Pro Phe Ser

-continued

```
            100                 105                 110
Leu Glu Glu Val Ile Thr Arg Leu Arg Val Ile Leu Arg Arg Gly Gly
            115                 120                 125

Ala Val Glu Glu Asp Thr Ser Thr Ser Leu Gln Tyr Ala Asp Leu Thr
            130                 135                 140

Leu Asn Asp Glu Thr His Glu Val Thr Lys Ala Gly Glu Leu Ile Asp
145                 150                 155                 160

Leu Ser Pro Thr Glu Phe Asn Leu Leu Arg Tyr Leu Met Leu Asn Ala
                165                 170                 175

Glu Val Val Leu Ser Lys Ala Lys Ile Leu Asp Asn Val Trp His Tyr
            180                 185                 190

Asp Phe Gly Gly Asp Gly Asn Val Val Glu Ser Tyr Ile Ser Tyr Leu
            195                 200                 205

Arg Arg Lys Val Asp Thr Gln Asp Pro Gln Leu Ile Gln Thr Val Arg
        210                 215                 220

Gly Val Gly Tyr Val Leu Arg Thr Pro Arg Ser
225                 230                 235
```